(12) United States Patent
Deng et al.

(10) Patent No.: US 9,982,237 B2
(45) Date of Patent: May 29, 2018

(54) COMPOSITIONS AND METHODS FOR REPROGRAMING NON-PLURIPOTENT CELLS INTO PLURIPOTENT STEM CELLS

(71) Applicant: Hong Guan Ltd., Beijing (CN)

(72) Inventors: Hongkui Deng, Beijing (CN); Yang Zhao, Beijing (CN); Pingping Hou, Beijing (CN); Yanqin Li, Beijing (CN); Xu Zhang, Beijing (CN); Chun Liu, Beijing (CN); Jingyang Guan, Beijing (CN); Honggang Li, Beijing (CN)

(73) Assignee: Hong Guan, Ltd., Beijing (CN)

( * ) Notice: Subject to any disclaimer, the term of this patent is extended or adjusted under 35 U.S.C. 154(b) by 35 days.

(21) Appl. No.: 14/904,195

(22) PCT Filed: Jul. 10, 2014

(86) PCT No.: PCT/CN2014/081961
§ 371 (c)(1),
(2) Date: Jan. 11, 2016

(87) PCT Pub. No.: WO2015/003643
PCT Pub. Date: Jan. 15, 2015

(65) Prior Publication Data
US 2016/0145581 A1    May 26, 2016

(30) Foreign Application Priority Data
Jul. 12, 2013  (CN) .......................... 2013 1 0292339

(51) Int. Cl.
*C12N 5/07*   (2010.01)
*C12N 5/074*  (2010.01)
*A61K 35/545* (2015.01)

(52) U.S. Cl.
CPC .......... *C12N 5/0696* (2013.01); *A61K 35/545* (2013.01); *C12N 2501/01* (2013.01); *C12N 2501/065* (2013.01); *C12N 2501/15* (2013.01); *C12N 2501/727* (2013.01); *C12N 2501/73* (2013.01); *C12N 2501/999* (2013.01); *C12N 2506/13* (2013.01); *C12N 2506/1307* (2013.01); *C12N 2506/1384* (2013.01)

(58) Field of Classification Search
CPC ............ C12N 25/0696; C12N 2501/01; C12N 2501/15; C12N 2501/727; C12N 2501/73
See application file for complete search history.

(56) References Cited

U.S. PATENT DOCUMENTS

| | | | |
|---|---|---|---|
| 5,716,404 A | 2/1998 | Vacanti | |
| 6,962,814 B2 | 11/2005 | Mitchell | |
| 7,914,579 B2 | 3/2011 | Vacanti | |
| 8,236,299 B2 | 8/2012 | Johe | |
| 8,637,494 B2 | 1/2014 | Naziruddin | |
| 8,728,495 B2 | 5/2014 | Sevrain | |
| 2006/0019326 A1 | 1/2006 | Vacanti | |
| 2007/0059293 A1 | 3/2007 | Atala | |
| 2011/0110899 A1* | 5/2011 | Shi | C12N 5/0696 424/93.7 |

FOREIGN PATENT DOCUMENTS

| | | |
|---|---|---|
| WO | 2009117439 | 9/2009 |
| WO | 2011082038 | 7/2011 |

OTHER PUBLICATIONS

Boyer, et al., "Core transcriptional regulatory circuitry in human embryonic stem cells", Cell, 122:947-56 (2005).
Chazaud, et al., "Early lineage segregation between epiblast and primitive endoderm in mouse blastocysts through the Grb2-MAPK pathway", Dev. Cell, 10:615-24 (2006).
Chen, at al., "H3K9 methylation is a barrier during somatic cell reprogramming into iPSCs", Nat. Genet., 45:34-42 (2013).
Chiang, et al., "Biological effects of inhibitors of S-adenosylhomocysteine hydrolase", Pharmacol Ther., 77:115-34 (1998).
Feldman, et al., "G9a-mediated irreversible epigenetic inactivation of Oct-3/4 during early embryogenesis", Nature Cell Biol., 8(2):180-91 (2006).
Gordon, et al., "Anti-HIV-1 activity of 3-deaza-adenosine analogs. Inhibition of S-adenosylhomocysteine hydrolase and nucleotide congeners", Eur. J. Biochem., 270:3507-17 (2003).
Hochedlinger, et al., "Ectopic expression of oct-4 blocks progenitor-cell differentiation and causes dysplasis in epithelial tissues", Cell, 121:465-477 (2005).
Insel, et al., "Forskolin as a tool for examining adenylyi cyclase expression, regulation, and G protein signaling", Cell. Mol. Neurobiol., 23:305-14 (2003).
Li, et a., Generation of iPSCs from mouse fibroblasts with a single gene, Oct4, and small olecules. Cell Research,21(1):196-204.
Li, et al., A mesenchymal-to-epithelial transition ates and is required for the nuclear reprogramming of mouse fibroblasts Cell Stem Cell, 7(1):51-63 (2010b).
Li, et al., "Identification of Oct4-activating compounds that enhance reprogramming efficiency", PNAS, 109:20853-8 (2012).
Lichti, et al, "Isolaton and short term culture of primary keratinocytes, hair follicle populations and dermal cells from newborn mice and keratinocytes from adult mice for in vitro analysis and for grafting to Immunodeficient mice", Nature Protocols, 3(5):799-810 (2008).
Lim, et al., "Sall4 regulates distinct transcription circuitries in different blastocyst-derived stem cell lineages", Cell Stem Cell, 3:543-54 (2008).

(Continued)

*Primary Examiner* — Kara Johnson
(74) *Attorney, Agent, or Firm* — Pabst Patent Group, LLP

(57) ABSTRACT

The invention provides a composition and a method for inducing pluripotency in non-pluripotent eukaryotic cells. The composition comprises chemical inducers of pluripotency (CIPs) including glycogen synthase kinase (GSK) inhibitors, TGFp receptor inhibitors, cyclic AMP agonists, S-adenosylhomocysteine hydrolase (SAH) inhibitors, and optionally an agent that promotes histone acetylation. The method comprises contacting a cell with the CIPs for a sufficient period of time to reprogram the cell into a pluripotent stem cell.

21 Claims, 21 Drawing Sheets

(56) References Cited

OTHER PUBLICATIONS

Longo, et al., "/?The chromosome make-up of mouse embryonic stem cells is predictive of somatic and germ cell chimaerism", Transgenic Research, 6:321-8 (1997).
Maherali, et al., "A hig-efficency system for the generation and study of human induced pluripotent stem cells", Cell Stem Cell, 3:340-5 (2008).
Maherali, et al., "Tgfbeta signal inhibition cooperates in the induction of iPSCs and replaces Sox2 and cMyc" Curr Biol., 19:1718-23 (2009).
Mc Qualter, et al., "Endogenous fibroblastic progenitor cells in the adult mouse lung are highly enriched in the sca-1 positive cell fraction" Stem Cells, 27:623-33 (2009).
Miranda, et al., "DZNeop is a global histone methylation inhibitor that reactivates developmental genes not silenced by DNA mothylation", Molecular Cancer herapeutics,8:1579-88 (2009).
Nakagawa, et al., "Promotion of direct reprogramming by transformation-deficient Myc", PNAS,. 107: 14152-7 (2010).
Neff, at al., "Dedifferentiation and the role of sall4 in reprogramming and patterning during amphibian limb regeneration", Dev. Dyn., 240:979-89 (2011).
Pan, et al., "A negative feedback loop of transcription factors that controls stem cell pluripotency and self-renewal" FASEB J,20(10): 1130-1132 (2006).
Saha, et al., "Technical challenges in using human induced pluripotent stem cells to model disease", Cell Stem Cell, 5:584-95 (2009).
Samavarchi-Tehrani, et al., "Functional genomics reveals a BMP-driven mesenchymal-to-epithelial transition in the initiation of somatic cell reprogramming", Cell Stem Cell, 71-14 (2010).
Seluanov, et al., "Establishing primary adult fibroblast cultures from rodents", J Vis Exp., 44:e2033 (2010).
Shapiro, et al., "Islet transplantation in seven patients with type 1 diabetes mellitus using a glucocorticoid-free immunosuppressive regimen", N Engl JMed., 343(4)230-8 (2000).
Shu, et al., "Induction of pluripotency in mouse somatic cells with lineage specifiers", Cell, 153:963-75 (2013).
Silva, et al., "Promotion of reprogramming to ground state pluripotency by signal inhibition", PLoS Biol., 6:e253 (2008).
Stadtfeld, et al., "Induced pluripotency: history, mechanisms, and applications", Genes Dev., 24:2239-63 (2010).
Takahashi, et al., "Induction of pluripotent stem cells from mouse embryonic and adult fibroblast cultures by defined factors", Cell, 126:663-76 (2006).
Tan, et al., "Pharmacologic disruption of polycomb-repressive complex 2-mediated gene repression selectively induces apoptosis in cancer cells", Genes and Dev., 21:1050-63 (2007).
Tat, et al., "The efficient generation of induced pluripotent stem (ips) cells from adult mouse adipose tissue-derived and neutral stem cells", Cell Transplant., 19:525-36 (2010).
Theunissen, et al., "Nanog overcomes reprogramming barriers and induces pluripotency in minimal conditions", Curr. Biol., 21:65-71 (2011).
Wilmut, et al., "Viable offspring derived from fetal and adult mammalian cells", Nature, 385:810-3 (1997).
Wu, et al., "Harnessing the potential of induced pluripotent stem cells for regenerative medicine", Cell Biol., 13:497-505 (2011).
Yamanaka, et al., "Nuclear reprogramming to a pluripotent state by three approaches", Nature, 465:704-12 (2010).
Ying, et al., "The ground state of embryonic stem cell self-renewal", Nature, 453: 519-23 (2008).
Zhao, et al., Two supporting factors greatly improve the efficiency of human iPSC generation, Cell Stem Cell, 3(5):475-9 (2008).
Zhu, et al., "Chemical strategies for stem cell biology and regenerative medicine", Annu. Rev. Biomed. Eng., 13:73-90 (2011).
International Search Report for PCT/CN2014/081961 dated Oct. 10, 2014.

\* cited by examiner

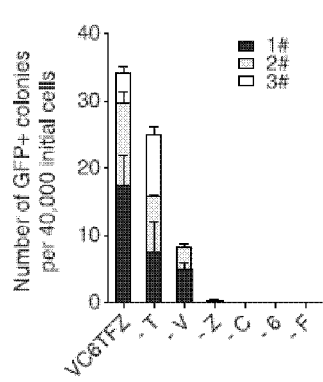
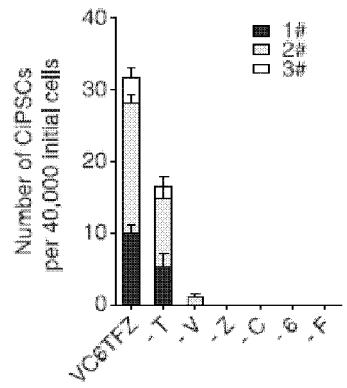
FIG. 8A  FIG. 8B
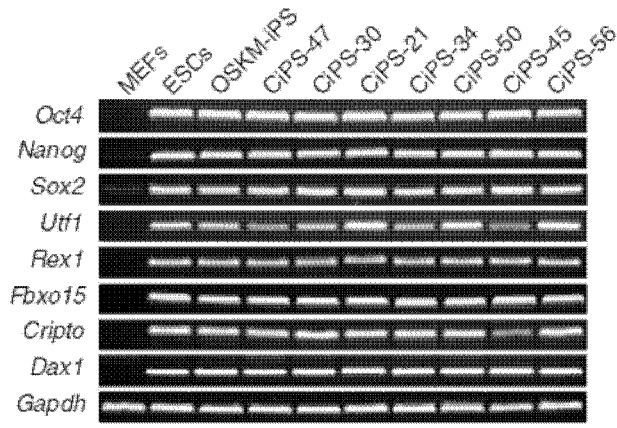
FIG. 9A
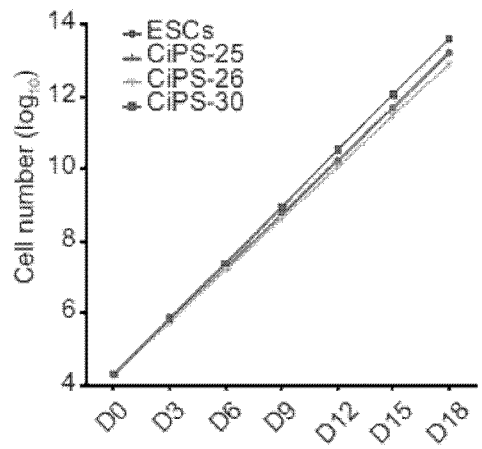
FIG. 9B

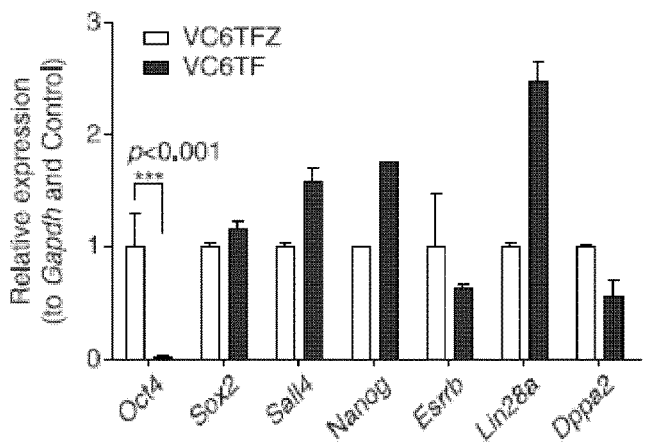
FIG. 11K
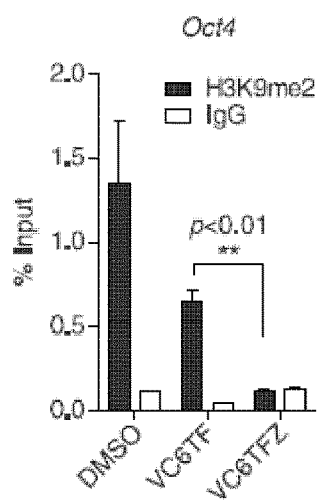
FIG. 11L
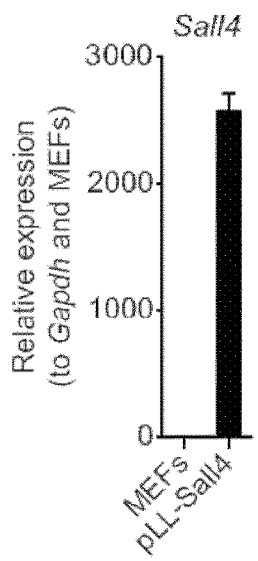 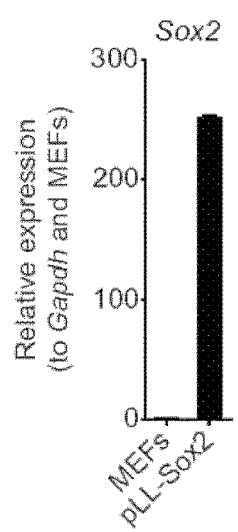
FIG. 12A  FIG. 12B

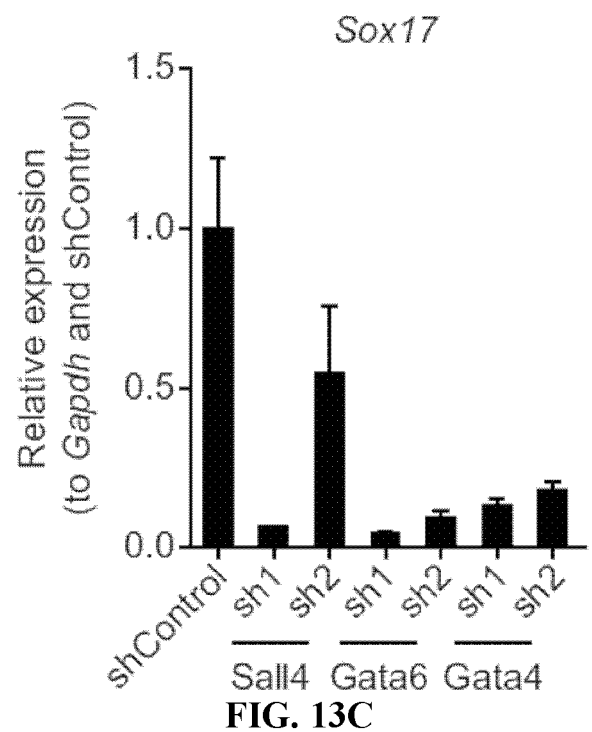
FIG. 13C
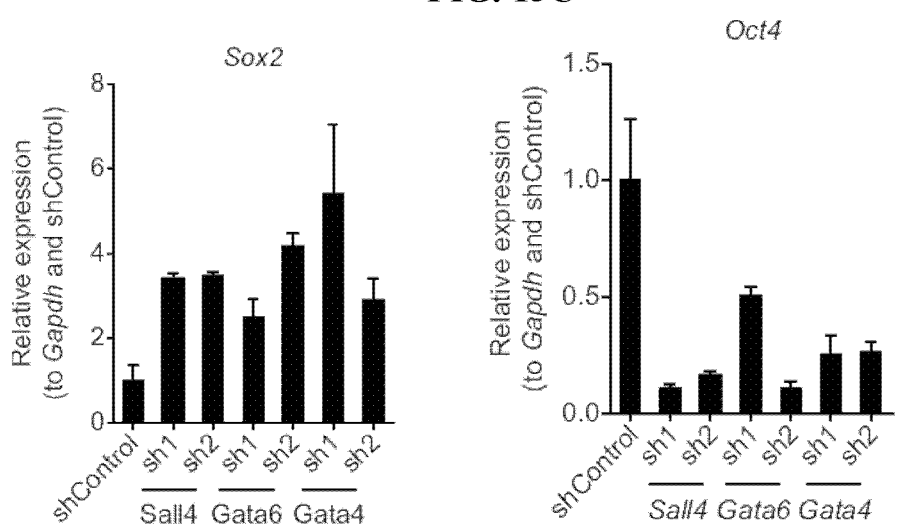
FIG. 13D
FIG. 13E

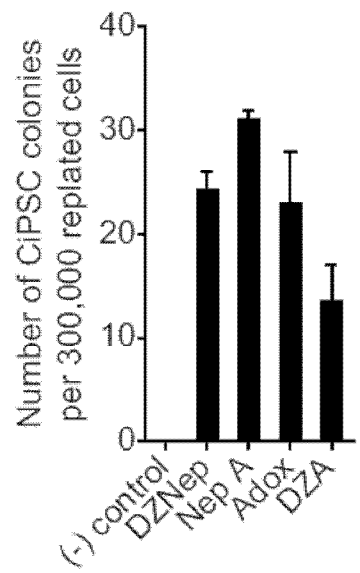
FIG. 14B
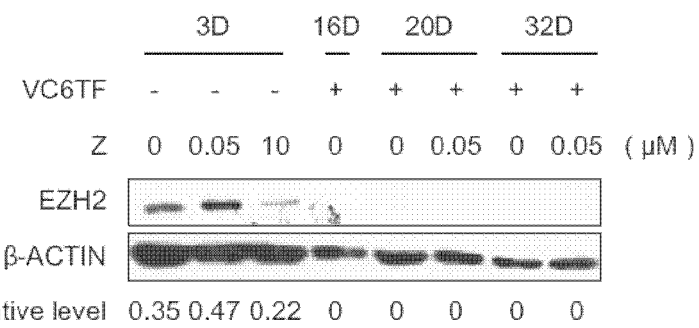
FIG. 14C
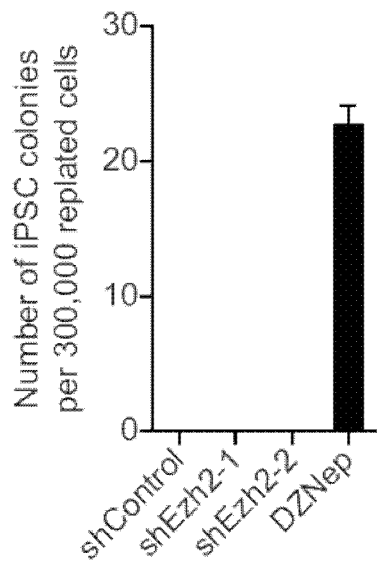 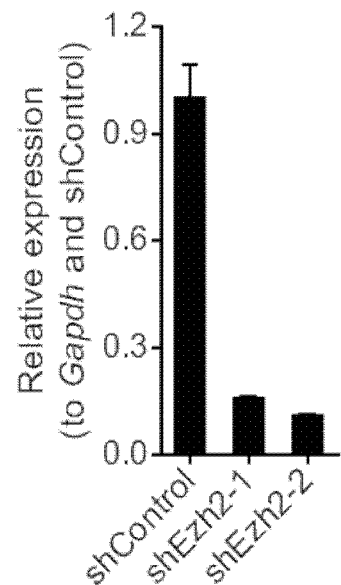
FIG. 14D　　　　　　　　　　FIG. 14E

SEQUENCE LISTING

```
<160> NUMBER OF SEQ ID NOS: 63

<210> SEQ ID NO 1
<211> LENGTH: 35
<212> TYPE: DNA
<213> ORGANISM: Artificial Sequence
<220> FEATURE:
<223> OTHER INFORMATION: Synthetic forward primer for Sall4 (plasmid
      construction)

<400> SEQUENCE: 1
actcgagcca ccatgtcgag gcgcaagcag gcgaa                               35

<210> SEQ ID NO 2
<211> LENGTH: 35
<212> TYPE: DNA
<213> ORGANISM: Artificial Sequence
<220> FEATURE:
<223> OTHER INFORMATION: Synthetic reverse primer for Sall4 (plasmid
      construction)

<400> SEQUENCE: 2
gcaattgtta gctgacagca atcttatttt cctcc                               35

<210> SEQ ID NO 3
<211> LENGTH: 22
<212> TYPE: DNA
<213> ORGANISM: Artificial Sequence
<220> FEATURE:
<223> OTHER INFORMATION: Synthetic forward primer for Sox2 (qRT-PCR)

<400> SEQUENCE: 3
cgggaagcgt gtacttatcc tt                                             22

<210> SEQ ID NO 4
```

```
<211> LENGTH: 21
<212> TYPE: DNA
<213> ORGANISM: Artificial Sequence
<220> FEATURE:
<223> OTHER INFORMATION: Synthetic reverse primer for Sox2 (qRT-PCR)

<400> SEQUENCE: 4
gcggagtgga aactttttgtc c                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic forward primer for Klf4 (qRT-PCR)

<400> SEQUENCE: 5
ttgcggtagt gcctggtcag tt                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic reverse  primer for Klf4 (qRT-PCR)

<400> SEQUENCE: 6
ctatgcaggc tgtggcaaaa cc                                              22

<210> SEQ ID NO 7
<211> LENGTH: 19
<212> TYPE: DNA
<213> ORGANISM: Artificial Sequence
<220> FEATURE:
<223> OTHER INFORMATION: Synthetic forward  primer for Oct4 (qRT-PCR)

<400> SEQUENCE: 7
cagggctttc atgtcctgg                                                  19

<210> SEQ ID NO 8
<211> LENGTH: 20
<212> TYPE: DNA
<213> ORGANISM: Artificial Sequence
<220> FEATURE:
<223> OTHER INFORMATION: Synthetic reverse primer for Oct4 (qRT-PCR)

<400> SEQUENCE: 8
agttggcgtg gagactttgc                                                 20

<210> SEQ ID NO 9
<211> LENGTH: 24
<212> TYPE: DNA
<213> ORGANISM: Artificial Sequence
<220> FEATURE:
<223> OTHER INFORMATION: Synthetic forward primer for Gata4 (qRT-PCR)

<400> SEQUENCE: 9
gagctggcct gcgatgtctg agtg                                            24

<210> SEQ ID NO 10
<211> LENGTH: 24
<212> TYPE: DNA
<213> ORGANISM: Artificial Sequence
<220> FEATURE:
<223> OTHER INFORMATION: Synthetic reverse primer for Gata4 (qRT-PCR)

<400> SEQUENCE: 10
```

```
aaacggaagc ccaagaacct gaat                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic forward  primer for Gata6 (qRT-PCR)

<400> SEQUENCE: 11
tgaggtggtc gcttgtgtag                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic reverse  primer for Gata6 (qRT-PCR)

<400> SEQUENCE: 12
atggcgtaga aatgctgagg                                               20

<210> SEQ ID NO 13
<211> LENGTH: 21
<212> TYPE: DNA
<213> ORGANISM: Artificial Sequence
<220> FEATURE:
<223> OTHER INFORMATION: Synthetic forward primer for Sox17 (qRT-PCR)

<400> SEQUENCE: 13
gtcaacgcct tccaagactt g                                             21

<210> SEQ ID NO 14
<211> LENGTH: 21
<212> TYPE: DNA
<213> ORGANISM: Artificial Sequence
<220> FEATURE:
<223> OTHER INFORMATION: Synthetic reverse primer for Sox17 (qRT-PCR)

<400> SEQUENCE: 14
gtaaaggtga aaggcgaggt g                                             21

<210> SEQ ID NO 15
<211> LENGTH: 19
<212> TYPE: DNA
<213> ORGANISM: Artificial Sequence
<220> FEATURE:
<223> OTHER INFORMATION: Synthetic forward primer for Esrrb (qRT-PCR)

<400> SEQUENCE: 15
gtggctgagg gcatcaatg                                                19

<210> SEQ ID NO 16
<211> LENGTH: 21
<212> TYPE: DNA
<213> ORGANISM: Artificial Sequence
<220> FEATURE:
<223> OTHER INFORMATION: Synthetic reverse primer for Esrrb (qRT-PCR)

<400> SEQUENCE: 16
aaccgaatgt cgtccgaaga c                                             21

<210> SEQ ID NO 17
<211> LENGTH: 21
<212> TYPE: DNA
```

<213> ORGANISM: Artificial Sequence
<220> FEATURE:
<223> OTHER INFORMATION: Synthetic forward primer for Sall4 (qRT-PCR)

<400> SEQUENCE: 17
tggcagacga aagttctttt c                                                    21

<210> SEQ ID NO 18
<211> LENGTH: 22
<212> TYPE: DNA
<213> ORGANISM: Artificial Sequence
<220> FEATURE:
<223> OTHER INFORMATION: Synthetic reverse primer for Sall4 (qRT-PCR)

<400> SEQUENCE: 18
tccaacattt atccgagcac ag                                                   22

<210> SEQ ID NO 19
<211> LENGTH: 21
<212> TYPE: DNA
<213> ORGANISM: Artificial Sequence
<220> FEATURE:
<223> OTHER INFORMATION: Synthetic forward primer for Lin28a (qRT-PCR)

<400> SEQUENCE: 19
ccgcagttgt agcacctgtc t                                                    21

<210> SEQ ID NO 20
<211> LENGTH: 22
<212> TYPE: DNA
<213> ORGANISM: Artificial Sequence
<220> FEATURE:
<223> OTHER INFORMATION: Synthetic reverse primer for Lin28a (qRT-PCR)

<400> SEQUENCE: 20
gaagaacatg cagaagcgaa ga                                                   22

<210> SEQ ID NO 21
<211> LENGTH: 21
<212> TYPE: DNA
<213> ORGANISM: Artificial Sequence
<220> FEATURE:
<223> OTHER INFORMATION: Synthetic forward primer for Dppa2 (qRT-PCR)

<400> SEQUENCE: 21
gcgtagcgta gtctgtgttt g                                                    21

<210> SEQ ID NO 22
<211> LENGTH: 22
<212> TYPE: DNA
<213> ORGANISM: Artificial Sequence
<220> FEATURE:
<223> OTHER INFORMATION: Synthetic reverse primer for Dppa2 (qRT-PCR)

<400> SEQUENCE: 22
tcaacgagaa ccaatctgag ga                                                   22

<210> SEQ ID NO 23
<211> LENGTH: 21
<212> TYPE: DNA
<213> ORGANISM: Artificial Sequence
<220> FEATURE:
<223> OTHER INFORMATION: Synthetic forward primer for Nanog (qRT-PCR)

<400> SEQUENCE: 23
agttatggag cggagcagca t                                                    21

<210> SEQ ID NO 24
<211> LENGTH: 18
<212> TYPE: DNA
<213> ORGANISM: Artificial Sequence
<220> FEATURE:
<223> OTHER INFORMATION: Synthetic reverse primer for Nanog (qRT-PCR)

<400> SEQUENCE: 24
aggcctggac cgctcagt                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic forward primer for Oct4 (genomic PCR)

<400> SEQUENCE: 25
gaaggatgtg gtccgagt                                                 18

<210> SEQ ID NO 26
<211> LENGTH: 20
<212> TYPE: DNA
<213> ORGANISM: Artificial Sequence
<220> FEATURE:
<223> OTHER INFORMATION: Synthetic reverse primer for Oct4 (genomic PCR)

<400> SEQUENCE: 26
gcagcgtatc cacatagcgt                                               20

<210> SEQ ID NO 27
<211> LENGTH: 18
<212> TYPE: DNA
<213> ORGANISM: Artificial Sequence
<220> FEATURE:
<223> OTHER INFORMATION: Synthetic forward primer for Sox2 (genomic PCR)

<400> SEQUENCE: 27
catgggttcg gtggtcaa                                                 18

<210> SEQ ID NO 28
<211> LENGTH: 20
<212> TYPE: DNA
<213> ORGANISM: Artificial Sequence
<220> FEATURE:
<223> OTHER INFORMATION: Synthetic reverse primer for Sox2 (genomic PCR)

<400> SEQUENCE: 28
gcagcgtatc cacatagcgt                                               20

<210> SEQ ID NO 29
<211> LENGTH: 18
<212> TYPE: DNA
<213> ORGANISM: Artificial Sequence
<220> FEATURE:
<223> OTHER INFORMATION: Synthetic forward primer for Klf4 (genomic PCR)

<400> SEQUENCE: 29
accactgtga ctgggacg                                                 18

<210> SEQ ID NO 30
<211> LENGTH: 20
<212> TYPE: DNA
<213> ORGANISM: Artificial Sequence
<220> FEATURE:

<223> OTHER INFORMATION: Synthetic reverse primer for Klf4 (genomic PCR)

<400> SEQUENCE: 30
gcagcgtatc cacatagcgt          20

<210> SEQ ID NO 31
<211> LENGTH: 20
<212> TYPE: DNA
<213> ORGANISM: Artificial Sequence
<220> FEATURE:
<223> OTHER INFORMATION: Synthetic forward primer for c-Myc (genomic PCR)

<400> SEQUENCE: 31
tacatcctgt ccgtccaagc          20

<210> SEQ ID NO 32
<211> LENGTH: 20
<212> TYPE: DNA
<213> ORGANISM: Artificial Sequence
<220> FEATURE:
<223> OTHER INFORMATION: Synthetic reverse primer for c-Myc (genomic PCR)

<400> SEQUENCE: 32
gcagcgtatc cacatagcgt          20

<210> SEQ ID NO 33
<211> LENGTH: 19
<212> TYPE: DNA
<213> ORGANISM: Artificial Sequence
<220> FEATURE:
<223> OTHER INFORMATION: Synthetic forward primer for hOct4 (genomic PCR)

<400> SEQUENCE: 33
acctccatag aagacaccg          19

<210> SEQ ID NO 34
<211> LENGTH: 18
<212> TYPE: DNA
<213> ORGANISM: Artificial Sequence
<220> FEATURE:
<223> OTHER INFORMATION: Synthetic reverse primer for hOct4 (genomic PCR)

<400> SEQUENCE: 34
tagccccact ccaacctg          18

<210> SEQ ID NO 35
<211> LENGTH: 19
<212> TYPE: DNA
<213> ORGANISM: Artificial Sequence
<220> FEATURE:
<223> OTHER INFORMATION: Synthetic forward primer for hSox2 (genomic PCR)

<400> SEQUENCE: 35
acctccatag aagacaccg          19

<210> SEQ ID NO 36
<211> LENGTH: 22
<212> TYPE: DNA
<213> ORGANISM: Artificial Sequence
<220> FEATURE:
<223> OTHER INFORMATION: Synthetic reverse primer for hSox2 (genomic PCR)

```
<400> SEQUENCE: 36
ctccgacaaa agtttccact cg                                            22

<210> SEQ ID NO 37
<211> LENGTH: 19
<212> TYPE: DNA
<213> ORGANISM: Artificial Sequence
<220> FEATURE:
<223> OTHER INFORMATION: Synthetic foerward primer for hKlf4 (genomic
      PCR)

<400> SEQUENCE: 37
acctccatag aagacaccg                                                19

<210> SEQ ID NO 38
<211> LENGTH: 18
<212> TYPE: DNA
<213> ORGANISM: Artificial Sequence
<220> FEATURE:
<223> OTHER INFORMATION: Synthetic reverse primer for hKLF (genomic
      PCR)

<400> SEQUENCE: 38
gaagaggagg ctgacgct                                                 18

<210> SEQ ID NO 39
<211> LENGTH: 19
<212> TYPE: DNA
<213> ORGANISM: Artificial Sequence
<220> FEATURE:
<223> OTHER INFORMATION: Synthetic forward primer for hcMyc (genomic
      PCR)

<400> SEQUENCE: 39
acctccatag aagacaccg                                                19

<210> SEQ ID NO 40
<211> LENGTH: 18
<212> TYPE: DNA
<213> ORGANISM: Artificial Sequence
<220> FEATURE:
<223> OTHER INFORMATION: Synthetic reverse primer for hcMyc (genomic
      PCR)

<400> SEQUENCE: 40
gggtcgcaga tgaaactc                                                 18

<210> SEQ ID NO 41
<211> LENGTH: 22
<212> TYPE: DNA
<213> ORGANISM: Artificial Sequence
<220> FEATURE:
<223> OTHER INFORMATION: Synthetic forward primer for Oct4 (bisulfite
      genomic sequencing)

<400> SEQUENCE: 41
ggagtggttt tagaaataat tg                                            22

<210> SEQ ID NO 42
<211> LENGTH: 23
<212> TYPE: DNA
<213> ORGANISM: Artificial Sequence
<220> FEATURE:
<223> OTHER INFORMATION: Synthetic reverse primer for Oct4 (bisulfite
      genomic sequencing)

<400> SEQUENCE: 42
```
tccaacccta ctaacccatc acc                                         23

<210> SEQ ID NO 43
<211> LENGTH: 30
<212> TYPE: DNA
<213> ORGANISM: Artificial Sequence
<220> FEATURE:
<223> OTHER INFORMATION: Synthetic forward primer for Nanog (bisulfite
      genomic sequencing)

<400> SEQUENCE: 43
gattttgtag gtgggattaa ttgtgaattt                                  30

<210> SEQ ID NO 44
<211> LENGTH: 30
<212> TYPE: DNA
<213> ORGANISM: Artificial Sequence
<220> FEATURE:
<223> OTHER INFORMATION: Synthetic reverse primer for Nanog (bisulfite
      genomic sequencing)

<400> SEQUENCE: 44
accaaaaaaa cccacactca tatcaatata                                  30

<210> SEQ ID NO 45
<211> LENGTH: 20
<212> TYPE: DNA
<213> ORGANISM: Artificial Sequence
<220> FEATURE:
<223> OTHER INFORMATION: Synthetic forward primer for Oct4 (chromatin
      immunoprecipitation)

<400> SEQUENCE: 45
ctgtaaggac aggccgagag                                             20

<210> SEQ ID NO 46
<211> LENGTH: 20
<212> TYPE: DNA
<213> ORGANISM: Artificial Sequence
<220> FEATURE:
<223> OTHER INFORMATION: Synthetic reverse primer for Oct4 (chromatin
      immunoprecipitation)

<400> SEQUENCE: 46
caggaggcct tcattttcaa                                             20

<210> SEQ ID NO 47
<211> LENGTH: 19
<212> TYPE: DNA
<213> ORGANISM: Artificial Sequence
<220> FEATURE:
<223> OTHER INFORMATION: Synthetic forward primer for Nanog (chromatin
      immunoprecipitation)

<400> SEQUENCE: 47
ctatcgcctt gagccgttg                                              19

<210> SEQ ID NO 48
<211> LENGTH: 26
<212> TYPE: DNA
<213> ORGANISM: Artificial Sequence
<220> FEATURE:
<223> OTHER INFORMATION: Synthetic reverse primer for Nanog (chromatin
      immunoprecipitation)

<400> SEQUENCE: 48

```
aactcagtgt ctagaaggaa agatca                                          26
```

<210> SEQ ID NO 49
<211> LENGTH: 21
<212> TYPE: DNA
<213> ORGANISM: Artificial Sequence
<220> FEATURE:
<223> OTHER INFORMATION: Synthetic forward primer for Sox2 (chromatin
      immunoprecipitation)

<400> SEQUENCE: 49

```
tttattcagt tcccagtcca a                                               21
```

<210> SEQ ID NO 50
<211> LENGTH: 22
<212> TYPE: DNA
<213> ORGANISM: Artificial Sequence
<220> FEATURE:
<223> OTHER INFORMATION: Synthetic reverse primer for Sox2 (chromatin
      immunoprecipitation)

<400> SEQUENCE: 50

```
ttattcctat gtgtgagcaa ga                                              22
```

<210> SEQ ID NO 51
<211> LENGTH: 19
<212> TYPE: DNA
<213> ORGANISM: Artificial Sequence
<220> FEATURE:
<223> OTHER INFORMATION: Synthetic forward primer for OG (For OG (Oct4
      promoter-driven GFP) cassette)

<400> SEQUENCE: 51

```
aaccactacc tgagcaccc                                                  19
```

<210> SEQ ID NO 52
<211> LENGTH: 20
<212> TYPE: DNA
<213> ORGANISM: Artificial Sequence
<220> FEATURE:
<223> OTHER INFORMATION: Synthetic reverse primer for OG (For OG (Oct4
      promoter-driven GFP) cassette)

<400> SEQUENCE: 52

```
acctctacaa atgtggtatg                                                 20
```

<210> SEQ ID NO 53
<211> LENGTH: 58
<212> TYPE: DNA
<213> ORGANISM: Artificial Sequence
<220> FEATURE:
<223> OTHER INFORMATION: Synthetic Sall4 ShRNA 1 sequence

<400> SEQUENCE: 53

```
ccggcagccc acctttgtca agttctcga gaactttgac aaaggtgggc tgttttttg       58
```

<210> SEQ ID NO 54
<211> LENGTH: 58
<212> TYPE: DNA
<213> ORGANISM: Artificial Sequence
<220> FEATURE:
<223> OTHER INFORMATION: Synthetic Sall4 ShRNA 2 sequence

<400> SEQUENCE: 54

```
ccgggcccac ctttgtcaaa gttgactcga gtcaactttg acaaaggtgg gcttttttg      58
```

-continued

```
<210> SEQ ID NO 55
<211> LENGTH: 58
<212> TYPE: DNA
<213> ORGANISM: Artificial Sequence
<220> FEATURE:
<223> OTHER INFORMATION: Synthetic Gata4 ShRNA 1 sequence

<400> SEQUENCE: 55
ccggagccca agaacctgaa taaatctcga gatttattca ggttcttggg cttttttg        58

<210> SEQ ID NO 56
<211> LENGTH: 58
<212> TYPE: DNA
<213> ORGANISM: Artificial Sequence
<220> FEATURE:
<223> OTHER INFORMATION: Synthetic Gata4 ShRNA 2 sequence

<400> SEQUENCE: 56
ccggcatctc ctgtcactca gacatctcga gatgtctgag tgacaggaga tgttttg         58

<210> SEQ ID NO 57
<211> LENGTH: 58
<212> TYPE: DNA
<213> ORGANISM: Artificial Sequence
<220> FEATURE:
<223> OTHER INFORMATION: Synthetic Gata6 ShRNA 1 sequence

<400> SEQUENCE: 57
ccggccacta ccttatggcg tagaactcga gttctacgcc ataaggtagt ggttttg         58

<210> SEQ ID NO 58
<211> LENGTH: 58
<212> TYPE: DNA
<213> ORGANISM: Artificial Sequence
<220> FEATURE:
<223> OTHER INFORMATION: Synthetic Gata6 ShRNA 2 sequence

<400> SEQUENCE: 58
ccggcctcga ccacttgcta tgaaactcga gtttcatagc aagtggtcga ggttttg         58

<210> SEQ ID NO 59
<211> LENGTH: 58
<212> TYPE: DNA
<213> ORGANISM: Artificial Sequence
<220> FEATURE:
<223> OTHER INFORMATION: Synthetic Sox17 ShRNA 1 sequence

<400> SEQUENCE: 59
ccggcccaca atcactgtcc agtttctcga gaaactggac agtgattgtg ggttttg         58

<210> SEQ ID NO 60
<211> LENGTH: 58
<212> TYPE: DNA
<213> ORGANISM: Artificial Sequence
<220> FEATURE:
<223> OTHER INFORMATION: Synthetic Sox17 ShRNA 2 sequence

<400> SEQUENCE: 60
ccggcgcacg gaattcgaac agtatctcga gatactgttc gaattccgtg cgttttg         58

<210> SEQ ID NO 61
<211> LENGTH: 58
<212> TYPE: DNA
<213> ORGANISM: Artificial Sequence
<220> FEATURE:
<223> OTHER INFORMATION: Synthetic Ezh2 ShRNA 1 sequence
```

-continued

```
<400> SEQUENCE: 61
ccgggctagg ctaattggga ccaaactcga gtttggtccc aattagccta gcttttg        58

<210> SEQ ID NO 62
<211> LENGTH: 58
<212> TYPE: DNA
<213> ORGANISM: Artificial Sequence
<220> FEATURE:
<223> OTHER INFORMATION: Synthetic Ezh2 ShRNA 2 sequence

<400> SEQUENCE: 62
ccggcggctc ctctaaccat gtttactcga gtaaacatgg ttagaggagc cgtttttg       58

<210> SEQ ID NO 63
<211> LENGTH: 58
<212> TYPE: DNA
<213> ORGANISM: Artificial Sequence
<220> FEATURE:
<223> OTHER INFORMATION: Synthetic control ShRNA  sequence

<400> SEQUENCE: 63
ccggcaacaa gatgaagagc accaactcga gttggtgctc ttcatcttgt tgtttttg       58
```

COMPOSITIONS AND METHODS FOR REPROGRAMING NON-PLURIPOTENT CELLS INTO PLURIPOTENT STEM CELLS

CROSS REFERENCE TO RELATED APPLICATIONS

This application is a 371 International Application No. PCT/CN2014/081961, filed Jul. 10, 2014, which claims the benefit of Chinese Application 201310292339.9, filed Jul. 12, 2013, herein incorporated by references in its entirety.

REFERENCE TO SEQUENCE LISTING

The Sequence Listing submitted Jan. 11, 2016, as a text file named "HGL_100_ST25.txt," created on Jul. 3, 2014, and having a size of 14,342 bytes is hereby incorporated by reference.

FIELD OF THE INVENTION

The present invention generally relates to small molecule compositions and methods for reprogramming eukaryotic cells into pluripotent cells.

BACKGROUND OF THE INVENTION

Pluripotent stem cells, such as embryonic stem cells (ESCs), can self-renew and differentiate into all somatic cell types. Somatic cells have been reprogrammed to become pluripotent via nuclear transfer into oocytes or through the ectopic expression of defined factors (Wilmut, et al., *Nature*, 385:810-813 (1997); Takahashi, et al., *Cell*, 126:663-676 (2006); Yamanaka, et al., *Nature*, 465:704-712 (2010) and Stadtfeld, et al., *Genes Dev.*, 24:2239-2263 (2010)). However, exogenous pluripotency-associated factors, especially Oct4, are indispensable in these methods for establishing pluripotency (Zhu, *Annu. Rev. Biomed. Eng.*, 13:73-90 (2011); Li, *Cell Res.*, 21:196-204 (2011) and Li, et al., *Proc. Natl. Acad. Sci. U.S.A.*, 109:20853-20858 (2012)). Additionally, the requirement for tumorigenic genes like c-Myc in these reprogramming methods creates a risk of inducing cancerous cells. Accordingly, reprogramming strategies have raised concerns regarding the clinical applications (Saha, et al., *Cell Stem Cell*, 5:584-595 (2009) and Wu, et al., *Cell Biol.*, 13:497-505 (2011)).

There is a need for small molecules which can drive reprogramming of somatic cells into pluripotent cells. Small molecules that can induce pluripotency have advantages because small molecules more readily penetrate the cells, they are nonimmunogenic, more cost-effective, and more easily synthesized, preserved, and standardized.

It is an object of the present invention to provide small molecules which can be used to reprogram partially or completely differentiated cells into pluripotent cells.

It is also an object of the present invention to provide a method of reprogramming partially or completely differentiated cells into pluripotent cells.

SUMMARY OF THE INVENTION

Small molecules have been identified which can be used to reprogram partially or completely differentiated cells, including cells that are not genetically engineered to express one or more markers of pluripotency such as Oct4, and which do not naturally express Oct4, into pluripotent cells. The required chemical inducers of pluripotency (CIPs) include (1) a glycogen synthase kinase (GSK) inhibitor, (2) a TGFβ receptor inhibitor, (3) a cyclic AMP agonist, (4) a S-adenosylhomocysteine hydrolase (SAH) inhibitor, (5) an agent which promotes histone acetylation, such as a histone deacetylase (HDAC) inhibitor (for example, valproic acid (VPA)), and combinations thereof. The CIPs may be provided separately or in combination as a CIP composition. One or more epigenetic modulators and retinoic acid receptor agonists, for example, retinoic receptor ligands may also be administered with the CIPs. In some preferred embodiments, the CIPs include DZNep as an SAH inhibitor.

In a preferred embodiment, the GSK inhibitor is the aminopyrimidine, CHIR99021 ("CHIR") which has the chemical name [6-[[2-[[4-(2,4-Dichlorophenyl)-5-(5-methyl-1H-imidazol-2-yl)-2-pyrimidinyl]amino]ethyl]amino]-3-pyridinecarbonitrile]; the TGFβ receptor inhibitor is [2-(3-(6-Methylpyridin-2-yl)-1H-pyrazol-4-yl)-1,5-naphthyridine] (616452); the cAMP agonist is Forskolin (FSK) and the SAH inhibitor is 3-deazaneplanocin A (DZNep). In some embodiments, the CIPs are a combination of CHIR, 616452, FSK and DZNep (C6FZ). In a more preferred embodiment, the CIPs are a combination of VPA, CHIR, 616452, Tranylcypromine (Parnet), FSK (collectively, VC6TF) and DZNep (collectively, VC6TFZ).

In a preferred embodiment, epigenetic modulators that can be included in the CIP composition include one or more of 5-azacytidine, sodium butyrate and RG108 and combinations thereof. In some embodiments, small molecules that facilitate late reprogramming and small molecules that improve/boost chemical reprogramming efficiency over the levels seen with VC6TFZ are included. In a preferred embodiment, the small molecule that facilitates late reprogramming is a cAMP agonist such as prostaglandin E2 (PGE2), FSK and rolipram or combinations thereof. Small molecules that improve/boost chemical reprogramming efficiency include prostaglandin E2 (PGE2), [N-(9,10-dioxo-9,10-dihydrophenanthren-2-yl)pivalamide] (SF1670), [N-(4-(Diethylaminobenzylidenyl)-N'-(4-hydroxybenzoyl)-hydrazine] (DY131 DY131), [2-Cyclohexyl-6-methoxy-N-[1-(1-methylethyl)-4-piperidinyl]-7-[3-(1-pyrrolidinyl)propoxy]-4-quinazolinamine] (UNC0638), [N-(2-(3-(piperazin-1-ylmethyl)imidazo[2,1-b]thiazol-6-yl)phenyl)quinoxaline-2-carboxamide hydrochloride] (SRT1720), [N-Phthalyl-L-tryptophan] (RG108), 2-Me-5HT (2-methyl-5-hydroxytryptamine), [3,7-Dihydro-1-methyl-3-(2-methyl-propyl)-1H-purine-2,6-dioneand] (IBMX) and [4-[(E)-2-(5,6,7,8-Tetrahydro-5,5,8,8-tetramethyl-2-naphthalenyl)-1-propenyl]benzoic acid] (TTNPB). A preferred small molecule for boosting chemical reprogramming efficiency is TTNPB.

Several protein factors, such as recombinant basic fibroblast growth factor (bFGF), have also been demonstrated to be effective in the following protocol for chemical reprogramming.

Also provided is a method of inducing reprogramming of a cell of a first type which is not a pluripotent cell, such as a somatic cell, into a pluripotent cell. Preferred cells to reprogram include fibroblast cells, adipose-derived stem cells (ADSC), neural derived stem cells and intestinal epithelial cells. In a preferred embodiment the method does not include transfecting the cell to be reprogrammed so that it expresses any of Oct4, KLF4, SOX2, C-Myc or NANOG. In this embodiment, the method also does not include contacting the cell to be reprogrammed with a polypeptide such as a transcription factors. The cell to be reprogrammed is contacted with the CIPs for a sufficient period of time to reprogram the cell into a chemically induced pluripotent stem cell (CiPSC). The reprogrammed cell is identified as a pluripotent cell based on ESC-like properties such as morphology, doubling time, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. The CiPSCs are isolated and can be further cultured.

In a preferred embodiment, cells are cultured initially in a reprogramming medium containing the CIPs for a period between 26-36 days. The cells are then cultured in 2i-medium (an ESC culture medium with dual inhibition of glycogen synthase kinase-3 and mitogen-activated protein kinase signaling) for more than 4 days. In some embodiments, the cells are cultured in 2i-medium from 4 to 20 days. In some embodiments, culture in 2i-medium is commenced about day 28 post treatment with reprogramming medium. Different durations of exposure of the cells to the small molecules (CIPs) have been tested. 616452 and Forskolin need to be present the entire time before the use of 2i-medium. CHIR99021 should be used in the first 12 days, and is preferably present the entire time before the use of 2i-medium. DZNep should be added at the late stage of reprogramming (day 12 to day 40), preferably by day 16-20 after the initial treatment of other small molecules. The small molecule combination (VC6TFZ) should be changed into 2i-medium between day 28 to day 48, and preferably day 40.

The cells are preferably cultured for about 16-20 days in reprogramming medium including the CIP components VC6TF, then cultured in VC6TFZ for the remaining period of time required to convert the cells to pluripotent cells. In some embodiments, the cells are further contacted with small molecules that facilitate late reprogramming, for example, the cAMP agonists and epigenetic modulators and/or small molecules that improve/boost chemical reprogramming efficiency, as disclosed herein. A preferred small molecule for boosting chemical reprogramming efficiency is TTNPB.

Isolated chemically induced pluripotent stem cells (CiPSCs), are not naturally occurring pluripotent stem cells. CiPSCs possess ESC-like properties such as ESC morphology, doubling time similar to ESC, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. CiPSCs are different from ESCs for example, in that they are not directly derived/isolated from the inner cell mass of a blastocyst. CiPSCs are different from other induced pluripotent stem cells (iPSC) in that they are not engineered to express a transgene such as genes expressing Oct4, KLF4, SOX2, c-Myc or NANOG, or are not produced by a process that includes transfecting the cells from which they obtained to express any of these transgenes. CiPSCs are also different from other induced pluripotent stem cells (iPSC) in that they are not produced by a process that includes contacting non-pluripotent cells with one or more polypeptides such as Klf, Oct, Myc or Sox. In a preferred embodiment, the CiPSCs are not genetically engineered, i.e., the CiPSCs are not altered by introducing or removing genetic elements from the cells. There is no obvious difference among CiPSCs, iPSCs and ESCs. However, CiPSCs disclosed herein can be distinguished from ESC at least by the methods that are used to generate them i.e., by their origin. Where ESC are naturally occurring cells, CiPSCs on the other hand are not naturally occurring and are obtained by treating non-pluripotent cells with a combination of small molecules, as described herein.

The CiPSCs can be cultured or induced to differentiate into cells of a desired type. The CiPSCs and their progeny can be used in a number of applications, including but not limited to cell therapy and tissue engineering.

BRIEF DESCRIPTION OF THE DRAWINGS

FIGS. 5A-G show the number of colonies of CiPSC cells as a function of the concentrations of small molecules as indicated (titrated during CiPSC induction). FIG. 5H shows Durations of each small molecule. FIGS. 5I-K show durations of the chemical combinations. The chemical reprogramming medium plus VC6TFZ was replaced with 2i-medium at different time points. Error bars indicate the s.d. (n≥2).

FIG. 6A shows validated small molecules improving chemical reprogramming efficiency in combination with VC6TFZ in MEFs. Chemicals added from day 0 to day 12: PGE2, DY131, RG108, 2-Me-5HT and IBMX; chemicals added after day 12: SF1670, UNC0638 and SRT1720. (−) control, DMSO. Error bars indicate the s.d. (n.gtoreq.2). FIG. 6B shows the effect of TTNPB on improving chemical reprogramming efficiency in combination with C6FZ or VC6TFZ in MEFs. CiPSC colonies were quantified on day 50 and day 40 for chemical reprogramming by C6FZ and VC6TFZ, respectively. iPSC colonies were quantified on day 24 and day 16 for OSK- and OSKM-induced reprogramming, respectively. Error bars indicate s.d. (n=3). FIG. 6C shows the effect of TTNPB on improving chemical reprogramming kinetics in combination with VC6TFZ in MEFs. GFP-positive colonies were quantified on the indicated days. (−) control, VC6TFZ. Error bars indicate s.d. (n=3). FIG. 6D shows marker expression in MAF-CiPS cells. FIGS. 6E and 6F show Genomic PCR analysis for CiPSCs.

FIGS. 7A and B shows genomic PCR for two sets of viral vectors used. FIG. 7C is a southern blot analysis to detect viral integration events. DNA probe was designed on psi sequence to target both pLL3.7-ΔU6 and tet-on vectors. CiPSCs were analyzed and Tet-O-iPS, pLL-O-iPS and MEFS were used as controls. FIG. 7D shows the ethidium-bromide stained gel used for the southern blot.

FIGS. 8A-B show the numbers of GFP-positive (FIG. 8A) and CiPSC (FIG. 8B) colonies induced by removing individual chemicals from VC6TFZ. The results of three independent experiments are shown with different colors (white, gray, and black).

FIG. 9A shows pluripotency marker expression in different clones of CiPS cells compared to MEFS, as illustrated by RT-PCR. FIG. 9B shows growth curves for CiPSCs. FIGS. 9B-D show RT-PCR analysis of pluripotency markers in MAF-CiPS cells, ADSC-CiPSC and MNF-CiPSCs.

FIGS. 11E-F shows the effects of individual and combined chemicals on the expression of Sall4 and Sox2 on day 12. FIG. 11G-H show the effects of removing chemicals from VC6TF on the expression of Sall4 and Sox2 on day 12. FIG. 11I shows the effects of withdrawing individual chemicals (CHIR, 616452 and FSK) from VC6TFZ on the expression of the pluripotency marker genes on day 32. FIG. 11K shows the expression of pluripotency-related genes in the presence and absence of DZNep on day 32. FIG. 11K shows H3K9 methylation in the presence and absence of DZNep on day 32.

FIGS. 12A-B shows relative expression levels of Sal4 (FIG. 12A) and Sox2 (FIG. 12B) in MEFs on day 4 post-transduction validated by real-time PCR. Error bars indicate the s.d (n=2).

FIGS. 13A-D show gene expression changes by the knockdown of Sall4, Gata6, Gata4 or Sox17 on day 24. FIG. 13A shows relative expression changes of Sall4, Gata6 and Gata4 by Sall4, Gata6 or Gata4 knockdown. FIG. 13B shows relative expression changes of Sox17, Sall4, Gata6, Gata4 and Oct4 by Sox17 knockdown. FIG. 13C shows relative expression changes of Sox17 by the knockdown of Sall4, Gata6 or Gata4. FIG. 13D shows relative expression changes of Sox2 by the knockdown of Sall4, Gata6 or Gata4. Error bars indicate the s.d. (n=2). FIGS. 13E-F show the effects of Sall4, Gata6 or Gata4 knockdown on the expression of Oct4 and iPSCs formation. FIG. 13E shows Oct4 expression change by Sall4, Gata6 or Gata4 knockdown on day 32. Error bars indicate the s.d. (n=2). FIG. 13F shows numbers of GFP-positive and iPSC colonies when Sall4, Gata6 or Gata4 was knockdown during chemical reprogramming. Error bars indicate the s.d. (n=3).

FIGS. 14A-B show biological activity of DZNep during chemical reprogramming. FIG. 14A shows the relative ratios of intracellular levels SAH to SAM compared to that in MEFs as measured by HPLC analysis. Error bars indicate the s.d. (n=2). FIG. 14B shows the use of replacement of DZNep by SAH hydrolase inhibitors (Nep A, Adox and DZA) in combination with VC6TF treatment to induce CiPSC generation. Error bars indicate the s.d. (n=3). Abbreviations: HPLC (high-performance liquid chromatography). FIG. 14C shows protein levels of EZH2 were analyzed by western blot analysis. FIG. 14D shows numbers of iPSC colonies induced by VC6TF plus shRNA or DZNep. Error bars indicate the s.d. (n=3). FIG. 14E shows real-time PCR showing that Ezh2 was repressed following shRNA-mediated knockdown of Ezh2. Error bars indicate the s.d. (n=2).

DETAILED DESCRIPTION OF THE INVENTION

I. Definitions

Figure 1A:
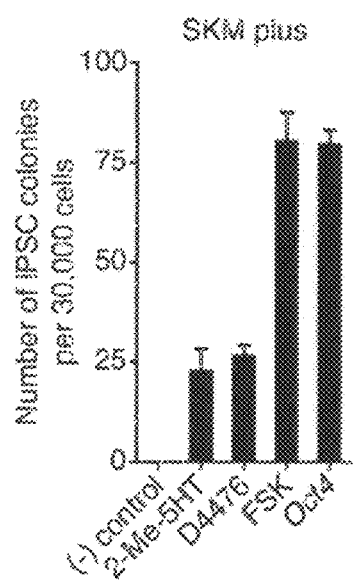
FIGS. 1A and 1B show the numbers of iPSC colonies induced from MEFs infected by SKM (FIG. 1A) or SK (FIG. 1B) plus chemicals or Oct4. Error bars, mean±SD (n=3 biological repeat wells.
Figure 1C:
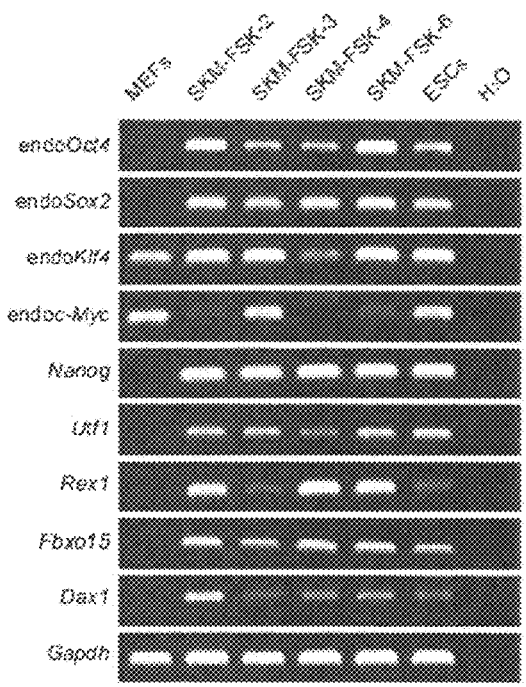
FIG. 1C shows RT-PCR analysis of pluripotency marker genes in MEFs, SKM-FSK-iPSCs and ESCs (R1).

The term "chemically induced pluripotent stem cells" (CiPSCs) as used herein refers to pluripotent cells derived from a cell that is not pluripotent, i.e., a multipotent or differentiated cells, by contacting the non-pluripotent cell with chemical compounds, not by expression of one or more transfected genes.

As used herein a "culture" means a population of cells grown in a medium and optionally passaged. A cell culture may be a primary culture (e.g., a culture that has not been passaged) or may be a secondary or subsequent culture (e.g., a population of cells which have been subcultured or passaged one or more times).

The term "epigenetics" as used herein refers to covalent modifications of DNA that are not mutation based, but in some instances can still be passed from generation to generation. Genes that are activated or repressed without any change in DNA sequence are epigenetically controlled. Epigenetic modifications are stable, but potentially reversible alterations in gene expression that occur without permanent changes in DNA sequence. Many types of epigenetic processes have been identified—they include methylation, acetylation, phosphorylation, ubiquitylation, and sumolyation of histones as well as DNA methylation.

The term "epigenetic modulators" as used herein refers to an agent, which modulates epigenetic processes. Histone deacetylase (HDAC) inhibitors and inhibitors of DNA methylation are examples of epigenetic modulators.

The term "glycogen synthase kinase (GSK) inhibitor" as used herein refers to an agent that inhibits a GSK. GSK include GSK 1, GSK 2 and GSK 3.

The term "an agent which promotes histone acetylation" as used herein includes inhibitors of histone deacetylation or histone acetylators.

The term "inhibitor of histone deacetylation" as used herein refers to an agent which prevents the removal of acetyl groups from lysine residues on histones.

The term "Induced pluripotent stem cell" (iPSC), as used herein, is a type of pluripotent stem cell artificially derived from a non-pluripotent cell. CiPSCs are iPSCs; however, they differ from some iPSCs in that they are not genetically engineered.

The term "isolated" or "purified" when referring to CiPSCs means chemically induced pluripotent stem cells at least 30%, 35%, 40%, 45%, 50%, 55%, 60%, 65%, 70%, 75%, 80%, 85%, 90%, 95%, or 99% free of contaminating cell types such as non-pluripotent cells. The isolated stem cells may also be substantially free of soluble, naturally occurring molecules.

The term "pluripotency" (or pluripotent), as used herein refers to a stem cell that has the potential to differentiate into any of the three germ layers: endoderm (for example, interior stomach lining, gastrointestinal tract, the lungs), mesoderm (for example, muscle, bone, blood, urogenital), or ectoderm (for example, epidermal tissues and nervous system). The term "not pluripotent" means that the cell does not have the potential to differentiate into all of the three germ layers. A multipotent stem cell is less plastic and more differentiated, and can become one of several types of cells within a given organ. For example, multipotent blood stem cells can develop into red blood cell progenitors, white blood cells or platelet producing cells. Adult stem cells are multipotent stem cells. Adipose-derived stem cells are multipotent.

"Reprogramming" as used herein refers to the conversion of a one specific cell type to another. For example, a cell that is not pluripotent can be reprogrammed into a pluripotent cell. Where the non-pluripotent cell is reprogrammed into a pluripotent cell using chemical compounds, the resulting cell is a chemically induced pluripotent stem cell.

"Reprogramming medium" as used herein refers to cell culture medium that includes one or more chemical inducers of pluripotency.

"S-adenosylhomocysteine hydrolase (SAH) inhibitor" as used herein refers to an agent that inhibits SAH. SAH is an enzyme of the activated methyl cycle, responsible for the reversible hydration of S-adenosyl-L-homocysteine into adenosine and homocysteine "2i medium" as use herein refers to ESC culture medium with dual inhibition of glycogen synthase kinase-3 and mitogen-activated protein kinase signaling, for example, ESC culture medium supplemented with 2i (CHIR99021 and PD0325901). The term "small molecule" refers to a molecule, such as an organic or organometallic compound, with a molecular weight of less than 2,000 Daltons, more preferably less than 1,500 Daltons, most preferably less than 1,000 Daltons.

"Transforming growth factor beta (TGFβ) receptor inhibitor as used herein refers to an agent that inhibits the TGFβ receptor. TGFβ receptors are single pass serine/threonine kinase receptors. Three TGF-β receptor types include receptor types I, II and III i.e., TGF-β receptor 1, TGF-β receptor 2 and TGF-β receptor 3.

II. Compositions

A. Small Molecules Inducing Pluripotency

Chemical compounds that induce pluripotency i.e., chemical inducers of pluripotency (CIP) include small molecules having a molecular weight of less than 2,000 Daltons, more preferably less than 1,500 Daltons, most preferably less than 1,000 Dalton, alone or in combination with proteins. The small molecules may have a molecular weight less than or equal to 900 Daltons or, less than or equal to 500 Daltons. Larger molecules can be used in chemically-induced reprogramming, preferably targeting the same pathway as the small molecules identified here. Several protein factors, such as recombinant bFGF, have been demonstrated to be effective in the following protocol for chemical reprogramming.

Small molecules have been identified which can be used to reprogram partially or completely differentiated cells into pluripotent cells. The required chemical inducers of pluripotency (CIPs) include (1) a glycogen synthase kinase (GSK) inhibitor, (2) a TGFβ receptor inhibitor, (3) a cyclic AMP agonist, (4) a S-adenosylhomocysteine hydrolase (SAH) inhibitor, (5) an agent which promotes histone acetylation, such as a histone deacetylase (HDAC) inhibitor, and combinations thereof. The CIPs may be provided separately or in combination as a CIP composition. One or more epigenetic factors and retinoic acid receptor agonists may also be administered with the CIPs.

In a preferred embodiment, the GSK inhibitor is a glycogen synthase kinase 3 inhibitor, for example, the aminopyrimidine, CHIR99021 having the chemical name [6-[[2-[[4-(2,4-Dichlorophenyl)-5-(5-methyl-1H-imidazol-2-yl)-2-pyrimidinyl]amino]ethyl]amino]-3-pyridinecarbonitrile] ("CHIR"); the TGFβ receptor inhibitor is a TGFβ receptor type 1 inhibitor, for example, [2-(3-(6-Methylpyridin-2-yl)-1H-pyrazol-4-yl)-1,5-naphthyridine] (616452); the cAMP agonist is Forskolin (FSK) and the SAH inhibitor is 3-deazaneplanocin A (DZNep).

In some embodiments, the CIPs are a combination of CHIR, 616452, FSK and DZNep (C6FZ). In a more preferred embodiment, the CIPs are a combination of VPA, CHIR, 616452, tranylcypromine, FSK (collectively, VC6TF) and DZNep (collectively, VC6TFZ).

In the preferred embodiment, the SAH inhibitor is 3-deazaneplanocin A (DZNep). Other useful SAH hydrolase inhibitors that can be included in the CIP combination compositions disclosed herein include, but are not limited to, (−) Neplanocin A (Nep A), Adenozine periodate (oxidized) Adox and 3-deazaadenosine (DZA) and combinations thereof.

Suitable agents which promote histone acetylation include HDAC inhibitors. Examples of HDAC inhibitors include hydroxamic acids such as trichostatin (A), cyclic tetrapeptides, benzamides, electrophilic ketones, sodium butyrate and compounds such as phenylbutyrate and valporic acid (VPA). A preferred HDAC inhibitor is VPA.

In a preferred embodiment, epigenetic modulators that can be included in the CIP composition include agents that inhibit DNA methylation, for example, one or more of 5-azacytidine RG108 and combinations thereof.

In some embodiments, small molecules that facilitate late reprogramming and small molecules that improve/boost chemical reprogramming efficiency over the levels seen with VC6TFZ are included. Improved/boosted efficiency can be manifested by reducing the time needed to generate such pluripotent cells (e.g., by shortening the time to development of pluripotent cells by at least a day compared to a similar or same process without the small molecule). Alternatively, or in combination, a small molecule can increase the number of pluripotent cells generated by a particular process (e.g., increasing the number in a given time period by at least 10%, 50%, 100%, 200%, 500%, etc. compared to a similar or same process without the small molecule).

Small molecules that facilitate late reprogramming include cAMP agonists (for example, prostaglandin E2 (PGE2), FSK and rolipram) and epigenetic modulators (for example, 5-azacytidine, sodium butyrate and RG108).

Small molecules that improve/boost chemical reprogramming efficiency include prostaglandin E2 (PGE2), [N-(9,10-dioxo-9,10-dihydrophenanthren-2-yl)pivalamide] (SF1670), [N-(4-(Diethylaminobenzylidenyl)-N'-(4-hydroxybenzoyl)-hydrazine] (DY131 DY131), [2-Cyclohexyl-6-methoxy-N-[1-(1-methylethyl)-4-piperidinyl]-7-[3-(1-pyrrolidinyl)propoxy]-4-quinazolinamine] (UNC0638), [N-(2-(3-(piperazin-1-ylmethyl)imidazo[2,1-b]thiazol-6-yl) phenyl)quinoxaline-2-carboxamide hydrochloride] (SRT1720), [N-Phthalyl-L-tryptophan] (RG108), 2-Me-5HT (2-methyl-5-hydroxytryptamine), [3,7-Dihydro-1-methyl-3-(2-methylpropyl)-1H-purine-2,6-dioneand] (IBMX) and [4-[(E)-2-(5,6,7,8-Tetrahydro-5,5,8,8-tetramethyl-2-naphthalenyl)-1-propenyl]benzoic acid] (TTNPB). A preferred small molecule for boosting chemical reprogramming efficiency is TTNPB.

Additional molecules that can be included in the compositions that induce pluripotency include D4476 (D4476 (CAS 301836-43-1), a high purity Casein kinase inhibitor); Ch 55 ([4-[(1E)-3-[3,5-bis(1,1-Dimethylethyl)phenyl]-3-oxo-1-propenyl]benzoic acid], a highly potent synthetic retinoid that has high affinity for RAR-α and RAR-β receptors and low affinity for cellular retinoic acid binding protein (CRABP)]; AM580 ([4-[(5,6,7,8-Tetrahydro-5,5,8,8-tetramethyl-2-naphthalenyl)carboxamido]benzoic acid]; an analog of retinoic acid that acts as a selective RARα agonist); and EPZ004777, "1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea (EPZ).

An example of small molecule combinations that can be used to reprogram cells is shown in Table 1A

TABLE 1A small molecule combination for inducing pluripotency

| small molecule combination that can induce pluripotency | Initial cell numbers | CiPSC colony number that were induced |
|---|---|---|
| CHIR99021 + 616452 + Forskolin | 100,000 | 1 |
| CHIR99021 + 616452 + Forskolin + DZNep | 50,000 | 3 |
| CHIR99021 + 616452 + Forskolin + DZNep + VPA | 40,000 | 8 |
| CHIR99021 + 616452 + Forskolin + DZNep + TTNPB | 28,000 | 42 |
| CHIR99021 + 616452 + Forskolin + DZNep + Tranylcypromine | 90,000 | 1 |
| CHIR99021 + 616452 + Forskolin + VPA + Tranylcypromine | 50,000 | 1 |
| CHIR99021 + 616452 + DZNep + VPA + Tranylcypromine | 300,000 | 1 |
| CHIR99021 + 616452 + Forskolin + DZNep + 4PB + Tranylcypromine | 20,000 | 2 |
| CHIR99021 + 616452 + Forskolin + DZNep + VPA + Tranylcypromine | 40,000 | 12 |
| CHIR99021 + 616452 + DBcAMP + DZNep + VPA + Tranylcypromine | 40,000 | 1 |
| CHIR99021 + 616452 + IBMX + DZNep + VPA + Tranylcypromine | 40,000 | 1 |
| CHIR99021 + 616452 + Rolipram + DZNep + VPA + Tranylcypromine | 40,000 | 1 |
| CHIR99021 + 616452 + Forskolin + NepA + VPA + Tranylcypromine | 50,000 | 32 |
| CHIR99021 + 616452 + Forskolin + Adox + VPA + Tranylcypromine | 50,000 | 28 |
| CHIR99021 + 616452 + Forskolin + DZA + VPA + Tranylcypromine | 50,000 | 10 |
| CHIR99021 + 616452 + Forskolin + Decitabine + EPZ + VPA + Tranylcypromine | 30,000 | 14 |
| CHIR99021 + 616452 + Forskolin + DZNep + VPA + Tranylcypromine + TTNPB | 40,000 | 20 |
| CHIR99021 + 616452 + Forskolin + DZNep + VPA + Tranylcypromine + AM580 | 40,000 | 25 |
| CHIR99021 + 616452 + Forskolin + DZNep + VPA + Tranylcypromine + Ch55 | 40,000 | 19 |
| TD114-2 + 616452 + Forskolin + DZNep + VPA + Tranylcypromine | 40,000 | 40 |
| CHIR99021 + 616452 + Forskolin + VPA + Tranylcypromine + 2M5 + D4476 + Butyrate + UNC0638 + Scriptaid | 300,000 | 6 |
| CHIR99021 + 616452 + Forskolin + VPA + Tranylcypromine + TTNPB + PGE2 + 5-aza-C | 250,000 | 5 |
| CHIR99021 + 616452 + Forskolin + VPA + Tranylcypromine + TTNPB + PGE2 + Decitabine | 250,000 | 8 |
| CHIR99021 + 616452 + Forskolin + VPA + Tranylcypromine + Decitabine + EPZ | 30.000 | 14 |

Concentration ranges for exemplary small molecules that can be included in the formulations disclosed herein are provided in Table 1B.

TABLE 1B summary of small molecule concentrations

| Chemical names | Concentration ranges | preferred concentrations |
|---|---|---|
| CHIR99021 | 0.1-40 | 10 |
| 616452 | 0.1-50 | 10 |

TABLE 1B-continued summary of small molecule concentrations

| Chemical names | Concentration ranges | preferred concentrations |
|---|---|---|
| Forskolin | 0.1-100 | 10 |
| DZNep | 0.005-0.5 | 0.05 |
| VPA | 50-2000 | 500 |
| TTNPB | 0.01-5 | 2 |
| Tranylcypromine | 1-40 | 5 |
| 4PB | 0.1-50 | 2 |
| DBcAMP | 0.1-500 | 50 |
| IBMX | 0.1-500 | 50 |
| Rolipram | 0.1-50 | 10 |
| NepA | 0.01-5 | 0.05 |
| Adox | 0.1-50 | 10 |
| DZA | 0.1-50 | 10 |
| Decitabine | 0.01-5 | 0.1 |
| EPZ | 0.1-20 | 5 |
| AM580 | 0.01-5 | 0.05 |
| Ch55 | 0.01-5 | 2 |
| TD114-2 | 0.1-20 | 2 |
| 2M5 | 0.1-40 | 5 |
| D4476 | 0.1-40 | 5 |
| Butyrate | 1-400 | 200 |
| UNC0638 | 0.01-5 | 0.5 |
| Scriptaid | 0.01-5 | 0.5 |
| PGE2 | 0.1-20 | 5 |
| 5-aza-C | 0.01-50 | 5 |
| RG108 | 0.01-100 | 10 |
| SRT1720 | 0.1-20 | 2 |

B. Protein Factors

Protein factors, such as recombinant basic fibroblast growth factor (bFGF), have been demonstrated to be effective in the following protocol for chemical reprogramming. bFGF can be used in a concentration range from 10 ng/mL-200 ng/mL, preferably at concentration of 100 ng/mL.

C. Cells to be Induced

The induced pluripotent stem cells are obtained by inducing partially or completely differentiated cells obtained from a mammal such as any mammal (e.g., bovine, ovine, porcine, canine, feline, equine, primate), preferably a human. Sources include bone marrow, fibroblasts, fetal tissue (e.g., fetal liver tissue), peripheral blood, umbilical cord blood, pancreas, skin or any organ or tissue. In a preferred embodiment, the CiPSCs are obtained from chemically induced fibroblasts, adipose-derived stem cells, neural stem cells or cells from the intestinal epithelium. In a more preferred embodiment, CiPSCs are obtained from chemically induced neonatal (for example foreskin) or adult fibroblasts. However, CiPSCs can be obtained from other cell types including but not limited to: multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells. multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells. The cell to be reprogrammed can be obtained from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, pancreas, skin or any organ or tissue.

In a preferred embodiment, the CiPSCs are obtained from fibroblasts and adipose-derived stem cells. In a more preferred embodiment, CiPSCs are obtained from fibroblast, which can be neonatal (for example foreskin fibroblasts) or adult fibroblast. In still another preferred embodiment, the non-pluripotent cells do not express Oct4 and/or are not genetically engineered to express one or more markers of pluripotency.

Cells may be isolated by disaggregating an appropriate organ or tissue which is to serve as the cell source using techniques known to those skilled in the art. For example, the tissue or organ can be disaggregated mechanically and/or treated with digestive enzymes and/or chelating agents that weaken the connections between neighboring cells, so that the tissue can be dispersed to form a suspension of individual cells without appreciable cell breakage. Enzymatic dissociation can be accomplished by mincing the tissue and treating the minced tissue with one or more enzymes such as trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators.

D. Chemically Induced Pluripotent Stem Cells (CiPSCs)

CiPSCs are physiologically and morphologically indistinguishable from Embryonic Stem Cells (ESC). The Examples show that CiPSCs grow with a doubling time similar to ESC, and like ESC, express pluripotency markers, have a similar gene expression profile to ESC, and have a similar DNA methylation and histone modifications at Oct4 and Nanog promoters. Karyotyping analysis also demonstrates that CiPSCs do not acquire chromosomal abnormalities. Further evidence that the CiPSCs are pluripotent is their ability to differentiate into tissues of the three embryonic germ layers. These findings demonstrate the ability to manipulate differentiated human cells to generate an unlimited supply of patient-specific pluripotent stem cells.

CiPSCs possess ESC-like properties such as ESC morphology, doubling time similar to ESC, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. Such cells can also be characterized by the down-regulation of markers characteristic of the differentiated cell from which the CiPSC is induced. For example, CiPSCs derived from fibroblasts may be characterized by down-regulation of the fibroblast cell marker Thy1 and/or up-regulation of SSEA-1. There is no minimum number of pluripotency markers that must be displayed on CiPSCs. The gold standard for pluripotency is the differentiation potential into cell types of all three germ layers. Teratoma assay, chimeras assay and the germ-line transmission capability are some direct assays to test their differentiation potential.

III. Methods of Making

A. Induction of CiPSCs

CiPSCs are induced by providing partially or completely differentiated cells in a culture media containing the CIPs for a sufficient period of time to result in reprogramming the cells into chemically induced pluripotent stem cell (CiPSC). The reprogrammed cells are defined as pluripotent cells based on possession of ESC-like properties such as morphology, doubling time, expression of ESC markers for example alkaline phosphatase (AP); nanog, Rex1; Sox2; Dax1; Sall4; undifferentiated embryonic cell transcription factor (Utf1); stage specific embryonic antigen-4 (SSEA-4), and the ability of the cell to differentiate into tissues of the three embryonic germ layers.

The CIP compounds are contacted with the cells to be induced in an amount effective to induce and/or enhance reprogramming of non-pluripotent cells into pluripotent cells. One of skill in the art can readily determine the concentrations of the CIP compounds disclosed herein required to provide complete reprogramming using methods outlined in the examples below, or other methods known in the art. In some preferred embodiments, the CIPs include an SAH inhibitor.

In some embodiments, VPA is administered to the cells to a concentration between 500 μM and 0.5 mM, CHIR is administered to a concentration between 10 to 20 μM, 616452 is administered to a concentration between 5 to 10 μM, FSK is administered to a concentration between 10 to 50 μM and DZNep is administered to a concentration between 20 nM and 0.1 μM, preferably, between 0.05 to 0.1 μM, and more preferably, between 20 and 200 nM. Exemplary combinations of small molecules that can be used to induce pluripotency in a non-pluripotent cell and concentration ranges are provided in Tables 1A and B.

616452 and Forskolin need to be present the entire time before the use of 2i-medium. CHIR99021 should be used in the first 12 days, and is preferably present the entire time before the use of 2i-medium. DZNep should be added at the late stage of reprogramming (day 12 to day 40), preferably, day 20 after the initial treatment of other small molecules. The small molecule combination (VC6TFZ) should be changed into 2i-medium after a time point between day 28 and day 48, preferably day 40. Different cell types have different optimal concentrations of small molecules. These can be determined by routine experimentation based on the studies described herein. The order of exposure and the period of time of exposure are similar between cell types.

In a preferred embodiment, the method includes culturing cells in a reprogramming medium containing the CIPs for a period between 26-36 days, and further culturing the cells in an ESC culture medium for about 4 days with dual inhibition of glycogen synthase kinase-3 (GSK3) and mitogen-activated protein kinase (MAPK) signaling after about day 28 post treatment with the reprogramming medium. In one embodiment, dual inhibition of GSK3 and MAPK is accomplished using CHIR99021 and PD0325901.

The cells are cultured in reprogramming medium preferably containing the CIP components VC6TF for about 16-20 days, and medium containing VC6TFZ for the remaining period of time during which the cells are exposed to the reprogramming medium. In some embodiments, the method further includes contacting the cells with small molecules that facilitate late reprogramming for example, cAMP agonists other than forskolin and/or epigenetic modulators disclosed herein, and/or small molecules that improve/boost chemical reprogramming efficiency disclosed herein. Epigenetic modulators can be included in the composition containing VC6TF. Alternatively, these small molecules can be included in cell culture medium following treatment of the cells with VC6TF. The cells are preferably exposed to the small molecules for more than 1 day. In some embodiments, treatment of cells with cAMP agonists and epigenetic modulators does not exceed the period of treatment with VC6TF. In other embodiments treatment of cells with cAMP agonists and epigenetic modulators does not exceed the period of treatment with VC6TFZ. In still other embodiments, treatment of cells with cAMP agonists and epigenetic modulators does not exceed the period of treatment with VC6TF plus VC6TFZ. A preferred small molecule for boosting chemical reprogramming efficiency is TTNPB.

The disclosed methods yield induced pluripotent stem cells without the need to transfect cells with genes such as Oct4, KLF4, SOX2, C-Myc or NANOG or the need to contact the cells with any of the KLF, Oct, Myc and/or Sox polypeptide.

B. Isolation of CiPSCs

Media that can maintain the undifferentiated state and pluripotency of ES cells or induce differentiation are known in this field. Differentiation and proliferation abilities of isolated induced pluripotent stem cells can be easily confirmed by those skilled in the art by using confirmation means widely applied to ES cells.

A substantially purified population of CiPSCs can be obtained, for example, by extraction (e.g., via density gradient centrifugation and/or flow cytometry) from a culture source. Purity can be measured by any appropriate method. The pluripotent cells can be 99%-100% purified by, for example, flow cytometry (e.g., FACS analysis). Human induced pluripotent stem cells can be isolated by, for example, utilizing molecules (e.g., antibodies, antibody derivatives, ligands or Fc-peptide fusion molecules) that bind to a marker (e.g., a TRA-1-81, a TRA-1-61 or a combination of markers) on the induced pluripotent stem cells and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Antibodies may be conjugated with markers, such as magnetic beads, which allow for direct separation, biotin, which can be removed with avidin or streptavidin bound to a support, or fluorochromes, which can be used with a fluorescence activated cell sorter, to allow for ease of separation of the particular cell type. Any technique may be employed which is not unduly detrimental to the viability of the induced pluripotent stem cells. In one embodiment, the cells are incubated with an antibody against a marker (e.g., a TRA-1-81 antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest, the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, and Texas red.

Any cell type-specific markers can be used to select for or against a particular cell type. Induced stem cell markers useful for enrichment comprise expressed markers such as TRA-1-81 and loss of markers (e.g., GFP) associated with a retroviral vector or other exogenous vector.

C. Culture and Preservation of CiPSCs (and their Progeny)

The CiPSCs can be expanded in culture and stored for later retrieval and use. Once a culture of cells or a mixed culture of stem cells is established, the population of cells is mitotically expanded in vitro by passage to fresh medium as cell density dictates under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor). Cultured cells can be transferred to fresh medium when sufficient cell density is reached. Some stem cell types do not demonstrate typical contact inhibition-apoptosis or they become quiescent when density is maximum. Accordingly, appropriate passaging techniques can be used to reduce contact inhibition and quiescence.

Cells can be cryopreserved for storage according to known methods, such as those described in Doyle et al., (eds.), 1995, Cell & Tissue Culture: Laboratory Procedures, John Wiley & Sons, Chichester. For example, cells may be suspended in a "freeze medium" such as culture medium containing 15-20% fetal bovine serum (FBS) and 10% dimethylsulfoxide (DMSO), with or without 5-10% glycerol, at a density, for example, of about $4\text{-}10\times10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

IV. Methods of Use

Identification of a readily available source of stem cells that can give rise to a desired cell type or morphology is important for therapeutic treatments, tissue engineering and research. The availability of stem cells would be extremely useful in transplantation, tissue engineering, regulation of angiogenesis, vasculogenesis, and cell replacement or cell therapies as well as the prevention of certain diseases. Such stem cells can also be used to introduce a gene into a subject as part of a gene therapy regimen.

A. Providing Differentiated Somatic Cells (Re-Differentiated Cells)

Once established, a culture of stem cells may be used to produce progeny cells, for example, fibroblasts capable of producing new tissue. The CiPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells, blood cells, retinal cells (and other cells involved in sensory perception, such as those that form hair cells in the ear or taste buds on the tongue), and nervous tissue including nerves.

In one embodiment, the CiPSCs are induced to differentiate into cells of ectodermal origin by exposing the cells to an "ectodermal differentiating" media. In another embodiment the CiPSCs are induced to differentiate into cells of mesodermal origin by exposing the cells to "mesodermal differentiating media". In still another embodiment, the CiPSCs are induced to differentiate into cells of endodermal origin by exposing the cells to "endodermal media". Components of "endodermal", "mesodermal" and "ectodermal" media are known to one of skill in the art. Known cell surface markers can be used to verify that the cells are indeed differentiating into cells of the lineage of the corresponding cell culture medium. The most commonly accepted markers to confirm differentiation of the three germ layers are the expression of alpha fetal protein for endodermal cells, alpha smooth muscle actin for mesoderm, and Beta-III tubulin for ectoderm, all of which are normally expressed very early in the development of these tissues.

Differentiation of stem cells to fibroblasts or other cell types, followed by the production of tissue therefrom, can be triggered by specific exogenous growth factors or by changing the culture conditions (e.g., the density) of a stem cell culture. Methods for inducing differentiation of cells into a cell of a desired cell type are known in the art. For example, CiPSCs can be induced to differentiate by adding a substance (e.g., a growth factor, enzyme, hormone, or other signaling molecule) to the cell's environment. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, Leukemia Inhibitory Factory (LIF), or Steel Factor (St1), coculture with tissue committed cells, or other lineage committed cells types to induce the stem cells into becoming committed to a particular lineage.

The redifferentiated cells can be can be expanded in culture and stored for later retrieval and use.

B. Cell Therapy

Therapeutic uses of the induced pluripotent stem cells include transplanting the induced pluripotent stem cells, stem cell populations, or progeny thereof into individuals to treat a variety of pathological states including diseases and disorders resulting from cancers, wounds, neoplasms, injury, viral infections, diabetes and the like. Treatment may entail the use of the cells to produce new tissue, and the use of the tissue thus produced, according to any method presently known in the art or to be developed in the future. The cells may be implanted, injected or otherwise administered directly to the site of tissue damage so that they will produce new tissue in vivo. In one embodiment, administration includes the administration of genetically modified CiPSCs or their progeny.

In a preferred embodiment, the CiPSCs are obtained from autologous cells i.e., the donor cells are autologous. However, the cells can be obtained from heterologous cells. In one embodiment, the donor cells are obtained from a donor genetically related to the recipient. In another embodiment, donor cells are obtained from a donor genetically un-related to the recipient.

If the human CiPSCs are derived from a heterologous (non-autologous/allogenic) source compared to the recipient subject, concomitant immunosuppression therapy is typically administered, e.g., administration of the immunosuppressive agent cyclosporine or FK506. However, due to the immature state of the human induced pluripotent stem cells such immunosuppressive therapy may not be required. Accordingly, in one embodiment, the human induced pluripotent stem cells can be administered to a recipient in the absence of immunomodulatory (e.g., immunsuppressive) therapy. Alternatively, the cells can be encapsulated in a membrane, which permits exchange of fluids but prevents cell/cell contact. Transplantation of microencapsulated cells is known in the art, e.g., Balladur et al., *Surgery*, 117:189-94, 1995; and Dixit et al., Cell Transplantation 1:275-79 (1992).

(i) Diabetes

Diabetes mellitus (DM) is a group of metabolic diseases where the subject has high blood sugar, either because the pancreas does not produce enough insulin, or, because cells do not respond to insulin that is produced. A promising replacement for insulin therapy is provision of islet cells to the patient in need of insulin. Shapiro et al., *N Engl J Med.*, 343(4):230-8 (2000) have demonstrated that transplantation of beta cells/islets provides therapy for patients with diabetes. Although numerous insulin types are commercially available, these formulations are provided as injectables. The human induced pluripotent stem cells provide an alternative source of islet cells to prevent or treat diabetes. For example, induced pluripotent stem cells can be isolated and differentiated to a pancreatic cell type and delivered to a subject. Alternatively, the induced pluripotent stem cells can be delivered to the pancreas of the subject and differentiated to islet cells in vivo. Accordingly, the cells are useful for transplantation in order to prevent or treat the occurrence of diabetes. Methods for reducing inflammation after cytokine exposure without affecting the viability and potency of pancreatic islet cells are disclosed for example in U.S. Pat. No. 8,637,494 to Naziruddin, et al.

(ii) Neurodegenerative Disorders

Neurodegenerative disorders are characterized by conditions involving the deterioration of neurons as a result of disease, hereditary conditions or injury, such as traumatic or ischemic spinal cord or brain injury. Neurodegenerative conditions include any disease or disorder or symptoms or causes or effects thereof involving the damage or deterioration of neurons. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes Dorsalis or any other condition associated with damaged neurons. Other neurodegenerative conditions can include or be caused by traumatic spinal cord injury, ischemic spinal cord injury, stroke, traumatic brain injury, and hereditary conditions.

In particular, the disclosed methods include transplanting into a subject in need thereof NSCs, neural progenitors, or neural precursors that have been expanded in vitro such that the cells can ameliorate the neurodegenerative condition. Transplantation of the expanded neural stem cells can be used to improve ambulatory function in a subject suffering from various forms of myelopathy with symptoms of spasticity, rigidity, seizures, paralysis or any other hyperactivity of muscles. Methods for expanding and transplanting neural cells and neural progenitor cells for the treatment of different neurodegenerative conditions is disclosed for example, in U.S. Pat. No. 8,236,299 to Johe, et. al.

(iii) Cancer Therapy

Therapeutic uses of the CiPSCs and their progeny include transplanting the induced pluripotent stem cells, stem cell populations, or progeny thereof into individuals to treat and/or ameliorate the symptoms associated with cancer. For example, in one embodiment, the CiPSCs can be administered to cancer patients who have undergone chemotherapy that has killed, reduced, or damaged cells of a subject. In a typical stem cell transplant for cancer, very high doses of chemotherapy are used, often along with radiation therapy, to try to destroy all the cancer cells. This treatment also kills the stem cells in the bone marrow. Soon after treatment, stem cells are given to replace those that were destroyed.

In another embodiment, the CiPSCs can be transfected or transformed (in addition to the de-differentiation factors) with at least one additional therapeutic factor. For example, once CiPSCs are isolated, the cells may be transformed with a polynucleotide encoding a therapeutic polypeptide and then implanted or administered to a subject, or may be differentiated to a desired cell type and implanted and delivered to the subject. Under such conditions the polynucleotide is expressed within the subject for delivery of the polypeptide product.

(iii) Tissue Engineering

CiPSCs and their progeny can be used to make tissue engineered constructions, using methods known in the art. Tissue engineered constructs may be used for a variety of purposes including as prosthetic devices for the repair or replacement of damaged organs or tissues. They may also serve as in vivo delivery systems for proteins or other molecules secreted by the cells of the construct or as drug delivery systems in general. Tissue engineered constructs also find use as in vitro models of tissue function or as models for testing the effects of various treatments or pharmaceuticals. The most commonly used biomaterial scaffolds for transplantation of stem cells are reviewed in the most commonly used biomaterial scaffolds for transplantation of stem cells is reviewed in Willerth, S. M. and Sakiyama-Elbert, S. E., *Combining stem cells and biomaterial scaffolds for constructing tissues and cell delivery* (Jul. 9, 2008), StemBook, ed. The Stem Cell Research Community, StemBook. Tissue engineering technology frequently involves selection of an appropriate culture substrate to sustain and promote tissue growth. In general, these substrates should be three-dimensional and should be processable to form scaffolds of a desired shape for the tissue of interest.

U.S. Pat. No. 6,962,814 generally discloses method for producing tissue engineered constructs and engineered native tissue. With respect to specific examples, U.S. Pat. No. 7,914,579 to Vacanti, et al., discloses tissue engineered ligaments and tendons. U.S. Pat. No. 5,716,404 discloses methods and compositions for reconstruction or augmentation of breast tissue using dissociated muscle cells implanted in combination with a polymeric matrix. U.S. Pat. No. 8,728,495 discloses repair of cartilage using autologous dermal fibroblasts. U.S. Published application No. 20090029322 by Duailibi, et al., discloses the use of stem cells to form dental tissue for use in making tooth substitute. U.S. Published application No. 2006/0019326 discloses cell-seed tissue-engineered polymers for treatment of intracranial aneurysms. U.S. Published application No. 2007/0059293 by Atala discloses the tissue-engineered constructs (and method for making such constructs) that can be used to replace damaged organs for example kidney, heart, liver, spleen, pancreas, bladder, ureter and urethra.

(ii) Cells Produced from CiPSCs (Progeny)

The CiPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells (e.g., alpha cells, delta cells, PP cells, and beta cells), blood cells (e.g., leukocytes, erythrocytes, macrophages, and lymphocytes), retinal cells (and other cells involved in sensory perception, such as those that form hair cells in the ear or taste buds on the tongue), and nervous tissue including nerves.

(iii) Therapeutic Compositions

The CiPSCs can be formulated for administration, delivery or contacting with a subject, tissue or cell to promote de-differentiation in vivo or in vitro/ex vivo. Additional factors, such as growth factors, other factors that induce differentiation or dedifferentiation, secretion products, immunomodulators, anti-inflammatory agents, regression factors, biologically active compounds that promote innervation, vascularization or enhance the lymphatic network, and drugs, can be incorporated.

The induced pluripotent cells can be administered to a patient by way of a composition that includes a population of CiPSCs or CiPSC progeny alone or on or in a carrier or support structure. In many embodiments, no carrier will be required. The cells can be administered by injection onto or into the site where the cells are required. In these cases, the cells will typically have been washed to remove cell culture media and will be suspended in a physiological buffer.

In other embodiments, the cells are provided with or incorporated onto or into a support structure. Support structures may be meshes, solid supports, scaffolds, tubes, porous structures, and/or a hydrogel. The support structures may be biodegradable or non-biodegradable, in whole or in part. The support may be formed of a natural or synthetic polymer, metal such as titanium, bone or hydroxyapatite, or a ceramic. Natural polymers include collagen, hyaluronic acid, polysaccharides, and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters. These may be in for the form of implants, tubes, meshes, or hydrogels.

Solid Supports

The support structure may be a loose woven or non-woven mesh, where the cells are seeded in and onto the mesh. The structure may include solid structural supports. The support may be a tube, for example, a neural tube for regrowth of neural axons. The support may be a stent or valve. The support may be a joint prosthetic such as a knee or hip, or part thereof, that has a porous interface allowing ingrowth of cells and/or seeding of cells into the porous structure. Many other types of support structures are also possible. For example, the support structure can be formed from sponges, foams, corals, or biocompatible inorganic structures having internal pores, or mesh sheets of interwoven polymer fibers. These support structures can be prepared using known methods.

The support structure may be a permeable structure having pore-like cavities or interstices that shape and support the hydrogel-cell mixture. For example, the support structure can be a porous polymer mesh, a natural or synthetic sponge, or a support structure formed of metal or a material such as bone or hydroxyapatite. The porosity of the support structure should be such that nutrients can diffuse into the structure, thereby effectively reaching the cells inside, and waste products produced by the cells can diffuse out of the structure The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape. The support can be shaped either before or after the support structure is seeded with cells or is filled with a hydrogel-cell mixture, as described below.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape. Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Hydrogels

In another embodiment, the cells are mixed with a hydrogel to form a cell-hydrogel mixture. Hydrogels may be administered by injection or catheter, or at the time of implantation of other support structures. Crosslinking may occur prior to, during, or after administration.

V. KITS

Kits are provided which include the chemical inducers of pluripotency (CIP) disclosed herein. The CIPs are as described above. These may be in a form having defined concentrations to facilitate addition to cell culture media to produce a desired concentration. The kit may include directions providing desired concentration ranges and times of administration based on the types of cells to be induced. The kit may also include cell culture media which is pre-mixed with the CIPs for culture of cells to induce pluripotency.

The present invention will be further understood by reference to the following non-limiting examples.

EXAMPLES

Materials and Methods

Mice

The mouse strains C57BL/6J-Tg(GOFGFP)11Imeg/Rbrc (OG), C57BL/6NCrlVr (C57), ICR and 129S2/SvPasCrlVr (129) were purchased as described by Li, *Cell Res.*, 21:196-204 (2011). The OG mice were mated with other strains to generate offspring carrying Oct4 promoter-driven GFP. Mouse strains including ICR, C57 X 129, OG X ICR, OG X 129 and OG X C57 were used to isolate primary mouse embryonic fibroblasts (MEFs), mouse neonatal fibroblasts (MNFs), mouse adult fibroblasts (MAFs) and adipose-derived stem cells (ADSCs). These cells were used for CiPSC induction. The neonatal mice used were 2-3 days old and the adult mice used were 7 weeks old. The Tet-On POU5F1 mouse strain B6; 129t(ROSA)26Sortm1(rtTA*M2)Jae Col1a1tm2(tetO-Pou5f1)Jae/J was purchased from Jackson Laboratory (Hochedlinger, et al., *Cell*, 121:465-477 (2005)) and used only for reprogramming with Oct4 plus VC6T. Animal experiments were performed according to the Animal Protection Guidelines of Peking University, China.

Cell Culture

Primary MEFs were isolated as described by Takahashi, et al., *Cell*, 126:663-676 (2006)), with careful attention to the removal of the genital ridges. MNFs from skin, MAFs from lungs and ADSCs from inguinal fat pads were isolated as described by Lichti, et al., *Nat. Protoc.* 3:799-810 (2008); Seluanov, et al., *J. Vis. Exp.* 2010:2033 (2010); Tat, et al., *Cell Transplant.* 19:525-536 (2010) and McQualter, et al., *Stem Cells*, 27:623-633 (2009).

MEFs, MNFs, MAFs and ADSCs were cultured in DMEM/High Glucose (Hyclone) containing 10% fetal bovine serum (Hyclone). The cells used in reprogramming were from passages 1 to 5.

Mouse ESCs (R1 and TT2), iPSCs and CiPSCs were maintained on feeder layers of mitomycin C-treated MEFs in ESC culture medium (KnockOut DMEM (Invitrogen) containing 10% knockout serum replacement (Invitrogen), 10% fetal bovine serum (Hyclone), 2 mM GlutaMAX™-I (Invitrogen), 1% nonessential amino acids (Invitrogen), 0.1 mM 2-mercaptoethanol (Invitrogen), 1% penicillin-streptomycin (Invitrogen) and 1,000 U/ml leukemia inhibitory factor (LIF, Millipore)) or 2i-medium (ESC culture medium supplemented with 2i (3 μM CHIR99021 and 1 μM PD0325901)). The medium was changed daily. ESCs, iPSCs and CiPSCs were passaged by trypsin-EDTA (Invitrogen). For CiPSC induction, LIF-free ESC culture medium supplemented with 20-100 ng/ml bFGF (Origene) was used as the chemical reprogramming medium.

Small-molecule Compounds and Libraries

The small-molecule compounds used in this study were purchased or synthesized as described in Table 1D. The concentration of each compound is shown in Table 1D. The small-molecule libraries used for the screen were purchased or generated in-house as described in Table 1C

TABLE 1C

Small molecule libraries used in reprograming

| Library | Source | Number of small-molecule compounds |
|---|---|---|
| BBP-2080NPs library | BioBioPha | 2,080 |
| The Spectrum Collection | MicroSource Discovery Systems | 2,000 |
| Sigma LOPAC ®[1280] | Sigma | 1,280 |
| Prestwick Chemical Library ® | Prestwick Chemical | 1,200 |
| Tocriscreen ™ Total | Tocris | 1,120 |
| US Drug Collection | MicroSource Discovery Systems | 1,040 |
| ICCB Known Bioactives Library | Enzo | 480 |
| Protein Kinase Inhibitor Library I, II, III | Millipore | 324 |
| StemSelect Small Molecule Regulators | Calbiochem | 303 |
| Nuclear Receptor Ligand Library | Enzo | 76 |
| Selected Small Molecules* | Our lab | 88 |

*This library was generated in-house, including 88 selected small molecules related to pluripotency, reprogramming or epigenetic modification

TABLE 1D

Small-molecule compounds tested in reprogramming

| Full Name | Abbreviation | Concentration (μM) | Source | Molecular Weight | Structure |
|---|---|---|---|---|---|
| Valproic acid sodium salt | VPA, V | 500 | Sigma, cat. no. P4543 | 166.19 | 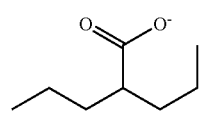 |

TABLE 1D-continued

Small-molecule compounds tested in reprogramming

| Full Name | Abbreviation | Concentration (μM) | Source | Molecular Weight | Structure |
|---|---|---|---|---|---|
| CHIR99021 | CHIR, C | 10-20 * | Synthesized by WUXIAPPTEC | 465.34 | 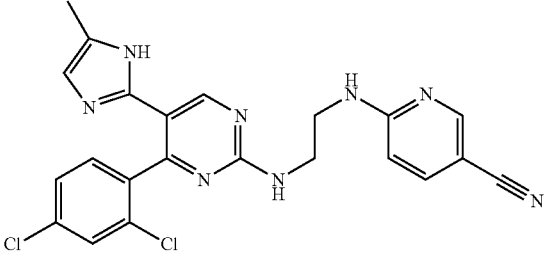 [SMILES: Cc1cnc(-c2cnc(NCCNc3ccc(C#N)cn3)nc2-c2ccc(Cl)cc2Cl)[nH]1] |
| 616452 | 6 | 5-10 | Synthesized by WUXIAPPTEC | 400.34 | 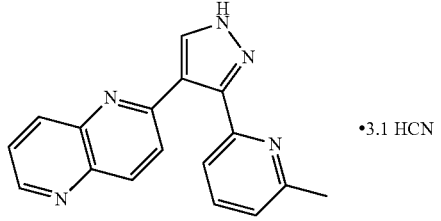 [SMILES: Cc1cccc(-c2n[nH]cc2-c2ccc3ncccc3n2)n1] |
| Tranylcypromine | Tranyl, T | 5-10 | Enzo, cat. no. BML-E1217-0005 | 182.23 | 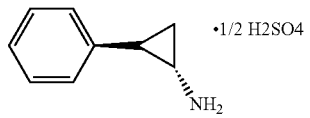 |
| Forskolin | FSK, F | 10-50 ** | Enzo, cat. no. BML-CN100-0100 | 410.50 | 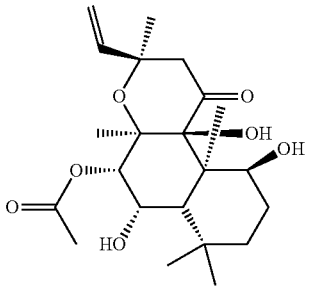 |
| 3-deazaneplanocin A | DZNep, Z | 0.05-0.1 | Synthesized by WUXIAPPTEC | 262.26 | 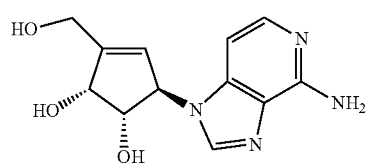 [SMILES: Nc1nccc2c1ncn2[C@@H]1C=C(CO)[C@@H](O)[C@H]1O] |
| 2-Methyl-5-hydroxytryptamine hydrocholoride | 2-Me-5HT, M | 5 | Synthesized by WUXIAPPTEC | 233.99 | 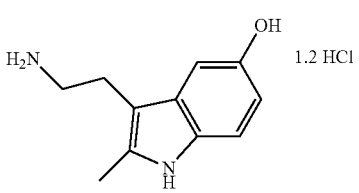 |

TABLE 1D-continued

Small-molecule compounds tested in reprogramming

| Full Name | Abbreviation | Concentration (μM) | Source | Molecular Weight | Structure |
|---|---|---|---|---|---|
| D4476 | D | 5 | Synthesized by WUXIAPPTEC | 398.41 | 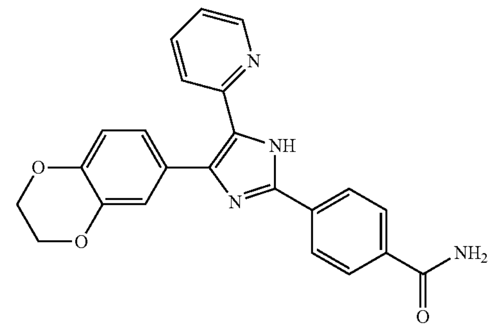 [SMILES: NC(=O)c1ccc(-c2nc(-c3ccc4c(c3)OCCO4)c(-c3ccccn3)[nH]2)cc1] |
| PD0325901 | | 1 | Synthesized by WUXIAPPTEC | 482.00 | 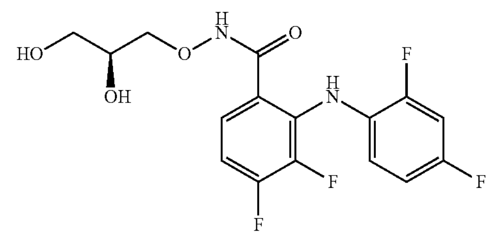 [SMILES: O=C(NOC[C@@H](O)CO)c1ccc(F)c(F)c1Nc1ccc(F)cc1F] |
| Adenosine periodate oxidized | Adox | 10 | Santa Cruz, cat. no. nc-214510 | 265.23 | 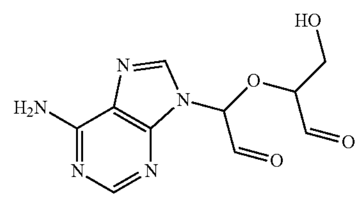 [SMILES: Nc1ncnc2c1ncn2C(C=O)OC(C=O)CO] |
| IBMX | | 50 | Tacris, cat. no. 2845 | 222.24 | 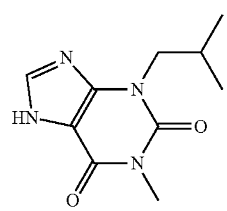 [SMILES: CC(C)Cn1c(=O)n(C)c(=O)c2[nH]cnc21] |
| Dibutyryl cAMP | DBcAMP | 50 | Santa Cruz, cat. no. nc-201567 | 491.37 | 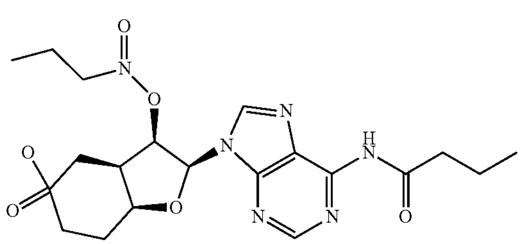 |
| 2',5'-Dideoxyadenosine | 2'5'ddAdo | 5-20 | Santa Cruz, cat. no. nc-201562 | 235.20 | 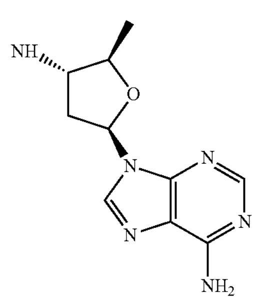 [SMILES: C[C@H]1O[C@@H](n2cnc3c(N)ncnc32)C[C@@H]1N] |

TABLE 1D-continued
Small-molecule compounds tested in reprogramming
| Full Name | Abbreviation | Concentration (μM) | Source | Molecular Weight | Structure |
|---|---|---|---|---|---|
| Prostaglandin E2 | PGE2, P | 5 | Caymen, cat. no. 14010 | 352.46 | 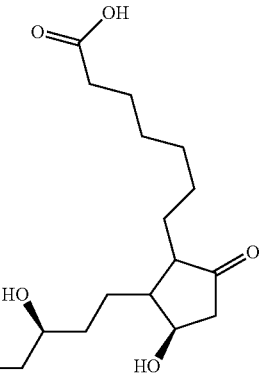 |
| Rolipram | | 10 | Tacris, cat. no. 0905 | 275.35 | 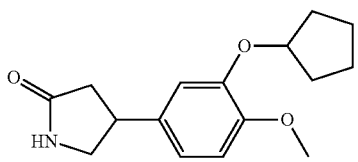 [SMILES: COc1ccc(C2CNC(=O)C2)cc1OC1CCCC1] |
| Sodiumbutyane | NaB, B | 20 | Sigma, cat. no. B5887 | 110.09 | 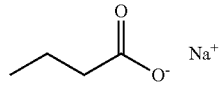 |
| SKT1720 | S | 1 | Selleck, cat. no. S1129 | 506.02 | 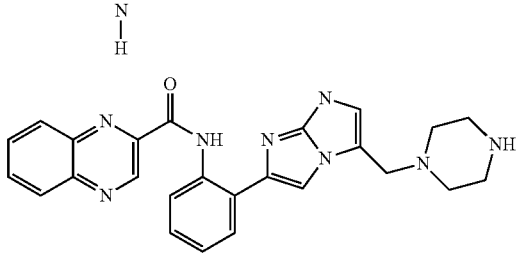 |
| UNC0638 | UNC, U | 0.5 | Tacris, cat. no. 4343 | 509.73 | 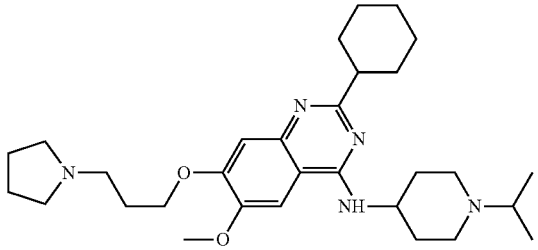 [SMILES: COc1cc2c(NC3CCN(C(C)C)CC3)nc(C3CCCCC3)nc2cc1OCCCN1CCCC1] |
| Ionomycin | | 4 | Calbiochem cat. no. 403952 | 747.06 | 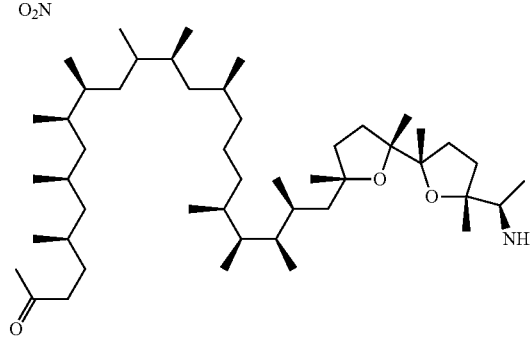 [SMILES: "O2N" ; CC(=O)CC[C@@H](C)C[C@@H](C)C[C@@H](C)[C@@H](C)CC(C)[C@@H](C)C[C@@H](C)CCC[C@H](C)[C@H](C)[C@H](C)[C@@H](C)C[C@]1(C)CC[C@](C)([C@]2(C)CC[C@](C)([C@@H](C)N)O2)O1] |

TABLE 1D-continued
Small-molecule compounds tested in reprogramming
| Full Name | Abbreviation | Concentration (μM) | Source | Molecular Weight | Structure |
|---|---|---|---|---|---|
| BIX-01294 | | 1 | Stengent, cat. no. 04-0002 | 490.64 | 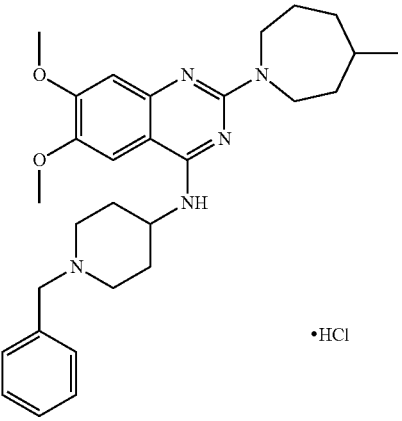 [SMILES: COc1cc2nc(N3CCCC(C)CC3)nc(NC3CCN(Cc4ccccc4)CC3)c2cc1OC ; Cl] |
| (−)Neplanocin A | Nep A | 1 | Cayman, cat. no. 10584 | 263.25 | 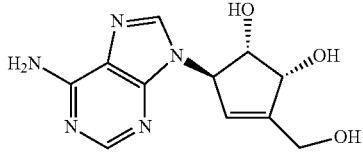 [SMILES: Nc1ncnc2c1ncn2[C@@H]1C=C(CO)[C@@H](O)[C@H]1O] |
| 3-Deamadenoxine | DZA | 10 | Cayman, cat. no. 9000785 | 266.25 | 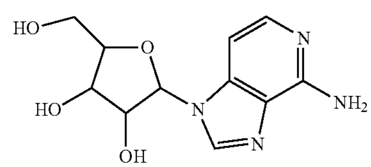 [SMILES: Nc1nccc2c1ncn2C1OC(CO)C(O)C1O] |
| Budesonide | Bude | 5 | Tacris, cat. no. 2671 | 430.53 | 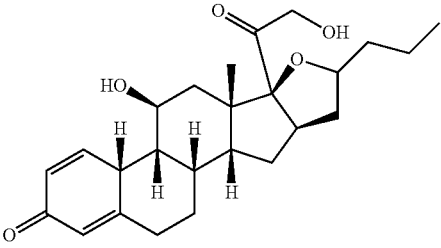 |
| RG108 | R | 20-40 | Tacris, cat. no. 3295 | 334.33 | 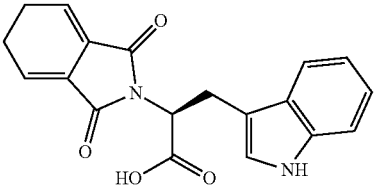 |
| 5-Azacytidine | 5-aza-C | 5 | Tacris, cat. no. 3842 | 244.20 | 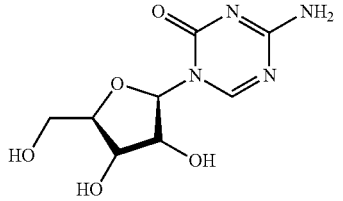 |

TABLE 1D-continued
Small-molecule compounds tested in reprogramming
| Full Name | Abbreviation | Concentration (μM) | Source | Molecular Weight | Structure |
| --- | --- | --- | --- | --- | --- |
| Adenine | | 2 | Calboichem, cat. no. 1152 | 135.13 | 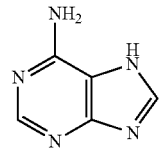 |
| Adenorine | | 2 | Calboichem, cat. no. 1160CBC | 267.24 | 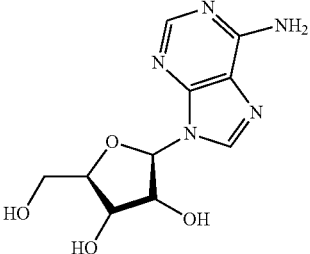 |
| SF1670 | | 1 | Callagen Technology, cat. No. C7316-2s | 307.34 | 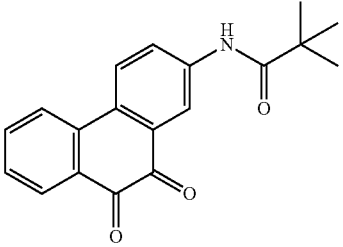 [SMILES: CC(C)(C)C(=O)Nc1ccc2c(c1)C(=O)C(=O)c1ccccc1-2] |
| DY131 | | 5 | Tacris, cat. no. 2266 | 311.38 | 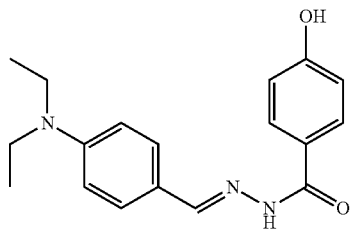 [SMILES: CCN(CC)c1ccc(/C=N/NC(=O)c2ccc(O)cc2)cc1] |
| Nimesulide | | 2 | Tacris, cat. no. 2470 | 308.31 | 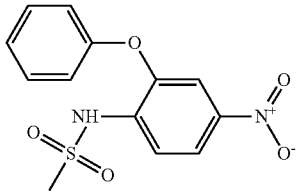 [SMILES: CS(=O)(=O)Nc1ccc([N+](=O)[O-])cc1Oc1ccccc1] |
| Resveratrol | | 3 | Tacris, cat. no. 1418 | 228.25 | 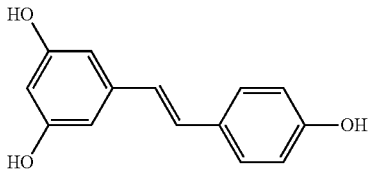 [SMILES: Oc1ccc(/C=C/c2cc(O)cc(O)c2)cc1] |

TABLE 1D-continued

Small-molecule compounds tested in reprogramming

| Full Name | Abbreviation | Concentration (μM) | Source | Molecular Weight | Structure |
|---|---|---|---|---|---|
| TTNP B | N | 1 | Tacris, cat. no. 0761 | 348.48 | 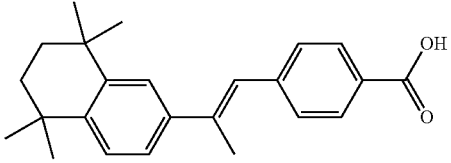 [SMILES: C/C(=C\c1ccc(C(=O)O)cc1)c1ccc2c(c1)C(C)(C)CCC2(C)C] |

Note:
* For CiPSCs induction from MEFs, the concentration of CHIR99021 was 10 μM. For CiPSCs indication from MNFs, MAFs or ADSCs, and CiPSCs indication without replacing, the concentration of CHIR99021 was elevated to 20 μM during day 0-12.
** For CiPSCs induction from MEFs, the concentration of Forskolin was 10 μM. For CiPSCs induction from MNFs, MAFs or ADSCs, the concentration of Forskolin was elevated to 50 uM during day 0-12.

Plasmid Construction and Lentivirus Production

The pLL3.7-ΔU6 vector was described by (McQualter, et al., *Stem Cells*, 27:623-633 (2009). Mouse Sall4 was amplified from ESCs (TT2) by RT-PCR, cloned into the pEASY-Blunt vector (TransGen Biotech), confirmed by sequencing and then introduced into the XhoI/EcoRT sites of pLL3.7-ΔU6. The primers are listed in Table 2.

TABLE 2

Primer sets for PCR reactions

| Genes | Forward (5' to 3') | Reverse (5' to 3') |
|---|---|---|
| For plasmid construction | | |
| Sall4 | ACTCGAGCCACCATGTCGAGGCGCAAGC AGGCGAA (SEQ ID NO: 1) | GCAATTGTTAGCTGACAGCAATCTTATT CTTCTCC (SEQ ID NO: 2) |
| For qRT-PCR | | |
| Sox2 | CGGGAAGCGTGTACTTATCCTT (SEQ ID NO: 3) | GCGGAGTGGAAACTTTTGTCC (SEQ ID NO: 4) |
| Klf4 | TTGCGGTAGTGCCTGGTCAGTT (SEQ ID NO: 5) | CTATGCAGGCTGTGGCAAAACC (SEQ ID NO: 6) |
| Oct4 | CAGGGCTTTCATGTCCTGG (SEQ ID NO: 7) | AGTTGGCGTGGAGACTTTGC (SEQ ID NO: 8) |
| Gata4 | GAGCTGGCCTGCGATGTCTGAGTG (SEQ ID NO: 9) | AAACGGAGCCCAAGAACCTGAAT (SEQ ID NO: 10) |
| Gata6 | TGAGGTGGTCGCTTGTGTAG (SEQ ID NO: 11) | ATGGCGTAGAAATGCTGAGG (SEQ ID NO: 12) |
| Sox17 | GTCAACGCCTTCCAAGACTTG (SEQ ID NO: 13) | GTAAAGGTGAAAGGCGAGGTG (SEQ ID NO: 14) |
| Esrrb | CTGGCTGAGGGCATCAATG (SEQ ID NO: 15) | AACCGAATGTCGTCCGAAGAC (SEQ ID NO: 16) |
| Sall4 | TGGCAGACGAGAAGTTCTTTC (SEQ ID NO: 17) | TCCAACATTTATCCGAGCACAG (SEQ ID NO: 18) |
| Lin28a | CCGCAGTTGTAGCACCTGTCT (SEQ ID NO: 19) | GAAGAACATGCAGAAGCGAAGA (SEQ ID NO: 20) |
| Dppa2 | GCGTAGCGTAGTCTGTGTTTG (SEQ ID NO: 21) | TCAACGAGAACCAATCTGAGGA (SEQ ID NO: 22) |
| Nanog | AGTTATGGAGCGGAGCAGCAT (SEQ ID NO: 23) | AGGCCTGGACCGCTCAGT (SEQ ID NO: 24) |
| For genomic PCR | | |
| pLL-Oct4 | GAAGGATGTGGTCCGAGT (SEQ ID NO: 25) | GCAGCGTATCCACATAGCGT (SEQ ID NO: 26) |

TABLE 2-continued

Primer sets for PCR reactions

| Genes | Forward (5' to 3') | Reverse (5' to 3') |
|---|---|---|
| pLL-Sox2 | CATGGGTTCGGTGGTCAA (SEQ ID NO: 27) | GCAGCGTATCCACATAGCGT (SEQ ID NO: 28) |
| pLL-Klf4 | ACCACTGTGACTGGGACG (SEQ ID NO: 29) | GCAGCGTATCCACATAGCGT (SEQ ID NO: 30) |
| pLL-cMyc | TACATCCTGTCCGTCCAAGC (SEQ ID NO: 31) | GCAGCGTATCCACATAGCGT (SEQ ID NO: 32) |
| fu-tet-hOct4 | ACCTCCATAGAAGACACCG (SEQ ID NO: 33) | TAGCCCCACTCCAACCTG (SEQ ID NO: 34) |
| fu-tet-hSox2 | ACCTCCATAGAAGACACCG (SEQ ID NO: 35) | CTCCGACAAAAGTTTCCACTCG (SEQ ID NO: 36) |
| fu-tet-hKlf4 | ACCTCCATAGAAGACACCG (SEQ ID NO: 37) | GAAGAGGAGGCTGACGCT (SEQ ID NO: 38) |
| fu-tet-hcMyc | ACCTCCATAGAAGACACCG (SEQ ID NO: 39) | GGGTCGCAGATGAAACTC (SEQ ID NO: 40) |
| For bisulfite genomic sequencing | | |
| Oct4 | GGAGTGGTTTTAGAAATAATTG (SEQ ID NO: 41) | TCCAACCCTACTAACCCATCACC (SEQ ID NO: 42) |
| Nanog | GATTTTGTAGGTGGGATTAATTGTGAA TTT (SEQ ID NO: 43) | ACCAAAAAAACCCACACTCATATCAAT ATA (SEQ ID NO: 44) |
| For chromatin immunoprecipitation | | |
| Oct4 | CTGTAAGAACAGGCCGAGAG (SEQ ID NO: 45) | CAGGAGGCCTTCATTTTCAA (SEQ ID NO: 46) |
| Nanog | CTATCGCCTTGAGCCGTTG (SEQ ID NO: 47) | AACTCAGTGTCTAGAAGGAAAGATCA (SEQ ID NO: 48) |
| Sox2 | TTTATTCAGTTCCCAGTCCAA (SEQ ID NO: 49) | TTATTCCTATGTGTGAGCAAGA (SEQ ID NO: 50) |
| For OG (Oct4 promoter-driven GFP) cassette | | |
| OG | AACCACTACCTGAGCACCC (SEQ ID NO: 51) | ACCTCTACAAATGGTATG (SEQ ID NO: 52) |

The lentiviral vectors containing the other individual reprogramming factors (Oct4, Sox2, Klf4 or c-Myc) were described by Zhao, et al., *Cell Stem Cell*, 3:475-479 (2008). For tet-on Oct4 systems, Fu-tet-hOct4 and FUdeltaGW-rtTA were the same as described by Li, et al., *Cell Res.*, 21:196-204 (2011); Maherali, et al., *Cell Stem Cell*, 3:340-345 (2008). Genetic knockdown was carried out using shRNAs (SIGMA MissionR shRNA) according to the manufacturer's protocol. The shRNA sequences are listed in Table 3. Lentivirus production, collection and infection were as described by Zhao, et al., *Cell Stem Cell*, 3:475-479 (2008).

TABLE 3

Sequences of shRNAs

| shRNA | | Sequences (5'-3') |
|---|---|---|
| Sall4 | shRNA 1 | CCGGCAGCCCACCTTTGTCAAAGTTCTCGAG AACTTTGACAAAGGTGGGCTGTTTTTG (SEQ ID NO: 53) |
| | shRNA 2 | CCGGGCCCACCTTTGTCAAAGTTGACTCGAG TCAACTTTGACAAAGGTGGGCTTTTTG (SEQ ID NO: 54) |
| Gata4 | shRNA 1 | CCGGAGCCCAAGAACCTGAATAAATCTCGAG ATTTATTCAGGTTCTTGGGCTTTTTG (SEQ ID NO: 55) |
| | shRNA 2 | CCGGCATCTCCTGTCACTCAGACATCTCGAG ATGTCTGAGTGACAGGAGATGTTTTG (SEQ ID NO: 56) |
| Gata6 | shRNA 1 | CCGGCCACTACCTTATGGCGTAGAACTCGAG TTCTACGCCATAAGGTAGTGGTTTTTG (SEQ ID NO: 57) |
| | shRNA 2 | CCGGCCTCGACCACTTGCTATGAAACTCGAG TTTCATAGCAAGTGGTCGAGGTTTTTG (SEQ ID NO: 58) |
| Sox17 | shRNA 1 | CCGGCCCACAATCACTGTCCAGTTTCTCGAG AAACTGGACAGTGATTGTGGGTTTTTG (SEQ ID NO: 59) |
| | shRNA 2 | CCGGCGCACGGAATTCGAACAGTATCTCGAG ATACTGTTCGAATTCCGTGCGTTTTTG (SEQ ID NO: 60) |

TABLE 3-continued

Sequences of shRNAs

| shRNA | | Sequences (5'-3') |
|---|---|---|
| Ezh2 | shRNA 1 | CCGGGCTAGGCTAATTGGGACCAAAGCTGAG TTTGGTCCCAATTAGCCTAGCTTTTTG (SEQ ID NO: 61) |
| | shRNA 2 | CCGGCGGCTCCTCTAACCATGTTTACTCGAG TAAACATGGTTAGAGGAGCCGTTTTG (SEQ ID NO: 62) |
| Control | shRNA control | CCGGCAACAAGATGAAGAGCACCAACTCGAG TTGGTGCTCTTCATCTTGTTGTTTTG (SEQ ID NO: 63) |

CiPSC Induction

The initial cells (MEFs, MNFs, MAFs or ADSCs) were seeded at a density of 50,000 cells per well of a 6-well plate or 300,000 cells per 100 mm dish. On the next day (day 0), the original medium was replaced with chemical reprogramming medium containing the small-molecule combinations. The small-molecule combinations-containing medium was changed every 4 days. On day 12, these cells were washed in PBS and digested with 0.25% Trypsin-EDTA (Invitrogen) at 37° C. for 3-5 min. After neutralization, the cell clumps were dissociated into single cells by thorough pipetting. The cells were harvested (300,000-1,000,000 cells per well of a 6-well plate) and replated at a density of 300,000-500,000 cells per well of a 6-well plate in the chemical reprogramming medium containing the small-molecule combinations. DZNep was added to the cell cultures on day 16 or day 20. On day 28-36, the small-molecule combinations including DZNep were removed. Meanwhile, the chemical reprogramming medium was replaced with 2i-medium. After another 8-12 days, 2i-competent, ESC-like and GFP-positive colonies were counted as primary CiPSC colonies. For CiPSC induction from wild-type cells without OG reporter, 2i-competent and ESC-like colonies were counted as primary CiPSC colonies. These CiPSC colonies were picked up for expansion and characterization. Alternatively, CiPSCs could be induced without replating on day 12.

Immunofluorescence, RT-PCR, Genomic PCR, Teratoma Formation and Karyotype Analysis Immunofluorescence, RT-PCR, genomic PCR and teratoma formation were all carried out as previously described. For immunofluorescence, the primary antibodies included SSEA-1 (Millipore, MAB4301), OCT4 (Abcam, ab18976), SOX2 (Santa Cruz, sc-17320), KLF4 (Santa Cruz, sc-20691), REX1 (Santa Cruz, sc-99000), NANOG (R&D, AF2729), UTF1 (Abcam, ab24273), SALL4 (Santa Cruz, sc-166033). Secondary antibodies were Rhodamine-conjugated, including Donkey Anti Mouse IgG (H+L)(Jackson ImmunoResearch, 715-025-150), Donkey Anti Goat IgG (H+L) (Jackson ImmunoResearch, 705-025-147), and Donkey Anti Rabbit IgG (H+L) (Jackson ImmunoResearch, 711-025-152). Primers for RT-PCR were the same as described previously (Li, et al., Cell Res., 21:196-204 (2011)). Primers for genomic PCR are shown in Table 2. Karyotype analyses were performed as reported (Longo, et al., Transgenic Res. 6:321-328 (1997)).

Real-time PCR

Total RNA from an entire well of cultured cells was isolated using the RNeasy Plus MiniKit (QIAGEN). For a single colony, RNA was isolated using the RNeasy Micro Kit (QIAGEN). RNA was converted to cDNA using TransScript First-Strand cDNA Synthesis SuperMix (TransGen Biotech). PCR was carried out using Power SYBRR Green PCR Master Mix (Applied Biosystems) and performed on an ABI Prism 7300 Sequence Detection System. The data were analyzed using the delta-delta Ct method. The primers used for real-time PCR are listed in Table 2.

Chimera Construction

Chimeric mice were obtained by the injection of CiPS cells into blastocysts using a sharp injection needle or into eight-cell embryos using a XY Clone laser system (Hamilton ThorneBioscience). For blastocyst injection, 10-15 CiPS cells were injected into the recipient embryo cavity of F2 (intercross of B6D2F1) or CD-1 (albino) female mice at 3.5 d (days postcoitum). Host eight-cell embryos were collected from female mice at 2.5 d, and 7-10 CiPS cells were injected into each embryo. After injection, blastocysts and eight-cell embryos (6-8 embryos in each oviduct or horn of the uterus) were transferred into 2.5 d or 0.5 d pseudopregnant CD-1 females, respectively. Chimeric mice were identified by coat color and then assessed for germline transmission by mating with ICR mice.

DNA Microarray and RNA-seq

Total mRNA was isolated from mouse fibroblasts, CiPSCs and ESCs. Microarrays were performed as reported by Li, et al., Cell Res., 21:196-204 (2011). RNA sequencing libraries were constructed using the Illumina mRNA-seq Prep Kit (Illumina). Fragmented and randomly primed 200 bp paired-end libraries were sequenced using Illumina HiSeq 2000. Hierarchical clustering of the microarray data was performed as reported by Li, et al., Cell Res., 21:196-204 (2011). Heatmaps were generated using R (Bioconductor).

Bisulfite Genomic Sequencing

Genomic DNA was modified by bisulfite treatment and purified using the MethylCode™ Bisulfite Conversion Kit (Invitrogen) according to the manufacturer's protocol. The primers are listed in Table 2. The amplified fragments were cloned into the pEASY-blunt Vector (Transgene). Ten randomly picked clones from each sample were sequenced.

cAMP, S-adenosylmethionine (SAM) and S-adenosylhomocysteine (SAH) Quantification cAMP was quantified using the Direct cAMP ELISA Kit (Enzo) according to the manufacturer's protocol. For SAM and SAH quantification, cultured cells (1,000,000 cells) were trypsinized and homogenized by ultrasonication in 200 µl PBS. Then 40 µl of 400 mg/ml TCA was added. Cell extracts were incubated on ice for 30 min. After centrifugation at 4° C. (13,000 rpm, 15 min), the supernatants were filtered through a 0.22 µm filter and analyzed by high-performance liquid chromatography (HPLC, Shimadzu) with HILIC columns (Waters).

Comparative Genomic Hybridization (CGH) Analysis.

For CGH experiments, genomic DNA was extracted and hybridized to NimbleGen 3×720K mouse whole-genome tiling arrays by Imagenes using C57BL/6 MEF DNA as a reference (Gene BioDesign).

Flow Cytometry Analysis

Cultured cells were trypsinized into single cells and then resuspended in PBS containing 3% fetal bovine serum. Using endogenous Oct4-GFP, FACS analyses were performed with a FACSCalibur instrument (BD Biosciences). The data were analyzed with FCS Express 4 (De Novo).

Chromatin Immunoprecipitation (ChIP)

ChIP was performed using the EZ-Magna ChIP A/G Kit (Millipore) according to the manufacturer's protocol. Anti-H3K27me3 (Abcam, ab6002), anti-H3K9me2 (Millipore, 07-441), anti-H3K4me3 (Abcam, ab8580) and anti-H3K9ac (Abcam, ab4441) antibodies were used. Following immunoprecipitation, DNA was analyzed by real-time PCR. The primers used are listed in Table 2.

Southern Blot

Southern blot was performed with the DIG High Prime DNA Labeling and Detection Starter Kit II (Roche, 11 585 614 910), with reference to "Roche Techniques for Hybridization of DIG-labeled Probes to a Blot". 20 µg genomic DNA isolated from iPS cells or MEFs was digested with EcoRI and XbaI. The DNA probe was designed based on psi sequence, which is present in the pLL3.7-_U6 vector and Fu-tet vectors and could thus be integrated into the genome along with exogenous transgenes after virus infection.

Luciferase Activity Assays

MEFs were plated at a density of 40,000 cells per well of a 24-well plate and transiently transfected with Oct4 promoter reporters using Lipofectamine LTX & Plus Reagent (Invitrogen) according to the manufacturer's instructions. pRL-TK plasmids (Promega) were cotransfected in each well as internal references, and the total DNA concentrations for all transfections were equalized by adding empty pLL3.7-_U6 vector. At 48 hours after transfection, cells were washed in PBS and lysed in passive lysis buffer (Promega). Luciferase activity was measured with the Dual-luciferase Reporter Assay System (Promega) using a Centro LB960 96-well luminometer (Berthold Technologies) and normalized to Renilla luciferase activity. Empty expression vector plasmids were used as negative control. The fold activation describes the ratio of firefly to Renilla luciferase activity for each condition compared with that of the empty vector control.

Western Blot Analysis

Cells were cultured in 100 mm dishes, washed in PBS and scraped in lysis buffer. Aliquots were loaded onto an 8-10% SDS-polyacrylamide gel and blotted onto a nitrocellulose membrane. Membranes were incubated overnight at 4° C. with rabbit anti-EZH2 (Abcam, ab3748) at a dilution of 1:1000. Goat anti Rabbit IgG(H+L)/HRP (ZSBIO, ZB-2301) was used as the secondary antibody. Detection was performed using SuperSignal West Pico solutions (Pierce).

Example 1

Chemical Substitutes for Oct 4

To identify chemical substitutes of Oct4, MEFs from OG mice were plated at a density of 20,000 cells per well of a 12-well plate and infected with lentiviruses encoding Sox2, Klf4 and c-Myc. After infection, the medium was replaced with LIF-free ESC culture medium. Individual chemicals from small-molecule libraries were added to each well. The medium and chemicals were changed every 4 days. Chemical treatments were continued for 14-20 days or until GFP-positive colonies appeared. Primary hits were selected for further confirmation and optimization.

Small molecules that enable reprogramming in the absence of Oct4 were searched using Oct4 promoter-driven green fluorescent protein (GFP) expression (OG) mouse embryonic fibroblasts (MEFs), with viral expression of Sox2, Klf4, and c-Myc. After screening up to 10,000 small molecules (Table 1C), Forskolin (FSK), 2-methyl-5-hydroxytryptamine (2-Me-5HT), and D4476 (Table 1D) were identified as chemical "substitutes" for Oct4 (FIG. 1A to 1F).

Figure 1B:
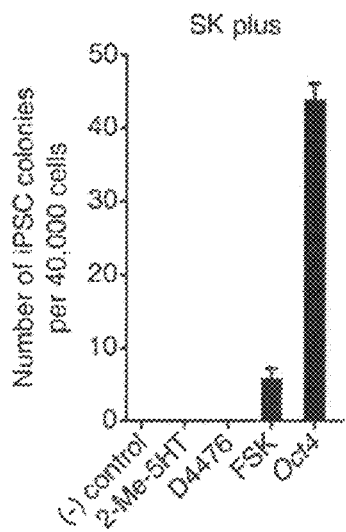
Figure 1D:
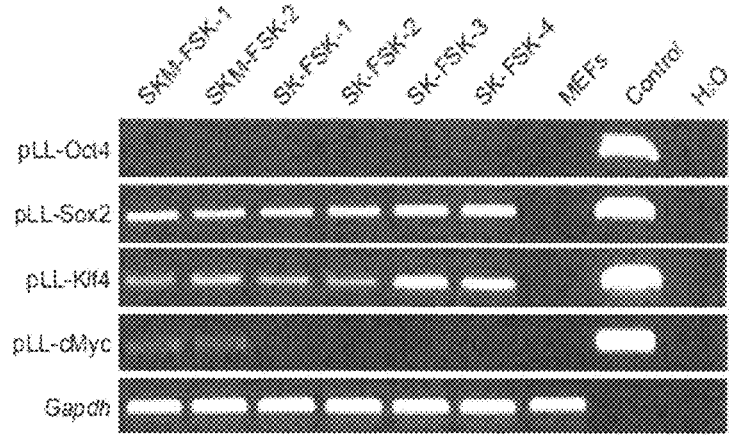
FIG. 1D shows genomic PCR analysis of SKM-FSK-iPSCs and SK-FSK-iPSCs.
Figure 1E:
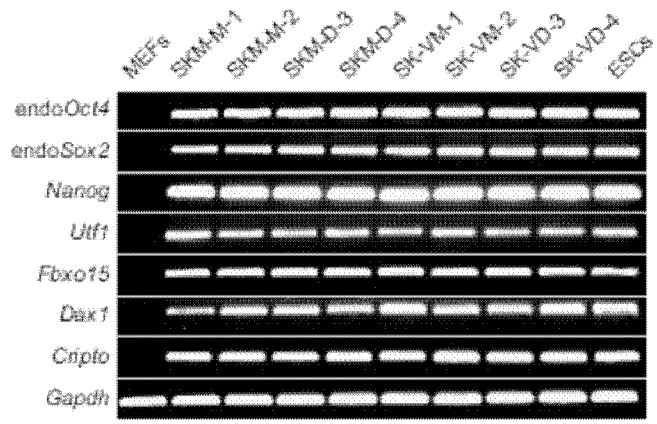
FIGS. 1E and 1F show JRT-PCR (FIG. 1E and genomic PCR (FIG. 1F) analysis of iPSC colonies induced by SKM or SK with chemicals treatment. Abbreviations: M (2-Me-5HT); D (D4476); V (VPA). Tg indicates exogenously introduced genes. Scale bars, 100 μM.
Figure 1F:
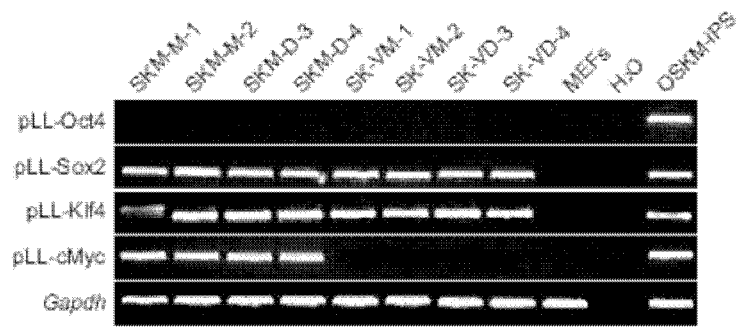

Passaged SKM-FSK-iPSCs exhibit typical ESC morphology and homogeneously express GFP (FIG. 1B). The SKM-FSK-iPSCs can contribute to chimeric mice, including gonadal tissues. Similarly, iPSCs induced by SKM with 2-Me-5HT treatment can contribute to chimeric mice.

Figure 2:
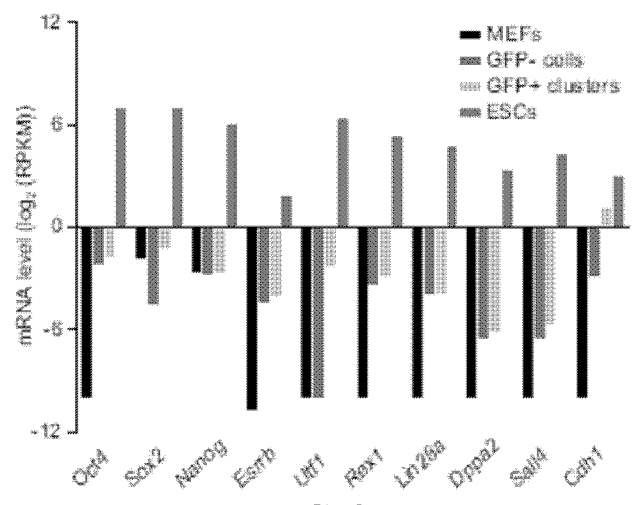
FIG. 2 shows mRNA levels of pluripotency-related genes detected by RNA-seq analysis in MEFs, GFP-negative cells, GFP-positive clusters and ESCs (R1). GFP-negative cells and GFP-positive clusters were collected on day 24. Cdh1=E-cadherin.

A small molecule combination "VC6T" [VPA, CHIR99021 (CHIR), 616452, tranylcypromine], that enables reprogramming with a single gene, Oct4 (Li, et al., Cell Res., 21:196-204 (2011)), was used next to treat OG-MEFs plus the chemical substitutes of Oct4 in the absence of transgenes. The data shows that VC6T plus FSK (VC6TF) induced some GFP-positive clusters expressing E-cadherin, a mesenchyme-to-epithelium transition marker, reminiscent of early reprogramming by transcription factors (Li, et al., Cell Stem Cell, 7:51-63 (2010); Samavarchi-Tehrani, et al., Cell Stem Cell, 7:64-77 (2010)) (FIG. 2). However, the expression of Oct4 and Nanog was not detectable, and their promoters remained hypermethylated, suggesting a repressed epigenetic state (FIGS. 2A and 2B).

Example 2

Small Molecules that Facilitate Late Reprogramming

To identify small molecules that facilitate late reprogramming, a doxycycline (DOX)-inducible Oct4 expression screening system was used (Li, et al., Cell Res. 21:196-204 (2011)).

MEFs from OG mice were plated as described above and infected with Fu-tet-hOct4 and FUdeltaGW-rtTA lentiviruses. The induction protocol was carried out as described above.

After infection, the culture medium was replaced with LIF-free ESC culture medium containing VC6T (VPA, CHIR99021, 616452, Tranylcypromine) plus DOX (1 µg/ml). Alternatively, MEFs harboring DOX-inducible Oct4 from Tet-On POU5F1 mouse strain B6; 129-Gt(ROSA) 26Sor$^{tm1(rTA*M2)Jae}$ COl1a1$^{tm2(tetO-Pou5f1)Jae}$/J were used in this screen (Li, et al., Cell Res., 21:196-204 (2011)). These two DOX-inducible systems were only used in this screen, but not in complete chemical reprogramming. Individual chemicals from small-molecule libraries were added to each well. The concentrations of small molecules are listed in Table 1D. Small molecules were added at different culture time points. 5-aza-C (5-Azacytidine) and DZNep were added from day 8. The medium and chemicals were changed every 4 days; DOX was added only for the first 4-8 days. Chemical treatments were continued for 16-24 days or until GFP-positive colonies appeared. Primary hits were selected for further confirmation and optimization. CiPSC colonies were counted on day 44. Primary hits were selected for further confirmation and optimization.

Figure 3:
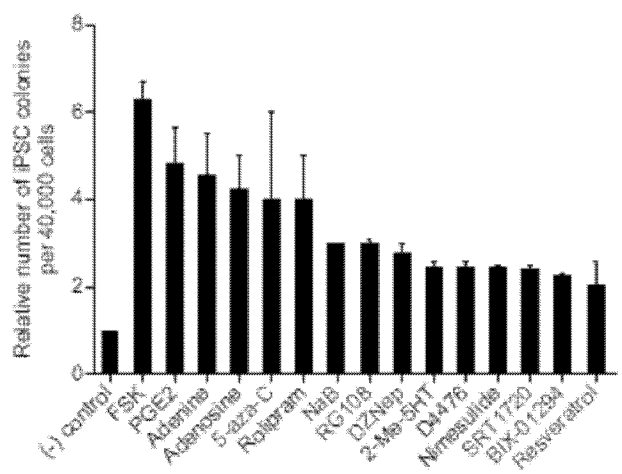
FIG. 3 is a bar graph showing relative number of iPSC colonies following treatment with indicated small molecules. (−) control, DMSO. Error bars indicate s.d (n≥2). Abbreviations: PEG2 (Prostaglandin E12); 5-aza-C (5-Azacytidine; NaB (Sodium Butyrate).

Small molecule hits, including several cAMP agonists (FSK, Prostaglandin E2, and Rolipram) and epigenetic modulators [3-deazaneplanocin A (DZNep), 5-Azacytidine, sodium butyrate, and RG108], were identified in this screen (FIG. 3 and Table 1D).

Example 3

Complete Chemical Reprogramming without the Oct-4 Inducible System

Figures 4A, 4B:
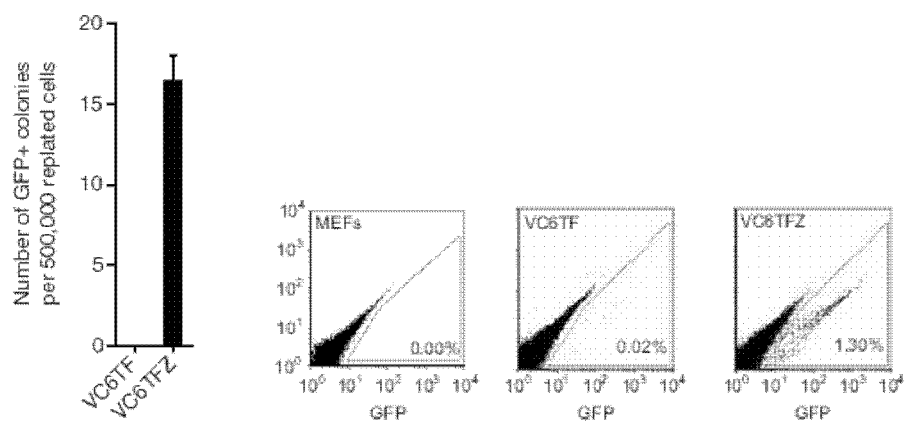
FIG. 4A shows numbers of GFP-positive colonies induced after DZNep treatment on day 36. Error bars, mean± SD (n=2 biological repeat wells).
FIG. 4B is a FACS analysis of GFP-positive cells induced from OG-MEFs. Left, the absence of GFP-positive cells in initial MEFs; middle and right, proportion of GFP-positive cells induced by VC6TF (middle) and VC6TFZ (right) on day 44.
Figure 4C:
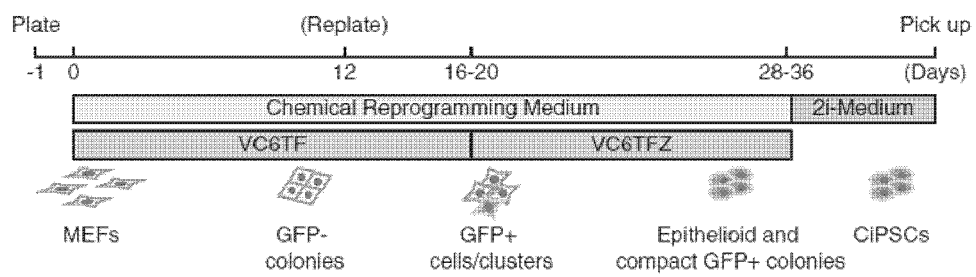
FIG. 4C is a Schematic diagram illustrating the process of CiPSC generation. Scale bars, 100 mm. For (FIG. 4A), cells for reprogramming were replated on day 12.
Figure 4D:
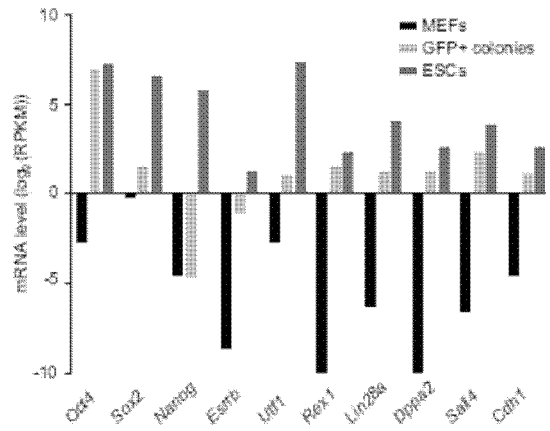
FIG. 4D shows mRNA levels of pluripotency-related genes detected by RNA-seq analysis in MEFs, GFP-positive colonies and ESCs (R1). Unlike mouse ESC colonies, these GFP-positive colonies, which were epithelioid and compact, could not maintain in ESC culture condition and were collected on day 36.
Figure 4E:
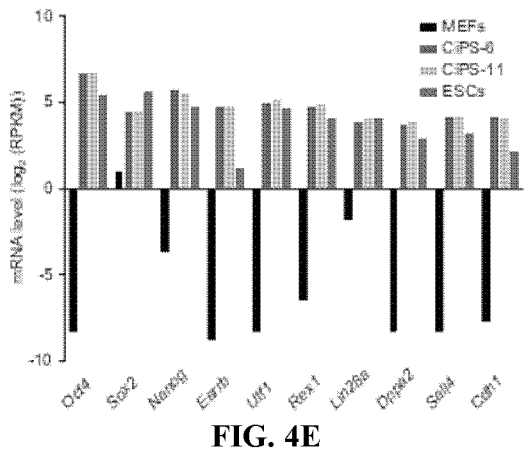
FIG. 4E shows mRNA levels of pluripotency-related genes detected by RNA-seq analysis in MEFs, CiPSCs and ESCs (R1).

To achieve complete chemical reprogramming without the Oct4-inducible system, small molecules were further tested in the chemical reprogramming of OG-MEFs without transgenes. When DZNep was added 16 days after treatment with VC6TF (VC6TFZ), GFP-positive cells were obtained more frequently by a factor of up to 65 than those treated with VC6TF, forming compact, epithelioid, GFP-positive colonies without clearcut edges (FIGS. 4A-B and 4E). In these cells, the expression levels of most pluripotency marker genes were elevated but were still lower than in ESCs, suggesting an incomplete reprogramming state (FIGS. 4G and H). After switching to 2i medium with dual inhibition (2i) of glycogen synthase kinase-3 and mitogen-activated protein kinase signaling after day 28 post treatment, certain GFP-positive colonies developed an ESC-like morphology (domed, phase-bright, homogeneous with clear-cut edges) (FIG. 4C) (Silva, et al., *PLoS Biol.*, 6:e253 (2008); Theunissen, et al., *Curr. Biol.*, 21:65-71 (2011)). These colonies could be further cultured for more than 30 passages, maintaining an ESC-like morphology (FIGS. 4A, 4D and 4G). These are referred to as 2i-competent, ESC-like, and GFP-positive cells as chemically induced pluripotent stem cells (CiPSCs). A schematic diagram for the formation of CiPSCs as described above is shown in FIG. 4F.

Figure 5A:
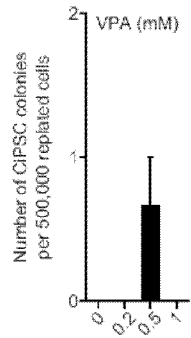
FIGS. 5A-K show optimization of the concentrations and treatment durations for individual chemicals in the VC6TFZ condition.
Figure 5B:
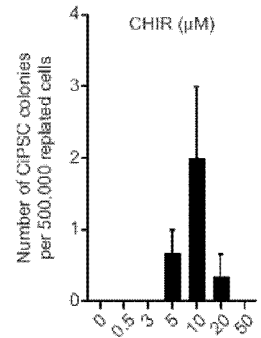
Figure 5C:
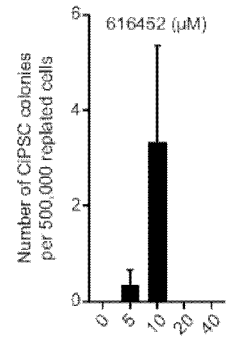
Figure 5D:
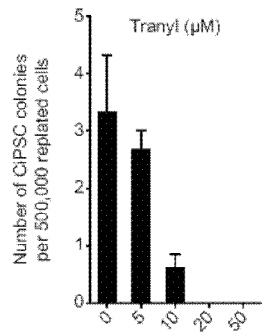
Figure 5E:
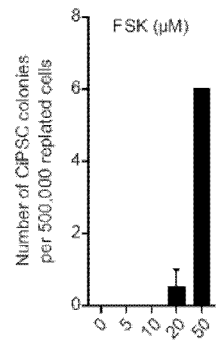
Figure 5F:
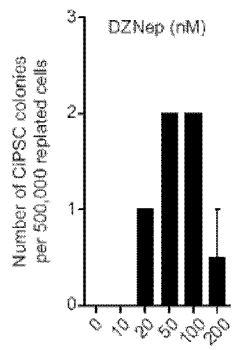
Figure 5G:
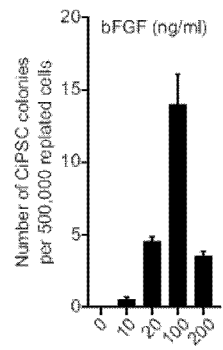
Figure 5H:
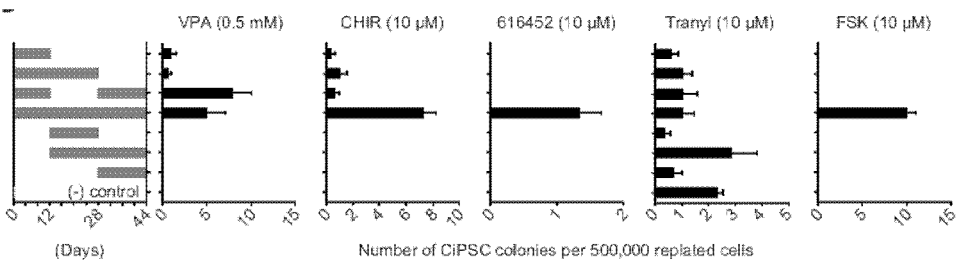
Figure 5I:
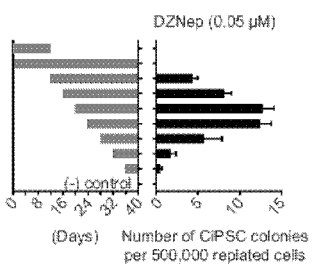
Figure 5J:
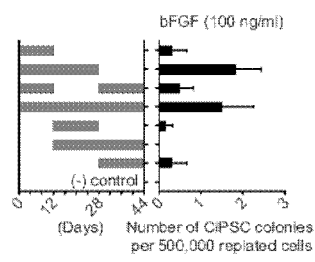
Figure 5K:
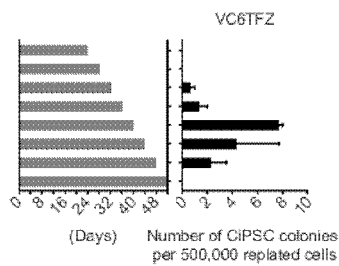

Next, the dosages and treatment duration of the small molecules were optimized leading to generation of 1 to 20 CiPSC colonies from 50,000 initially plated MEFs (FIGS. 5A-K). FIG. 5 A-F show the potential concentrations of VPA, CHIR99021, 616452, tranylcypromine and Forskolin in inducing CiPSCs. They also indicate the reprogramming efficiency may differ from experiments using different concentrations of the small molecules. The preferable concentrasions for each small molecules were shown (VPA, 0.5 mM; CHIR99021, 10 μM; 616452, 10 μM; Forskolin, 50 μM and DZNep 50 nM). FIG. 5G shows the preferable concentration of bFGF (100 ng/mL), it also indicate that bFGF is necessary in inducing CiPSCs. FIG. 5H, I, J show the preferable durations of the small molecules and bFGF that were used in inducing CiPSCs. FIG. 5K indicates the preferable time points to change the medium containing VC6TF into 2i-medium. FIG. 5 A-F show the potential concentrations of VPA, CHIR99021, 616452, tranylcypromine and Forskolin in inducing CiPSCs. They also indicate the reprogramming efficiency may differ from experiments using different concentrations of the small molecules. The preferable concentrasions for each small molecules were shown (VPA, 0.5 mM; CHIR99021, 10 μM; 616452, 10 μM; Forskolin, 50 μM and DZNep 50 nM). FIG. 5G shows the preferable concentration of bFGF (100 ng/mL), it also indicate that bFGF is necessary in inducing CiPSCs. FIG. 5H, I, J show the preferable durations of the small molecules and bFGF that were used in inducing CiPSCs. FIG. 5K indicates the preferable time points to change the medium containing VC6TF into 2i-medium.

Figure 6A:
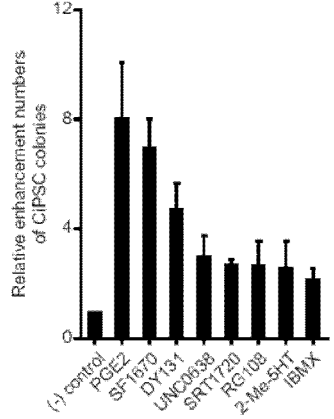
FIGS. 6A-F show validated small molecules improving chemical reprogramming efficiency or kinetics.
Figure 6B:
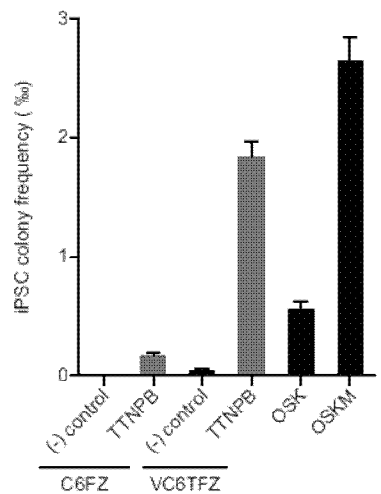
Figure 6C:
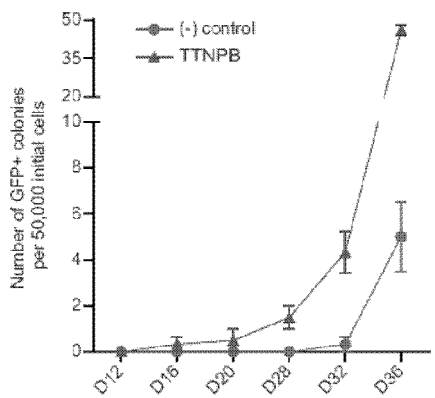
Figure 6D:
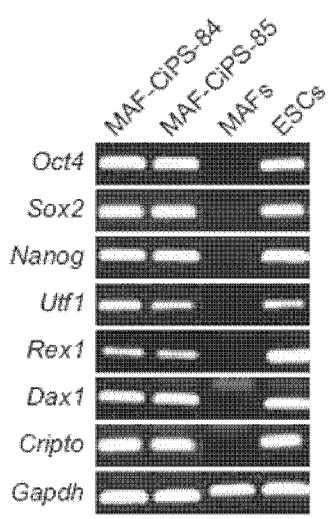
Figure 6E:
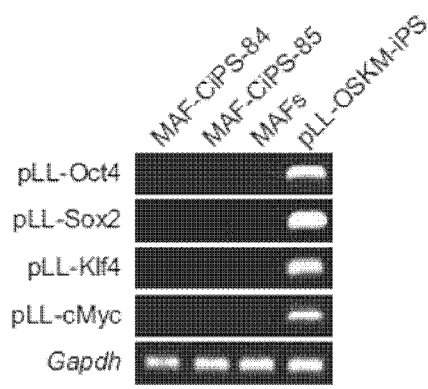
Figure 6F:
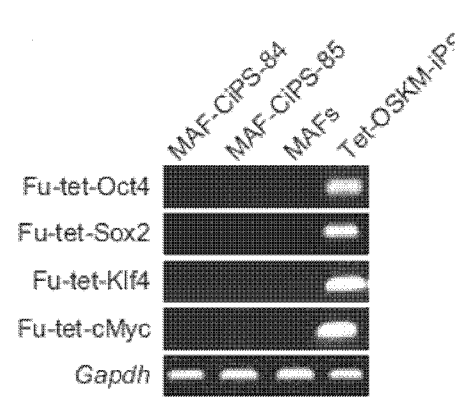
Figure 7A:
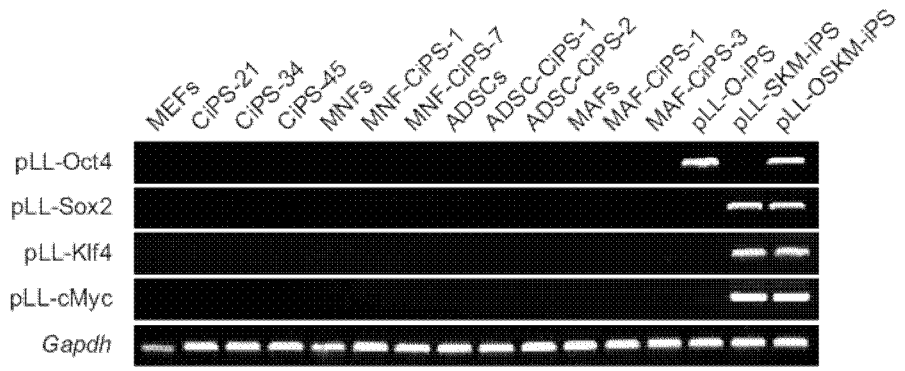
FIGS. 7A-D shows genomic PCR and southern blot analysis showing that CiPSCs were free of transgene contamination.
Figure 7B:
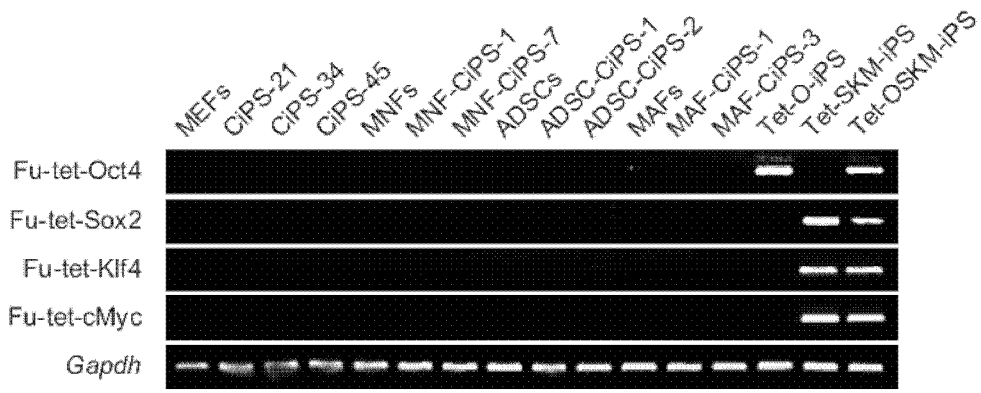
Figures 7C, 7D:
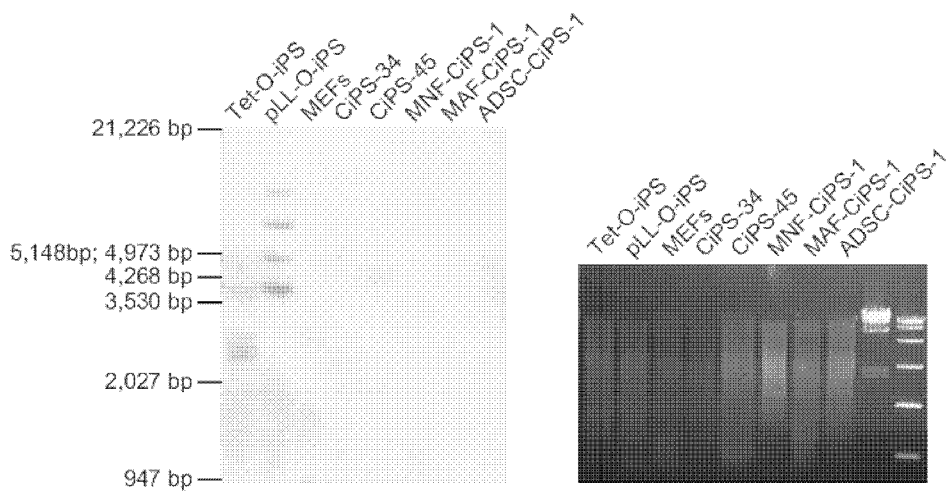
Figure 9C:
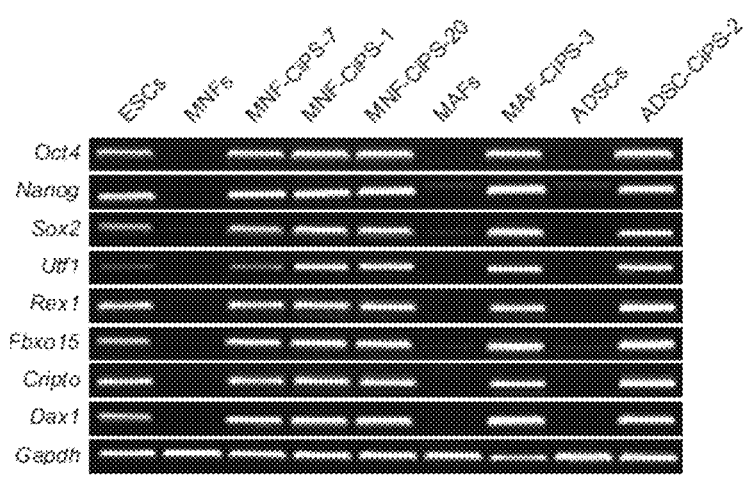
Figure 9D:
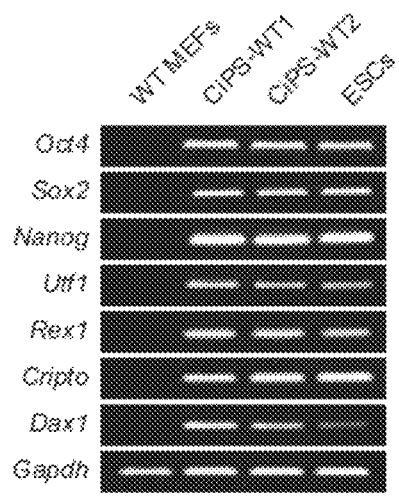

After an additional screen, some small-molecule boosters of chemical reprogramming were identified, among which, a synthetic retinoic acid receptor ligand, TTNPB, enhanced chemical reprogramming efficiency up to a factor of 40, to a frequency comparable to transcription factor—induced reprogramming (up to 0.2%) (FIGS. 6A-C; and Table 1D). An adult chimeric mouse produced with CiPSCs derived from MAFs (clone MAF-CiPS-84) (F) and black F2 off-springs produced with CiPSCs derived from MAFs (clone MAF-CiPS-85). Genomic PCR analysis showed that CiPSCs were free of transgene contamination (FIGS. 6D and E).

Using the small-molecule combination VC6TFZ, CiPSC lines were obtained from mouse neonatal fibroblasts (MNFs), mouse adult fibroblasts (MAFs), and adipose-derived stem cells (ADSCs) with OG cassettes by an efficiency lower by a factor of ~10 than that obtained from MEFs. Table 4.

TABLE 4

Summary of CiPS cell characterization

| Clone Number | Initial Cell Types | Mouse Strain | Chemical Combinations | ESC-like and GFP-positive | Non-transgenic | AP Staining | RT-PCR | Immuno-staining | Gene Expression | Teratoma Assay | Karyotype | DNA | Chimeras | Germ-line Transmission |
|---|---|---|---|---|---|---|---|---|---|---|---|---|---|---|
| CiPS-6 | Mouse embryonic fibroblasts (MEFs) | OG (C57) x ICR | VC6TFMB + Z | ✓ | ✓ | ✓ | ✓ | ✓ | ✓ | ✓ | ✓ | — | ✓ | No |
| CiPS-11 | MEFs | OG (C57) x ICR | VC6TFMB + Z | ✓ | ✓ | ✓ | ✓ | ✓ | — | — | — | ✓ | ✓ | — |
| CiPS-21 | MEFs | OG (C57) x ICR | VC6TFDBS + Z | ✓ | ✓ | ✓ | ✓ | ✓ | ✓ | ✓ | ✓ | ✓ | ✓ | ✓ |
| CiPS-25 | MEFs | OG (C57) x ICR | VC6TFMDBSPR + Z | ✓ | ✓ | ✓ | ✓ | ✓ | ✓ | ✓ | ✓ | ✓ | ✓ | — |
| CiPS-30 | MEFs | OG (C57) x ICR | VC6TFMDBSPR + Z | ✓ | ✓ | ✓ | ✓ | ✓ | ✓ | ✓ | ✓ | ✓ | ✓ | — |
| CiPS-34 | MEFs | OG (C57) x ICR | VC6TFMP + Z | ✓ | ✓ | ✓ | ✓ | ✓ | ✓ | ✓ | ✓ | ✓ | ✓ | ✓ |
| CiPS-36 | MEFs | OG (C57) x ICR | VC6TFMDB + Z | ✓ | ✓ | ✓ | ✓ | ✓ | ✓ | ✓ | ✓ | — | ✓ | No |
| CiPS-39 | MEFs | OG (C57) x ICR | VC6TFMDB + Z | ✓ | ✓ | ✓ | ✓ | ✓ | — | — | — | — | — | — |
| CiPS-42 | MEFs | OG (C57) x ICR | FC6 + Z | ✓ | ✓ | ✓ | ✓ | ✓ | — | ✓ | — | — | ✓ | — |
| CiPS-43 | MEFs | OG (C57) x ICR | FC6 + Z | ✓ | ✓ | ✓ | ✓ | ✓ | — | ✓ | — | — | ✓ | — |
| CiPS-44 | MEFs | OG (C57) x ICR | FC6 + Z | ✓ | ✓ | ✓ | ✓ | ✓ | — | ✓ | — | ✓ | ✓ | — |
| CiPS-45 | MEFs | OG (C57) x ICR | FC6 + Z (w/o bFGF) | ✓ | ✓ | ✓ | ✓ | ✓ | ✓ | ✓ | — | ✓ | ✓ | — |
| CiPS-47 | MEFs | OG (C57) x ICR | VC6TF + Z | ✓ | ✓ | ✓ | ✓ | ✓ | ✓ | — | — | ✓ | ✓ | ✓ |
| CiPS-50 | MEFs | OG (C57) x ICR | VC6F + Z | ✓ | ✓ | — | ✓ | ✓ | ✓ | — | — | ✓ | ✓ | — |
| CiPS-56 | MEFs | OG (C57) x ICR | VC6TFBPS + Z | ✓ | ✓ | ✓ | ✓ | ✓ | — | — | — | — | — | — |
| CiPS-82 | MEFs | OG (C57) x OG (C57) | VC6TF + Z | ✓ | ✓ | ✓ | ✓ | ✓ | — | — | — | — | — | — |
| CiPS-453 | MEFs | OG (C57) x 129 | VC6TFPS + Z | ✓ | ✓ | ✓ | ✓ | ✓ | ✓ | ✓ | — | ✓ | ✓ | ✓ |
| CiPS-WT1 | MEFs (without OG-reporter) | ICR | VC6TFMPS + Z | ✓ | ✓ | ✓ | ✓ | ✓ | ✓ | ✓ | — | ✓ | ✓ | — |
| CiPS-WT2 | MEFs (without OG-reporter) | C57 x 129 | VC6TFMPS + Z | ✓ | ✓ | ✓ | ✓ | ✓ | ✓ | ✓ | — | ✓ | ✓ | — |
| MNF-CiPS-1 | Mouse neonatal fibroblasts (MNFs) | OG (C57) x ICR | VCT6FMDBR + Z | ✓ | ✓ | ✓ | ✓ | ✓ | ✓ | ✓ | ✓ | ✓ | ✓ | No |
| MNF-CiPS-2 | MNFs | OG (C57) x ICR | VC6TFRP + Z | ✓ | ✓ | ✓ | ✓ | — | — | — | — | — | ✓ | — |
| MNF-CiPS-7 | MNFs | OG (C57) x ICR | VC6TFS + Z | ✓ | ✓ | — | ✓ | ✓ | ✓ | — | — | — | ✓ | — |
| ADSC-CiPS-1 | Adipocyte stem cells | OG (C57) x ICR | VC6TFMPS + Z | ✓ | ✓ | — | ✓ | ✓ | — | ✓ | — | — | No | — |
| ADSC-CiPS-2 | Adipocyte stem cells | OG (C57) x ICR | VC6TFMPS + Z | ✓ | ✓ | — | ✓ | — | — | — | — | ✓ | — | — |
| ADSC-CiPS-3 | Adipocyte stem cells | OG (C57) x ICR | VC6TFDM + Z | ✓ | ✓ | ✓ | ✓ | ✓ | — | ✓ | — | ✓ | ✓ | — |
| ADSC-CiPS-4 | Adipocyte stem cells | OG (C57) x ICR | VC6TFDM + Z | ✓ | ✓ | ✓ | ✓ | ✓ | — | ✓ | — | ✓ | — | — |
| MAF-CiPS-1 | Mouse adult fibroblasts (MAFs) | OG (C57) x ICR | VC6TF + Z | ✓ | ✓ | ✓ | ✓ | ✓ | ✓ | ✓ | — | ✓ | ✓ | No |
| MAF-CiPS-3 | MAFs | OG (C57) x ICR | VC6TFDM + Z | ✓ | ✓ | ✓ | ✓ | ✓ | ✓ | ✓ | — | ✓ | ✓ | — |
| MAF-CiPS-62 | MAFs | OG (C57) x ICR | VC6TFBS + Z | ✓ | ✓ | ✓ | ✓ | ✓ | ✓ | ✓ | — | ✓ | ✓ | ✓ |

TABLE 4-continued

Summary of CiPS cell characterization

| Clone Number | Initial Cell Types | Mouse Strain | Chemical Combinations | ESC-like and GFP-positive | Non-transgenic | AP Staining | RT-PCR | Immuno-staining | Gene Expression | Teratoma Assay | Karyotype | DNA | Chimeras | Germ-line Transmission |
|---|---|---|---|---|---|---|---|---|---|---|---|---|---|---|
| MAF-CiPS-63 | MAFs | OG (C57) × ICR | VC6TFPS + Z | ✓ | — | ✓ | ✓ | ✓ | ✓ | ✓ | ✓ | ✓ | ✓ | ✓ |
| MAF-CiPS-73 | MAFs | OG (C57) × ICR | VC6TFBS + Z | ✓ | — | ✓ | ✓ | ✓ | ✓ | — | — | ✓ | ✓ | — |
| MAF-CiPS-76 | MAFs | OG (C57) × ICR | VC6TFB + Z | ✓ | — | ✓ | ✓ | ✓ | ✓ | — | — | ✓ | ✓ | — |
| MAF-CiPS-80 | MAFs | OG (C57) × ICR | FC6 + Z | ✓ | — | ✓ | ✓ | ✓ | ✓ | — | — | ✓ | ✓ | — |
| MAF-CiPS-81 | MAFs | OG (C57) × ICR | FC6 + Z | ✓ | — | ✓ | ✓ | ✓ | ✓ | — | — | ✓ | ✓ | — |
| MAF-CiPS-83 | MAFs | OG (C57) × ICR | VC6TFP + Z | ✓ | — | ✓ | ✓ | ✓ | ✓ | ✓ | ✓ | ✓ | ✓ | — |
| MAF-CiPS-84 | MAFs | OG (C57) × ICR | VC6TFN + Z | ✓ | — | ✓ | ✓ | ✓ | ✓ | ✓ | ✓ | ✓ | ✓ | — |
| MAF-CiPS-85 | MAFs | OG (C57) × ICR | VC6TFN + Z | ✓ | — | ✓ | ✓ | ✓ | ✓ | ✓ | — | ✓ | ✓ | ✓ |
| CiPS-101 | MEFs | OG (C57) × ICR | FC6 | ✓ | — | — | — | — | — | — | — | — | — | — |
| CiPS-102 | MEFs | OG (C57) × ICR | FCT6 + Z | ✓ | — | — | — | — | — | — | — | — | — | — |
| CiPS-103 | MEFs | OG (C57) × ICR | FC6N + Z | ✓ | — | — | — | — | — | — | — | — | — | — |
| CiPS-104 | MEFs | OG (C57) × ICR | FC6T + 4PB + Z | ✓ | — | — | — | — | — | — | — | — | — | — |
| CiPS-105 | MEFs | OG (C57) × ICR | VCT6 + Z | ✓ | — | — | — | — | — | — | — | — | — | — |
| CiPS-31 | MEFs | OG (C57) × ICR | VC6TF | ✓ | ✓ | ✓ | ✓ | ✓ | — | — | — | — | — | — |
| CiPS-106 | MEFs | OG (C57) × ICR | VC6T + DBcAMP + Z | ✓ | — | — | — | — | — | — | — | — | — | — |
| CiPS-107 | MEFs | OG (C57) × ICR | VC6T + IBMX + Z | ✓ | — | — | — | — | — | — | — | — | — | — |
| CiPS-108 | MEFs | OG (C57) × ICR | VC6T + Rloipram + Z | ✓ | — | — | — | — | — | — | — | — | — | — |
| CiPS-109 | MEFs | OG (C57) × ICR | VF6T + TD114-2 + Z | ✓ | — | — | — | — | — | — | — | — | — | — |
| CiPS-110 | MEFs | OG (C57) × ICR | VC6T + NepA | ✓ | — | — | — | — | — | — | — | — | — | — |
| CiPS-111 | MEFs | OG (C57) × ICR | VC6T + Adox | ✓ | — | — | — | — | — | — | — | — | — | — |
| CiPS-112 | MEFs | OG (C57) × ICR | VC6T + DZA | ✓ | — | — | — | — | — | — | — | — | — | — |
| CiPS-113 | MEFs | OG (C57) × ICR | VC6T + Decitabine + EPZ004777 | ✓ | — | — | — | — | — | — | — | — | — | — |
| CiPS-114 | MEFs | OG (C57) × ICR | VC6TFN + Z | ✓ | — | — | — | — | — | — | — | — | — | — |
| CiPS-115 | MEFs | OG (C57) × ICR | VC6TF + AM580 + Z | ✓ | — | — | — | — | — | — | — | — | — | — |
| CiPS-116 | MEFs | OG (C57) × ICR | VC6TF + Ch55 + Z | ✓ | — | — | — | — | — | — | — | — | — | — |
| CiPS-117 | MEFs | OG (C57) × ICR | VC6TF + TTNPB + PGE2 + 5-aza-C | ✓ | — | — | — | — | — | — | — | — | — | — |
| CiPS-118 | MEFs | OG (C57) × ICR | VC6TF + TTNPB + PGE2 + Decitabine | ✓ | ✓ | — | — | — | — | — | — | — | — | — |
| CiPS-119 | MEFs | OG (C57) × ICR | VC6TFDMB + UNC0638 + Scriptaid | ✓ | — | — | ✓ | ✓ | — | ✓ | — | — | — | — |
| CiPS-120 | MEFs | OG (C57) × ICR | VC6TF + Decitabine + EPZ | ✓ | — | — | — | — | — | — | — | — | — | — |

Moreover, CiPSCs were induced from wild-type MEFs without OG cassettes or any other genetic modifications by a comparable efficiency to that achieved from MEFs with OG cassettes. The CiPSCs were also confirmed to be viral-vector free by genomic polymerase chain reaction (PCR) and Southern blot analysis (FIGS. 7A-D).

Furthermore, small molecule combinations were used to generate CiPSCs from neural stem cells and cells obtained from the intestinal epithelium (Table 5).

TABLE 5

Generation of CiPSCs from neural stem cells and cells from the intestinal epithelium

| Clone number | Initial cell type | mouse strain | small molecules | ES-like morphology | genomic PCR | AP staining | RT-PCR |
|---|---|---|---|---|---|---|---|
| IE-CiPS-1 | intestinal epithelium cell | OG (C57) × ICR | VC6TFAM580 + Z | ✓ | ✓ | ND | ✓ |
| NS-CiPS-1 | neural stem cell | OG (C57) × ICR | VC6TFZ + Ch55 + Decitabine + EPZ | ✓ | ✓ | ND | ✓ |

| Clone number | immunofluo-rescence | microarray | teratoma | karyotype | DNA methylation | chimeric mice | germ-line transmission |
|---|---|---|---|---|---|---|---|
| IE-CiPS-1 | ✓ | ✓ | ✓ | ✓ | ✓ | ✓ | ✓ |
| NS-CiPS-1 | ✓ | ND | ✓ | ND | ND | ✓ | ND |

("ND" represents "not determined yet")
AM580 is 4-[(5,6,7,8-Tetrahydro-5,5,8,8-tetramethyl-2-naphthalenyl)carboxamido]benzoic acid]; Ch55 is 4-[(1E)-3-[3,5-bis(1,1-Dimethylethyl)phenyl]-3-oxo-1-propenyl]benzoic acid] and EPZ.
Intestinal and neural stem cells, likes MEF can be reprogrammed using VC6TFZ, without addition of the indicated small molecules, albeit with a different efficiency.

Experiments were next carried out to determine which of these small molecules were critical in inducing CiPSCs. Four essential small molecules (shown below) whose individual withdrawal from the combinations generated significantly reduced GFP-positive colonies and no CiPSCs were identified (FIGS. 8A-B).

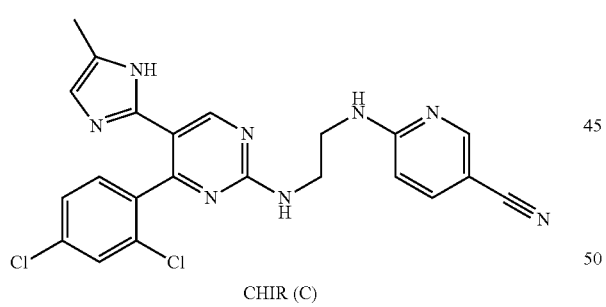

CHIR (C)

FSK (F)

616452 (6)

DZNep (Z)

These small molecules (C6FZ) are: CHIR (C), a glycogen synthase kinase 3 inhibitor (Ying, et al., Nature, 453:519-523 (2008)); 616452 (Zhang, et al., Cell Res. 21:196-204 (2011)), a transforming growth factor-beta receptor inhibitor (Maherali, et al., Curr. Biol., 19:1718-1723 (2009)); FSK (F), a cAMP agonist (FIG. 14F) (Insel, et al., Cell. Mol. Neurobiol., 23:305-314 (2003)); and DZNep (Z), an S-adenosylhomocysteine (SAH) hydrolase inhibitor (FIG. 14A) (Chiang, et al., Pharmacol., Ther. 77:115-134 (1998); Gordon, et al., Eur. J. Biochem., 270:3507-3517 (2003)).

C6FZ was able to induce CiPSCs from both MEFs and MAFs, albeit by an efficiency lower by a factor of 10 than that induced by VC6TFZ (Table 4).

Figure 14A:
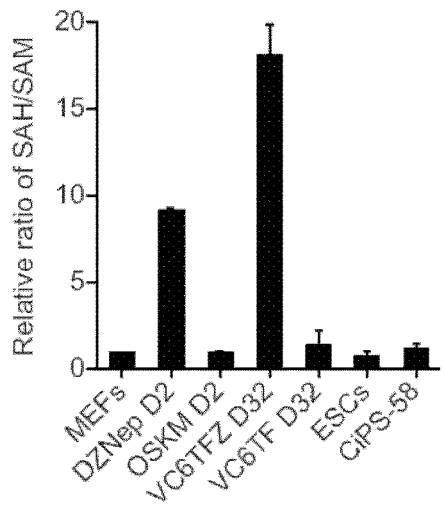
Figure 14F:
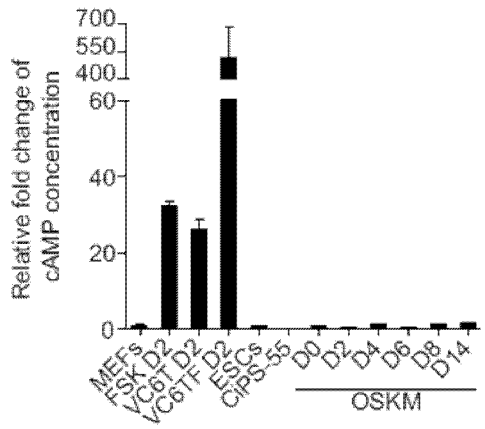
FIG. 14F shows the relative intracellular cAMP levels compared to those in MEFs.
Figure 14G:
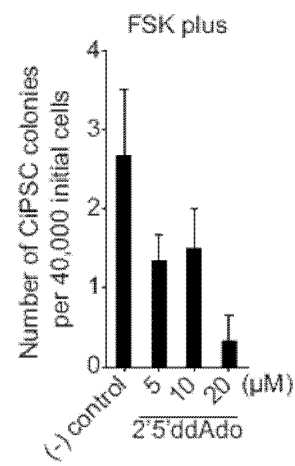
FIG. 14G shows the effect of inhibition of adenylate cyclase by 2'5' ddAdo on the number of CiPSC colonies generated by VC6TFZ. (−) control, DMSO.
Figure 14H:
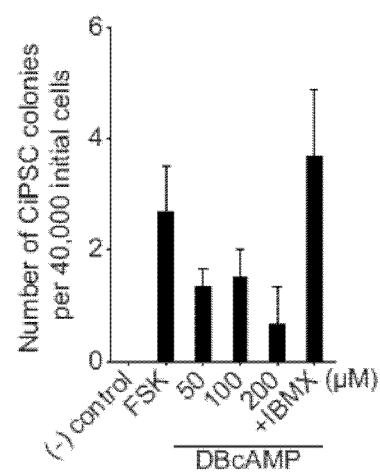
FIG. 14H-J show the effect of replacing FSK with a cAMP analog (DBcAMP with/without IBMX) accompanied by VC6T plus DZNep (VC6TZ) treatment, or the phosphodiesterase inhibitors (Rolipram and IBMX) in combination with VC6TZ during CiPSC induction, on chemical reprogramming.
Figure 14I:
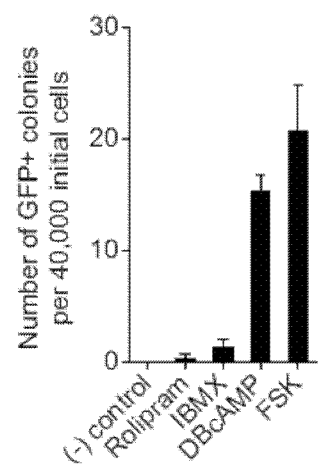
Figure 14J:
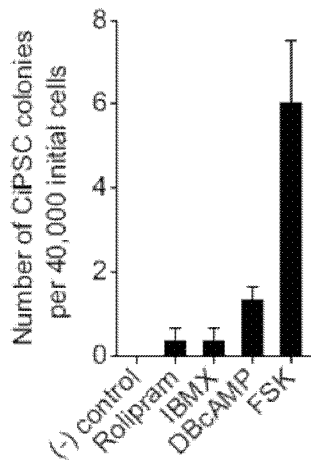
Figure 14K:
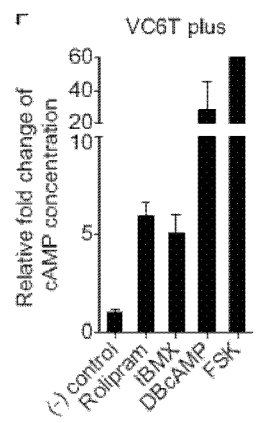
FIG. 14K is a quantification of intracellular cAMP levels following treatment of MEF, with the indicated chemicals. Error bars indicate the s.d. (n≥2)

The effect of inhibiting adenylate cyclase on the number of colonies generated by VC6TFZ was tested. Inhibition of adenylate cyclase by 2'5' ddAdo decreased the number of colonies formed by VC6TFZ (FIG. 14F). The effect of replacing FSK with the cAMP analog (DBcAMP), alone or in combination with phosphodiesterase inhibitors, IBMX, or the phosphodiesterase inhibitor, rolipram and IBMX, on cell reprogramming was also tested. Both DBcAMP and IBMX were used at 50 µM in the combination treatment. The data is shown in FIGS. 14G-J. The intracellular levels of cAMP concentrations in MEF following treatment with rolipram (10 uM), IBMX (50 µM DBcAMP (50 µM) and FSK (10 µM) was compared to control (−) DMSO (FIG. 14K). Forskolin significantly elevates the cAMP level, which is similar to other cAMP agonists (Rolipram and IBMX) or analog (DBcAMP). GFP+ Pluripotent stem cells were induced with other cAMP agonists or analog, which were used to substitute Forskolin. A cAMP inhibitor, 2'5' ddAdo suppressed the efficiency of CiPSC induction. These taken together suggest that Forskolin facilitate chemical reprogramming by modulating cAMP signaling pathway.

Example 4

Characterization of CiPSC Lines

The established CiPSC lines were then further characterized. They grew with a doubling time (14.1 to 15.1 hours) similar to that of ESCs (14.7 hours), maintained alkaline phosphatase activity, and expressed pluripotency markers, as detected by immunofluorescence and reverse transcription (RT)-PCR (FIG. 9A-9D). Specifically, CiPS-25 from passage 21, CiPS-26 from passage 7 and CiPS-30 from passage 22 were cultured for another 6 passages. ESCs (R1) from passage 29 were used as controls. Cells were passaged every three days and seeded at a density of 20,000 cells per well in a 12-well plate without feeder layers in 2i-medium. Error bars indicate the s.d. (n=3). The calculated population doubling times of these cells were 14.8±2.1 (CiPS-25), 15.1 □±1.9 (CiPS-26), and 14.1±1.7 (CiPS-30) hours. These times were equivalent to that of ESCs (14.7±1.2 hours).

The gene expression profiles were similar in CiPSCs, ESCs, and OSKM-iPSCs (iPSCs induced by Oct4, Sox2, Klf4, and c-Myc). DNA methylation state and histone modifications at Oct4 and Nanog promoters in CiPSCs were similar to that in ESCs. In addition, CiPSCs maintained a normal karyotype and genetic integrity for up to 13 passages, i.e., CiPS cells maintain normal chromosome numbers, few copy number variations and genetic mutations, making them safe for further clinical application.

Figure 10:
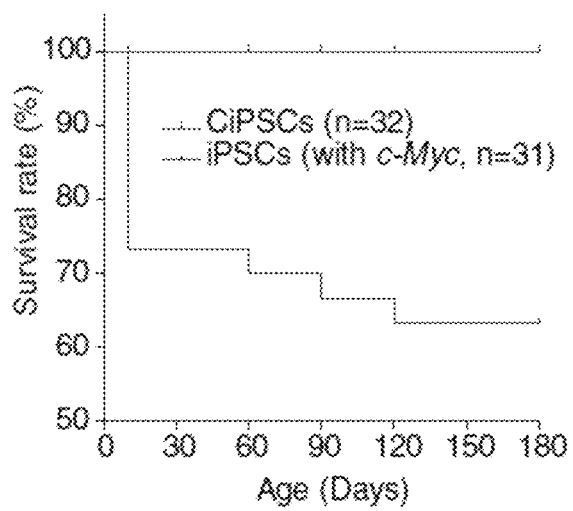
FIG. 10 shows survival curves of chimeras generated from CiPSCs. n, total numbers of chimeras studied.

To characterize their differentiation potential, CiPSCs were injected into immunodeficient (SCID) mice. The cells were able to differentiate into tissues of all three germ layers—respiration epithelium (endoderm); muscle cells (mesoderm); neural epithelium (endoderm) and pigmented epithelium (ectoderm). When injected into eight-cell embryos or blastocysts, CiPSCs were capable of integration into organs of all three germ layers, including gonads and transmission to subsequent generations. An adult chimeric mouse was produced from clone ciPS-34 as well as F2 offspring. Germline contribution of clone CiPS-45 was shown in testes. An adult chimeric mouse was also produced with CiPSCs derived from MNFs (clone MNF-CiPS-1). An adult chimeric mouse was produced with CiPSCs derived from MAFs (clone MAF-CiPS-62). Black F2 offspring were produced with CiPSCs derived from MAFs (clone MAF-CiPS-62). Black F2 offsprings were produced with CiPSCs derived from MAFs (clone MAF-CiPS-63). Chimeras were produced with CiPSCs derived from WT MEFs (clone CiPS-WT1, ICR) that were microinjected into (C57×DBA)× ICR embryos. Unlike chimeric mice generated from iPSCs induced by transcription factors including c-Myc (Nakagawa, et al., *Proc. Natl. Acad. Sci. U.S.A.* 107:14152-14157 (2010)), the chimeric mice generated from CiPSCs were 100% viable and apparently healthy for up to 6 months (FIG. 10). These observations show that the CiPSCs were fully reprogrammed into pluripotency (Table 4).

Example 5

Pluripotency Inducing Properties of Small Molecules

Figure 11A:
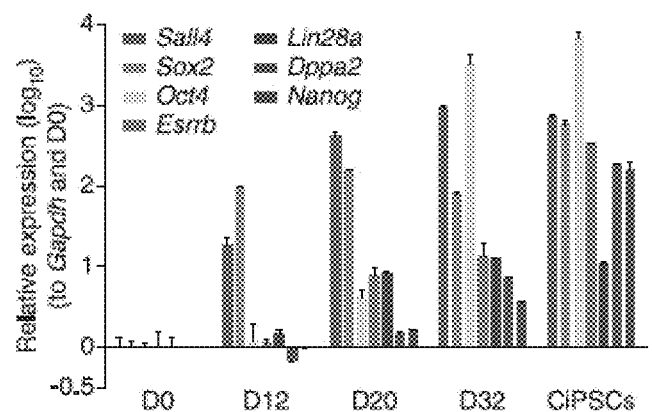
FIGS. 11A-B show the expression of pluripotency-related genes (FIG. 11A) and Gata6, Gata4, and Sox17 (FIG. 11B) as measured by real-time PCR.
Figure 11B:
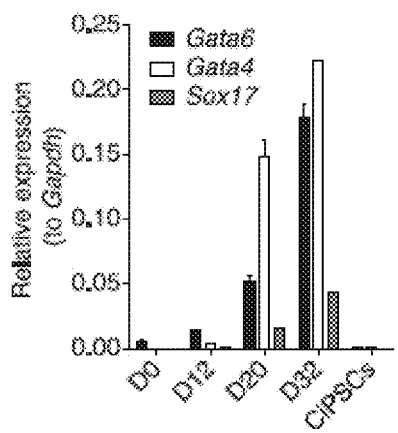
Figure 11C:
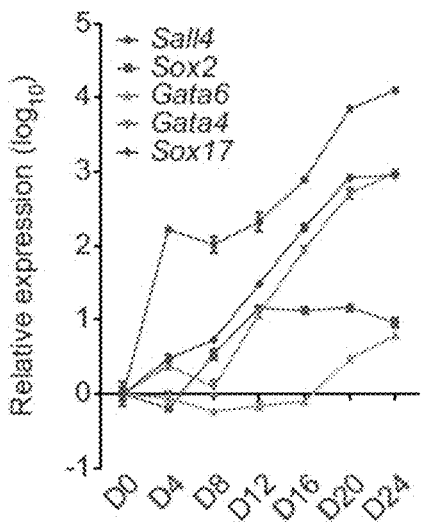
FIGS. 11C-D show expression of Sall4, Sox2, Gata6, Gata4 and Sox17 validated by real-time PCR. The fold changes in Sall4, Sox2, Gata6, Gata4 and Sox17 expression on days 4, 8, 12, 16, 20 and 24 (FIG. 11C) or at 12 h (FIG. 11D) compared with the expression in MEFs on day 0. Error bars indicate the s.d. (n=2).
Figure 11D:
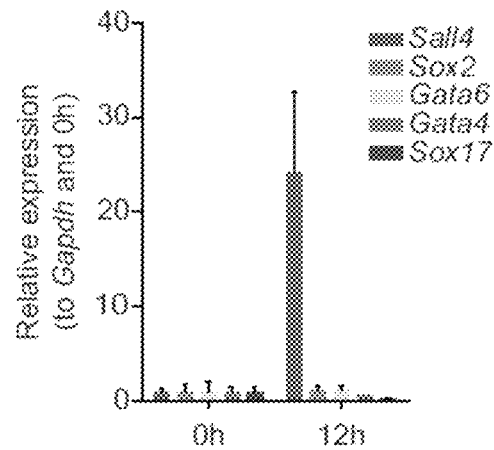
Figure 11E:
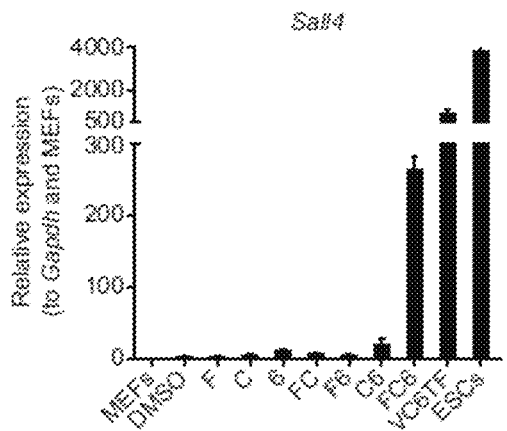
FIGS. 11E-I show the effects of individual and combined chemicals or withdrawing chemicals from VC6TF (or VC6TFZ) on the expression of genes.
Figure 11F:
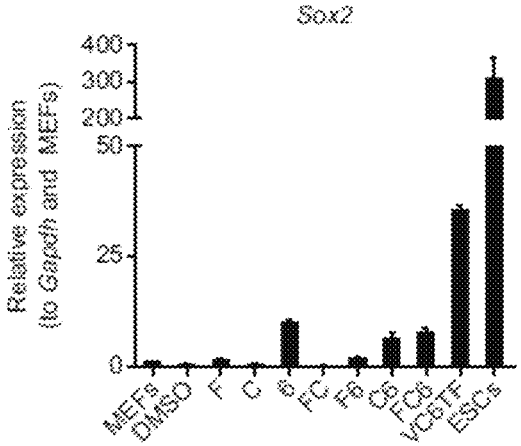
Figure 11G:
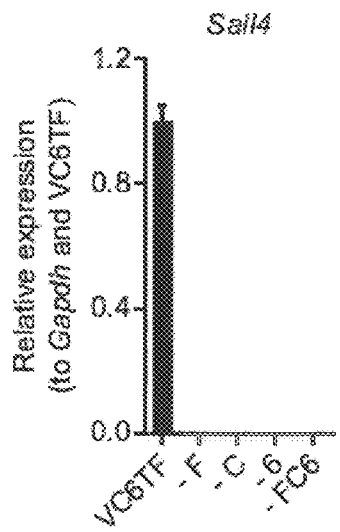
Figure 11H:
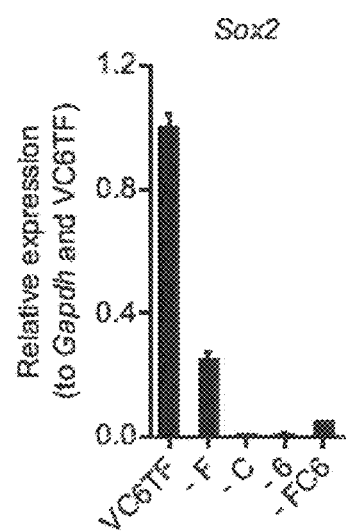
Figure 11I:
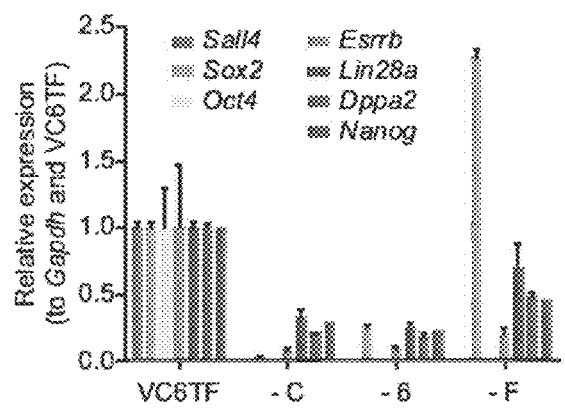
Figure 11J:
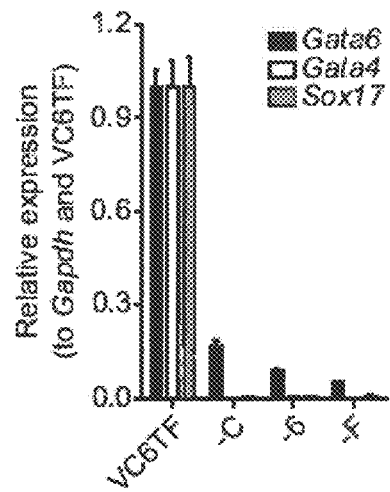
FIG. 11J shows the effects of withdrawing individual chemicals (CHIR, 616452 and FSK) from VC6TFZ on the expression of Gata6, Gata4 and Sox17 on day 32. Error bars indicate the s.d. (n=2).

To better understand the pluripotency-inducing properties of these small molecules, the global gene expression during chemical reprogramming was profiled. To determine clustering of gene expression profiles during chemical reprogramming, cell culture samples treated with VC6TFZ (Z was added from day 20) during chemical reprogramming on day 12, 20 and 32 were analyzed. MEFs on day 0, CiPSCs and ESCs were used as controls. Sequential activation of certain key pluripotency genes was observed, which was validated by real-time PCR and immunofluorescence. Genes that express in ESCs by more than 10 fold and in samples (day 32) by more than 3 fold compared to MEFs (day 0) include Sall4, Sox2, Lin28a, Dppa2, Esrrb, Klf4 and Pou5f1. Genes that express in samples (day 32) by more than 3 folds compared to MEFs (day 0) and ESCs include Sox 17, Gata6 and Gata4. The expression levels of two pluripotency-related genes, Sall4 and Sox2, were most significantly induced in the early phase in response to VC6TF, as was the expression of several extra-embryonic endoderm (XEN) markers Gata4, Gata6, and Sox17 (FIG. 11A-J). The expression of Sall4 was enhanced most significantly as early as 12 hours after small molecule treatment, suggesting that Sall4 may be involved in the first step toward pluripotency in chemical reprogramming (FIG. 11D). With respect to experiments in which small molecules were withdrawn from the treatment used, the data shows that each of Forskolin, CHIR99021 and 616452 is essential in activating the endogenous expression of Sall4 and Sox2 after 12 days (FIGS. 11G and 11H), and the subsequent expression of other pluripotency genes (FIG. 11I). These molecules were also required in activating XEN-genes, such as Gata6, Gata4 and Sox17.

Figure 12C:
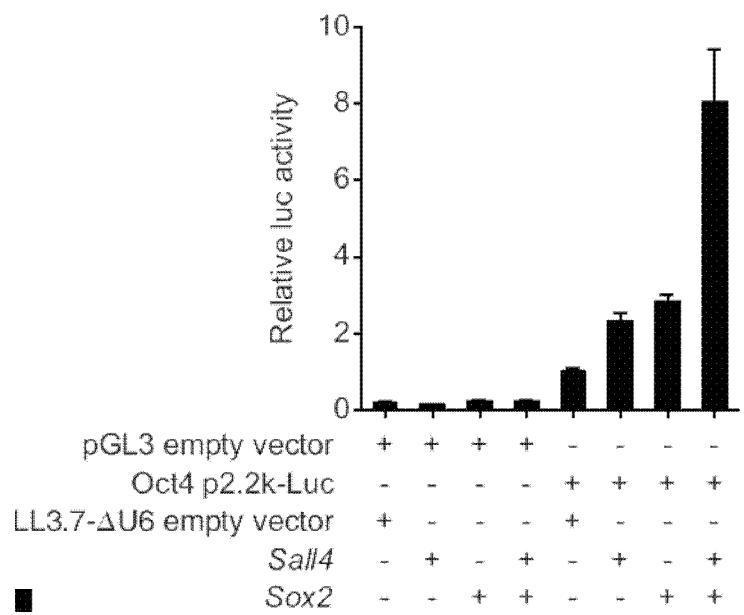
FIG. 12C shows Oct4 promoter-driven luciferase activity was examined in MEFs transfected with Sall4 or/and Sox2 plasmids. Error bars indicate the s.d (n=3).
Figure 12D:
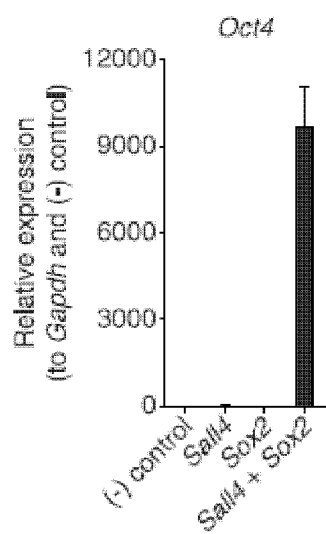
FIGS. 12D-E show Oct4 activation (FIG. 12D) and numbers of GFP-positive and iPSC colonies (FIG. 12E) induced by the overexpression of Sall4 and Sox2, with C6F removed from VC6TFZ.
Figure 12E:
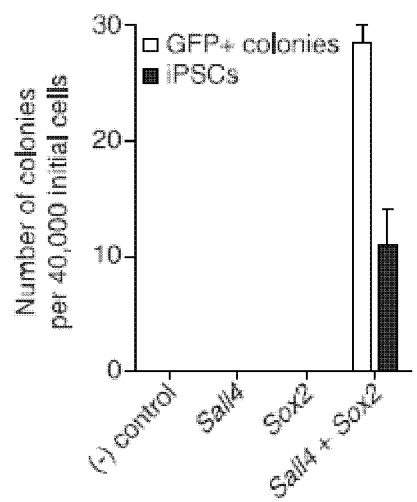
Figure 13A:
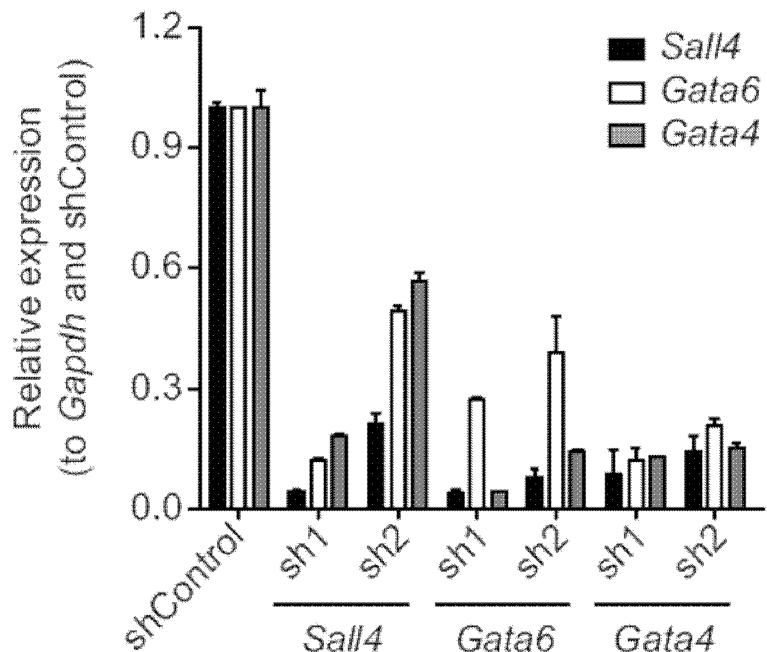
Figure 13B:
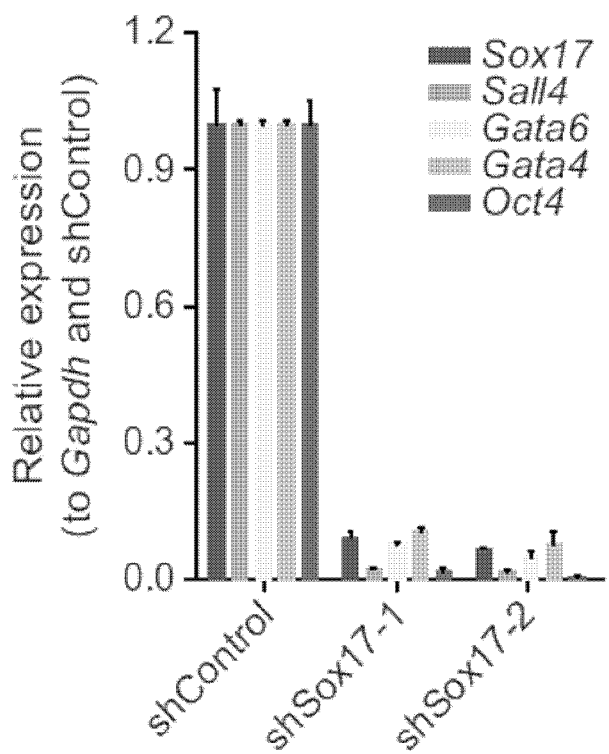
Figure 13F:
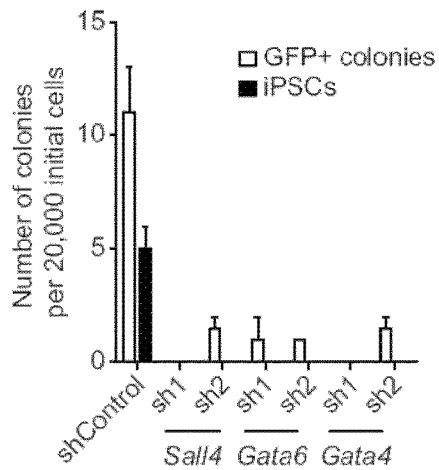
Figure 13G:
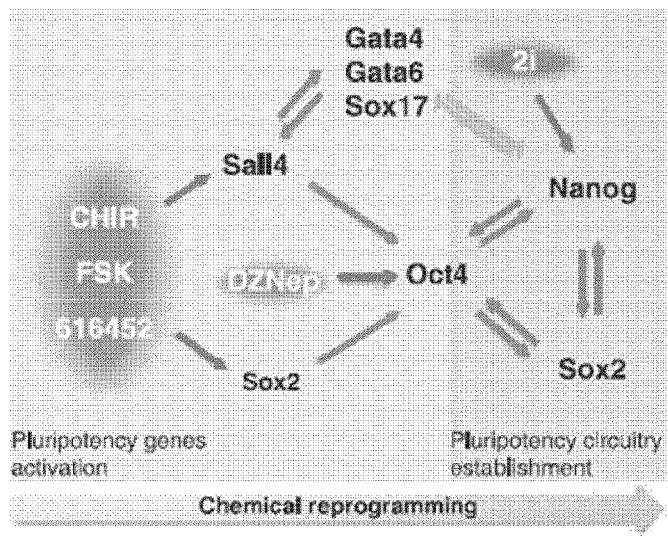
FIG. 13G is a schematic diagram illustrating the stepwise establishment of the pluripotency circuitry during chemical reprogramming.

The roles of the endogenous expression of these genes in chemical reprogramming were examined, using gene overexpression and knockdown strategies. The data shows that the concomitant overexpression of Sall4 and Sox2 was able to activate an Oct4 promoter—driven luciferase reporter (FIGS. 12A-C) and was sufficient to replace C6F in inducing Oct4 expression and generating iPSCs (FIGS. 12D-E). The endogenous expression of Sall4, but not Sox2, requires the activation of the XEN genes, and vice versa (FIGS. 13A-D). This suggests a positive feedback network formed by Sall4, Gata4, Gata6, and Sox17, similar to that previously described in mouse XEN formation (Lim, et al., *Cell Stem Cell*, 3:543-554 (2008)). Knockdown of Sall4 or these XEN genes impaired Oct4 activation and the subsequent establishment of pluripotency (FIGS. 13E-F), inconsistent with previous finding that Gata4 and Gata6 can contribute to inducing pluripotency (Shu, et al., *Cell*, 153:963-975 (2013)). Taken together, these findings revealed a Sall4-mediated molecular pathway that acts in the early phase of chemical reprogramming (FIG. 13G). This step resembles a Sall4-mediated dedifferentiation process in vivo during amphibian limb regeneration (Neff, at al., *Dev. Dyn.*, 240: 979-989 (2011)).

Next, the role of DZNep, which was added in the late phase of chemical reprogramming was investigated. The data shows that Oct4 expression was enhanced significantly after the addition of DZNep in chemical reprogramming (FIG. 11A), and DZNep was critical for stimulating the expression of Oct4 but not the other pluripotency genes (FIG. 11K). As an SAH hydrolase inhibitor, DZNep elevates the concentration ratio of SAH to S-adenosylmethionine (SAM) and may thereby repress the SAM-dependent cellular methylation process (FIG. 14A). Replacement of DZNep by SAH hydrolase inhibitors ((−) Neplanocin A (Nep A), Adenosine periodate (oxidized) Adox and 3-deazaadenosine (DZA)) ((Chiang, et al., *Pharmacol. Ther.*, 77:115-134 (1998), Gordon, et al., *Eur. J. Biochem.* 270:3507-3517 (2003)), in combination with VC6TF treatment to induce CiPSC generation is shown in FIG. 14B The data shows that NEPA, ADOX and DZA are each useful in replacing DZNep in reprogramming. They modulate the same target as DZNep, and can substitute DZNep in generating CiPSCs.

Consistently, DZNep significantly decreased DNA methylation and H3K9 methylation (FIG. 11L) at the Oct4 promoter, which may account for its role in Oct4 activation (Feldman, et al., *Nat. Cell Biol.*, 8:188-194 (2006); Chen, at al., *Nat. Genet.*, 45:34-42 (2013)). The function of DZNep in inducing CiPSCs could not be replaced by down-regulating Ezh2 expression (FIGS. 14C-E). GFP+/ES-like colonies in the primary culture, unlike other colonies, express high mRNA level of Nanog and low level of Gata6, resembling ESCs and the established CiPSCs (data not shown). As master pluripotency genes, Oct4 and Sox2 may thereby activate other pluripotency-related genes and fulfill the chemical reprogramming process, along with the activation of Nanog and the silencing of Gata6, in the presence of 2i (Silva, et al., *PLoS Biol.* 6:e253 (2008), Theunissen, et al., *Curr. Biol.*, 21:65-71 (2011). Boyer, et al., *Cell*, 122:947-956(2005); Chazaud, at al., *Dev. Cell*, 10:615-624 (2006)).

In summary, as a master switch governing pluripotency, Oct4 expression, which is kept repressed in somatic cells by multiple epigenetic modifications, is unlocked in chemical reprogramming by the epigenetic modulator DZNep and stimulated by C6F-induced expression of Sox2 and Sall4 (FIG. 13G).

Figure 15:
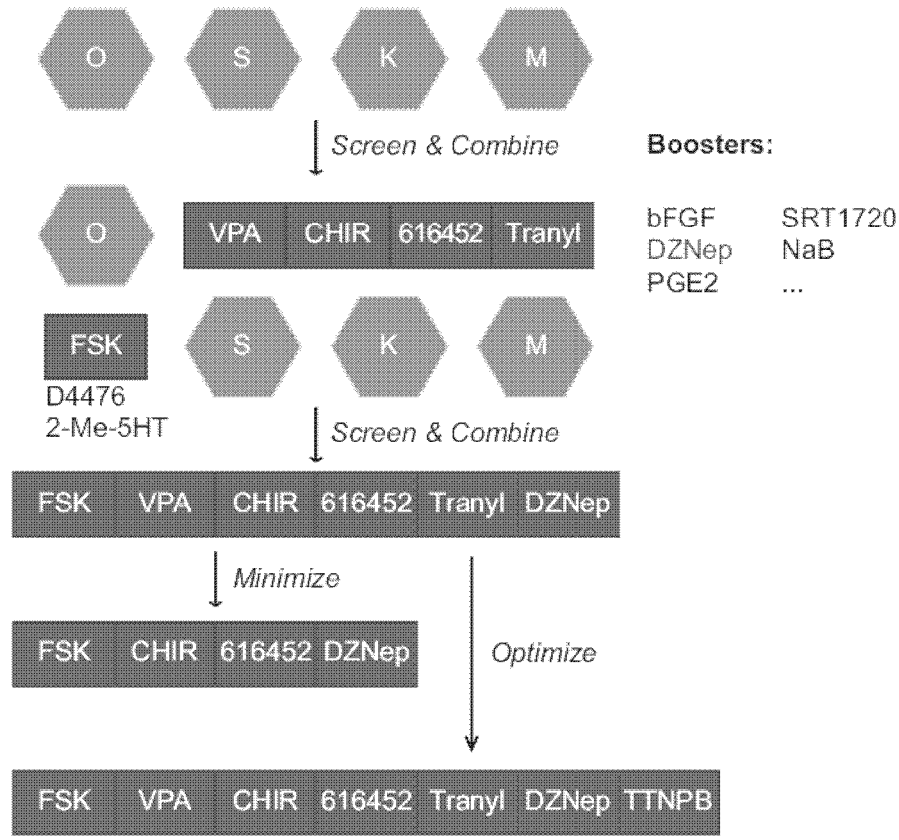
FIG. 15 is a schematic representation of the major steps in the development of chemical reprogramming systems. The blue hexagons represent reprogramming transcription factors, and the red squares represent the major small molecules identified at each step. Reprogramming boosters are displayed on the right, corresponding to different reprogramming conditions. The alternative Oct4 substitutes D4476 and 2-Me-5HT are displayed below FSK. Abbreviations: O(October 4), S (Sox2), K (Klf4), M (c-Myc), Tranyl (Tranylcypromine).

This proof-of-principle study demonstrates that somatic reprogramming toward pluripotency can be manipulated using only small-molecule compounds (FIG. 15). It established that the endogenous pluripotency program can be established by the modulation of molecular pathways non-specific to pluripotency via small molecules rather than by exogenously provided "master genes." These findings increase our understanding about the establishment of cell identities and open up the possibility of generating functionally desirable cell types in regenerative medicine by cell fate reprogramming using specific chemicals or drugs, instead of genetic manipulation and difficult-to-manufacture biologics.

We claim:

1. A kit or cell culture medium composition for inducing pluripotency in non-pluripotent eukaryotic cells, the composition comprising chemical inducers of pluripotency (CIPs) from each of the following groups
   (1) glycogen synthase kinase (GSK) inhibitors,
   (2) TGFβ receptor inhibitors,
   (3) cyclic AMP (cAMP) agonists,
   (4) S-adenosylhomocysteine hydrolase (SAH) inhibitors, and
   (5) optionally, an agent which promotes histone acetylation,
in amounts effective to induce reprograming of the non-pluripotent eukaryotic cells into pluripotent cells.

2. The composition of claim 1, wherein the GSK inhibitor is [6-[[2-[[4-(2,4-Dichlorophenyl)-5-(5-methyl-1H-imidazol-2-yl)-2-pyrimidinyl] amino] ethyl] amino] -3-pyridinecarbonitrile] (CHIR); the TGFβ receptor inhibitor is [2-(3-(6-Methylpyridin-2-yl)-1H-pyrazol-4-yl)-1,5-naphthyridine] (616452); the cAMP agonist is Forskolin (FSK) and the SAH inhibitor is 3-deazaneplanocin A (DZNep).

3. The composition of claim 1, further comprising one or more molecules selected from the group consisting of a histone deacetylase (HDAC) inhibitor, an inhibitor of DNA methylation, an epigenetic modulator, and a protein growth factor and a DOT1L methyl transferase inhibitor.

4. The composition of claim 3 wherein the molecules are selected from the group consisting of valproic acid (VPA), prostaglandin E2 (PGE2), tranylcypromine, rolipram, 5-azacytidine, sodium butyrate, RG108 [N-Phthalyl-L-tryptophan].

5. The composition of claim 3 wherein the DOT1L inhibitor is EPZ004777-[1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea.

6. The composition of claim 1 further comprising small molecules that improve/boost chemical reprograming efficiency selected from the group consisting of SF1670[N-(9,10-Dioxophenanthren-2-yl)-2,2-dimethylpropanamide]; DY131 [N-(4-(Diethylaminobenzylidenyl)-N'-(4-hydroxybenzoyl)-hydrazine; UNC0638 [2-Cyclohexyl-6-methoxy-N-[1-(1-methylethyl)-4-piperidinyl]-7-[3-(1-pyrrolidinyl) propoxy] -4-quinazolinamine]; SRT1720 [N-(2-(3-(piperazin-1-ylmethyl)imidazo [2,1-b]thiazol-]6-yl)phenyl) quinoxaline-2-carboxamide hydrochloride]; 2-Me-5HT (2-methyl-5-hydroxytryptamine); IBMX [3,7-Dihydro-1-methyl-3-(2-methylpropyl)-1H-purine-2, 6-dioneand]; D4476 [(4-[4-(2,3-Dihydro-1,4-benzodioxin-6-yl)-5-(2-pyridinyl)-1H-imidazol-2-yl]benzamide)]; Ch 55 [4-[(1E)-3-[3,5-bis(1,1-Dimethylethyl)phenyl]-3-oxo-1-propenyl] benzoic acid]; AM580 ([4-[(5,6,7,8-Tetrahydro-5,5,8,8-tetramethyl-2-naphthalenyl)carboxamido]benzoic acid]; and TTPB [4-[(E)-2-(5,6,7,8-Tetrahydro-5,5,8,8-tetramethyl-2-naphthalenyl)-1-propenyl]benzoic acid].

7. A method of inducing pluripotency in partially or completely differentiated cells, the method comprising: culturing the cells to be induced with the composition of claim 1 for a period of time effective to induce pluripotency.

8. The method of claim 7, wherein the cells to be induced are selected from the group consisting of multipotent stem cells, cells of hematological origin, cells of embryonic origin, skin derived cells, fibroblasts, adipose-derived cells, epithelial cells, endothelial cells, intestinal cells, mesenchymal cells, parenchymal cells, neurological cells, and connective tissue cells.

9. The method of claim 7, wherein the cells are not transfected to express any of Oct4, KLF4, SOX2, C-Myc or NANOG.

10. The method of claim 7, wherein the cells to be induced are cultured in a reprograming medium comprising the CIPs for a period between 26-36 days.

11. The method of claim 7, wherein the cell culture medium comprises 616452 and Forskolin the entire time before the use of 2i-medium.

12. The method of claim 11 wherein the medium comprises CHIR, 616452, FSK and DZNep (C6FZ).

13. The method of claim 12 wherein the medium comprises VPA, CHIR, 616452, Tranylcypromine FSK (collectively, VC6TF) or VPA, CHIR, 616452, Tranylcypromine, FSK, DZNep (collectively, VC6TFZ).

14. The method of claim 13, wherein the cells are cultured in an ESC (embryonic stem cell) culture medium comprising a glycogen synthase kinase-3 inhibitor and a mitogen-activated protein kinase signaling inhibitor, between day 28 and day 48.

15. The method of claim 13, wherein the cells are cultured for about 16-20 days in reprograming medium including VC6TF, then cultured in VC6TFZ for the remaining period of time required to convert the cells to pluripotent cells.

16. The method of claim 7, wherein the medium comprises CHIR99021 for at least 12 days and the method comprises adding DZNep by day 20 of small molecule treatment.

17. The method of claim 7, wherein the cell culture medium further comprising one or more molecules-selected from the group consisting of a cAMP agonist, epigenetic modulator, deacetylase (HDAC) inhibitor, an inhibitor of DNA methylation, a protein growth factor and a DOT1L methyl transferase inhibitor.

18. The method of claim 7, wherein cells are cultured in an ESC culture medium for about 4 days with glycogen synthase kinase-3 inhibitor and mitogen-activated protein kinase signaling inhibitor after about day 28 post-treatment.

19. The method of claim 7, comprising identifying the pluripotent cells based on morphology, doubling time, the ability of the cell to differentiate into tissues of the three embryonic germ layers, expression of ESC markers and combinations thereof, wherein the ESC markers are selected from the group consisting of alkaline phosphatase (AP); nanog; Rex1; Sox2; Dax1; Sall4; undifferentiated embryonic cell transcription factor (Utf1); stage specific embryonic antigen-4 (SSEA-4) and combinations thereof, and optionally, isolating the pluripotent cells.

20. A composition comprising pluripotent cells obtained by the methods of claim 7.

21. The composition of claim 20, in a carrier, formulated for administration to an individual by injection, implantation of a prosthetic device or tissue engineering matrix.

* * * * *